United States Patent
Giresi

(10) Patent No.: US 12,235,262 B1
(45) Date of Patent: Feb. 25, 2025

(54) METHODS AND SYSTEMS FOR SINGLE CELL PROTEIN ANALYSIS

(71) Applicant: 10X GENOMICS, INC., Pleasanton, CA (US)

(72) Inventor: Paul Giresi, Palo Alto, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 1060 days.

(21) Appl. No.: 17/014,909

(22) Filed: Sep. 8, 2020

Related U.S. Application Data

(60) Provisional application No. 62/897,698, filed on Sep. 9, 2019.

(51) Int. Cl.
G01N 33/543 (2006.01)
G01N 33/68 (2006.01)

(52) U.S. Cl.
CPC ... *G01N 33/54306* (2013.01); *G01N 33/6842* (2013.01)

(58) Field of Classification Search
CPC .............. G01N 33/54306; G01N 33/6842
USPC ........................................... 435/6.11
See application file for complete search history.

(56) References Cited

U.S. PATENT DOCUMENTS

| | | | |
|---|---|---|---|
| 4,124,638 A | 11/1978 | Hansen | |
| 5,185,099 A | 2/1993 | Delpuech et al. | |
| 5,270,183 A | 12/1993 | Corbett et al. | |
| 5,478,893 A | 12/1995 | Ghosh et al. | |
| 5,641,870 A | 6/1997 | Rinderknecht et al. | |
| 5,736,330 A | 4/1998 | Fulton | |
| 5,756,334 A | 5/1998 | Perler et al. | |
| 5,846,719 A | 12/1998 | Brenner et al. | |
| 5,900,481 A | 5/1999 | Lough et al. | |
| 5,942,609 A | 8/1999 | Hunkapiller et al. | |
| 5,994,056 A | 11/1999 | Higuchi | |
| 6,033,880 A | 3/2000 | Haff et al. | |
| 6,057,149 A | 5/2000 | Burns et al. | |

(Continued)

FOREIGN PATENT DOCUMENTS

| | | |
|---|---|---|
| EP | 1019496 B1 | 9/2004 |
| EP | 1841879 A2 | 10/2007 |

(Continued)

OTHER PUBLICATIONS

Leuchowius et al. Parallel visualization of multiple protein complexes in individual cells in tumor tissue. Molecular & Cellular Proteomics. 12.6, 2013, 1563-1571. (Year: 2013).*

(Continued)

*Primary Examiner* — Aaron A Priest
*Assistant Examiner* — Randi Lynn Beil
(74) *Attorney, Agent, or Firm* — Wilson Sonsini Goodrich & Rosati

(57) ABSTRACT

Provided herein are methods identifying protein-protein interactions in a single cell context. In some cases, the methods may be used to measure the abundance of protein-protein interactions in a single cell context. In some cases, the methods may be used to map relationships (e.g., spatial relationships) between proteins in a single cell context. Generally, the methods employ the use of proximity probes coupled with splint oligonucleotides to link information about the relationship of proteins within a single cell context, which may then be read in a downstream process (e.g., a sequencing reaction).

16 Claims, 16 Drawing Sheets

(56) References Cited

U.S. PATENT DOCUMENTS

| | | | |
|---|---|---|---|
| 6,123,798 | A | 9/2000 | Gandhi et al. |
| 6,171,850 | B1 | 1/2001 | Nagle et al. |
| 6,172,218 | B1 | 1/2001 | Brenner |
| 6,176,962 | B1 | 1/2001 | Soane et al. |
| 6,306,590 | B1 | 10/2001 | Mehta et al. |
| 6,327,410 | B1 | 12/2001 | Walt et al. |
| 6,379,929 | B1 | 4/2002 | Burns et al. |
| 6,406,848 | B1 | 6/2002 | Bridgham et al. |
| 6,409,832 | B2 | 6/2002 | Weigl et al. |
| 6,492,118 | B1 | 12/2002 | Abrams et al. |
| 6,524,456 | B1 | 2/2003 | Ramsey et al. |
| 6,586,176 | B1 | 7/2003 | Trnovsky et al. |
| 6,632,655 | B1 | 10/2003 | Mehta et al. |
| 6,806,058 | B2 | 10/2004 | Jesperson et al. |
| 6,890,741 | B2 | 5/2005 | Fan et al. |
| 6,915,679 | B2 | 7/2005 | Chien et al. |
| 7,041,481 | B2 | 5/2006 | Anderson et al. |
| 7,115,400 | B1 | 10/2006 | Adessi et al. |
| 7,129,091 | B2 | 10/2006 | Ismagilov et al. |
| 7,268,167 | B2 | 9/2007 | Higuchi et al. |
| 7,282,370 | B2 | 10/2007 | Bridgham et al. |
| 7,294,503 | B2 | 11/2007 | Quake et al. |
| 7,323,305 | B2 | 1/2008 | Leamon et al. |
| 7,544,473 | B2 | 6/2009 | Brenner |
| 7,622,076 | B2 | 11/2009 | Davies et al. |
| 7,622,280 | B2 | 11/2009 | Holliger et al. |
| 7,638,276 | B2 | 12/2009 | Griffiths et al. |
| 7,645,596 | B2 | 1/2010 | Williams et al. |
| 7,708,949 | B2 | 5/2010 | Stone et al. |
| 7,772,287 | B2 | 8/2010 | Higuchi et al. |
| 7,776,927 | B2 | 8/2010 | Chu et al. |
| 7,842,457 | B2 | 11/2010 | Berka et al. |
| 7,910,354 | B2 | 3/2011 | Drmanac et al. |
| 7,927,797 | B2 | 4/2011 | Nobile et al. |
| 7,960,104 | B2 | 6/2011 | Drmanac et al. |
| 7,968,287 | B2 | 6/2011 | Griffiths et al. |
| 8,003,312 | B2 | 8/2011 | Krutzik et al. |
| 8,053,192 | B2 | 11/2011 | Bignell et al. |
| 8,133,719 | B2 | 3/2012 | Drmanac et al. |
| 8,168,385 | B2 | 5/2012 | Brenner |
| 8,268,564 | B2 | 9/2012 | Roth et al. |
| 8,273,573 | B2 | 9/2012 | Ismagilov et al. |
| 8,298,767 | B2 | 10/2012 | Brenner et al. |
| 8,304,193 | B2 | 11/2012 | Ismagilov et al. |
| 8,318,433 | B2 | 11/2012 | Brenner |
| 8,329,407 | B2 | 12/2012 | Ismagilov et al. |
| 8,592,150 | B2 | 11/2013 | Drmanac et al. |
| 8,658,430 | B2 | 2/2014 | Miller et al. |
| 8,822,148 | B2 | 9/2014 | Ismagliov et al. |
| 8,835,358 | B2 | 9/2014 | Fodor et al. |
| 8,871,444 | B2 | 10/2014 | Griffiths et al. |
| 8,889,083 | B2 | 11/2014 | Ismagilov et al. |
| 8,975,302 | B2 | 3/2015 | Light et al. |
| 9,012,390 | B2 | 4/2015 | Holtze et al. |
| 9,029,083 | B2 | 5/2015 | Griffiths et al. |
| 9,029,085 | B2 | 5/2015 | Agresti et al. |
| 9,085,798 | B2 | 7/2015 | Chee |
| 9,089,844 | B2 | 7/2015 | Hiddessen et al. |
| 9,126,160 | B2 | 9/2015 | Ness et al. |
| 9,156,010 | B2 | 10/2015 | Colston et al. |
| 9,194,861 | B2 | 11/2015 | Hindson et al. |
| 9,216,392 | B2 | 12/2015 | Hindson et al. |
| 9,238,206 | B2 | 1/2016 | Rotem et al. |
| 9,266,104 | B2 | 2/2016 | Link |
| 9,290,808 | B2 | 3/2016 | Fodor et al. |
| 9,328,382 | B2 | 5/2016 | Drmanac et al. |
| 9,347,059 | B2 | 5/2016 | Saxonov |
| 9,371,598 | B2 | 6/2016 | Chee |
| 9,388,465 | B2 | 7/2016 | Hindson et al. |
| 9,417,190 | B2 | 8/2016 | Hindson et al. |
| 9,486,757 | B2 | 11/2016 | Romanowsky et al. |
| 9,498,761 | B2 | 11/2016 | Holtze et al. |
| 9,500,664 | B2 | 11/2016 | Ness et al. |
| 9,567,631 | B2 | 2/2017 | Hindson et al. |
| 9,593,365 | B2 | 3/2017 | Frisen et al. |
| 9,623,384 | B2 | 4/2017 | Hindson et al. |
| 9,637,799 | B2 | 5/2017 | Fan et al. |
| 9,644,204 | B2 | 5/2017 | Hindson et al. |
| 9,650,407 | B2 | 5/2017 | Gartner et al. |
| 9,689,024 | B2 | 6/2017 | Hindson et al. |
| 9,694,361 | B2 | 7/2017 | Bharadwaj et al. |
| 9,701,998 | B2 | 7/2017 | Hindson et al. |
| 9,764,322 | B2 | 9/2017 | Hiddessen et al. |
| 9,824,068 | B2 | 11/2017 | Wong |
| 9,868,979 | B2 | 1/2018 | Chee et al. |
| 9,879,313 | B2 | 1/2018 | Chee et al. |
| 9,946,577 | B1 | 4/2018 | Stafford et al. |
| 9,951,386 | B2 | 4/2018 | Hindson et al. |
| 9,957,558 | B2 | 5/2018 | Leamon et al. |
| 9,975,122 | B2 | 5/2018 | Masquelier et al. |
| 10,011,872 | B1 | 7/2018 | Belgrader et al. |
| 10,017,759 | B2 | 7/2018 | Kaper et al. |
| 10,030,261 | B2 | 7/2018 | Frisen et al. |
| 10,059,989 | B2 | 8/2018 | Giresi et al. |
| 10,144,950 | B2 | 12/2018 | Nolan |
| 10,151,003 | B2 | 12/2018 | Fan et al. |
| 10,221,436 | B2 | 3/2019 | Hardenbol et al. |
| 10,221,442 | B2 | 3/2019 | Hindson et al. |
| 10,253,364 | B2 | 4/2019 | Hindson et al. |
| 10,273,541 | B2 | 4/2019 | Hindson et al. |
| 10,323,279 | B2 | 6/2019 | Hindson et al. |
| 10,338,066 | B2 | 7/2019 | Fan et al. |
| 10,347,365 | B2 | 7/2019 | Wong et al. |
| 10,357,771 | B2 | 7/2019 | Bharadwaj et al. |
| 10,395,758 | B2 | 8/2019 | Schnall-Levin |
| 10,400,280 | B2 | 9/2019 | Hindson et al. |
| 10,428,326 | B2 | 10/2019 | Belhocine et al. |
| 10,533,221 | B2 | 1/2020 | Hindson et al. |
| 10,544,413 | B2 | 1/2020 | Bharadwaj et al. |
| 10,549,279 | B2 | 2/2020 | Bharadwaj et al. |
| 10,557,158 | B2 | 2/2020 | Hardenbol et al. |
| 10,590,244 | B2 | 3/2020 | Delaney et al. |
| 10,633,691 | B2 | 4/2020 | Wu |
| 10,697,008 | B2 | 6/2020 | Blauwkamp et al. |
| 10,745,742 | B2 | 8/2020 | Bent et al. |
| 10,752,949 | B2 | 8/2020 | Hindson et al. |
| 10,774,374 | B2 | 9/2020 | Frisen et al. |
| 10,815,525 | B2 | 10/2020 | Lucero et al. |
| 10,829,815 | B2 | 11/2020 | Bharadwaj et al. |
| 10,837,047 | B2 | 11/2020 | Delaney et al. |
| 10,874,997 | B2 | 12/2020 | Weitz et al. |
| 10,995,333 | B2 | 5/2021 | Pfeiffer |
| 11,371,094 | B2 | 6/2022 | Ryvkin et al. |
| 11,459,607 | B1 | 10/2022 | Terry et al. |
| 11,467,153 | B2 | 10/2022 | Belhocine et al. |
| 11,655,499 | B1 | 5/2023 | Pfeiffer |
| 11,845,983 | B1 | 12/2023 | Belhocine et al. |
| 11,851,683 | B1 | 12/2023 | Maheshwari et al. |
| 11,851,700 | B1 | 12/2023 | Bava et al. |
| 11,952,626 | B2 | 4/2024 | Pfeiffer et al. |
| 2002/0005354 | A1 | 1/2002 | Spence et al. |
| 2002/0051971 | A1 | 5/2002 | Stuelpnagel et al. |
| 2002/0092767 | A1 | 7/2002 | Bjornson et al. |
| 2002/0119455 | A1 | 8/2002 | Chan |
| 2002/0127736 | A1 | 9/2002 | Chou et al. |
| 2003/0027214 | A1 | 2/2003 | Kamb |
| 2003/0036206 | A1 | 2/2003 | Chien et al. |
| 2003/0075446 | A1 | 4/2003 | Culbertson et al. |
| 2003/0082587 | A1 | 5/2003 | Seul et al. |
| 2003/0089605 | A1 | 5/2003 | Timperman |
| 2003/0124509 | A1 | 7/2003 | Kenis et al. |
| 2003/0215862 | A1 | 11/2003 | Parce et al. |
| 2004/0068019 | A1 | 4/2004 | Higuchi et al. |
| 2005/0019839 | A1 | 1/2005 | Jespersen et al. |
| 2005/0037397 | A1 | 2/2005 | Mirkin et al. |
| 2005/0130188 | A1 | 6/2005 | Walt et al. |
| 2005/0250147 | A1 | 11/2005 | Macevicz |
| 2005/0266582 | A1 | 12/2005 | Modlin et al. |
| 2005/0287572 | A1 | 12/2005 | Mathies et al. |
| 2006/0177832 | A1 | 8/2006 | Brenner |
| 2006/0275782 | A1 | 12/2006 | Gunderson et al. |
| 2007/0020640 | A1 | 1/2007 | McCloskey et al. |
| 2007/0042419 | A1 | 2/2007 | Barany et al. |
| 2007/0172873 | A1 | 7/2007 | Brenner et al. |

(56) References Cited

U.S. PATENT DOCUMENTS

| | | |
|---|---|---|
| 2007/0190543 A1 | 8/2007 | Livak |
| 2007/0196397 A1 | 8/2007 | Torii et al. |
| 2007/0264320 A1 | 11/2007 | Lee et al. |
| 2008/0056948 A1 | 3/2008 | Dale et al. |
| 2008/0166720 A1 | 7/2008 | Hsieh et al. |
| 2008/0242560 A1 | 10/2008 | Gunderson et al. |
| 2009/0011943 A1 | 1/2009 | Drmanac et al. |
| 2009/0047713 A1 | 2/2009 | Handique |
| 2009/0099041 A1 | 4/2009 | Church et al. |
| 2009/0131543 A1 | 5/2009 | Weitz et al. |
| 2009/0148961 A1 | 6/2009 | Luchini et al. |
| 2009/0155563 A1 | 6/2009 | Petsev et al. |
| 2009/0202984 A1 | 8/2009 | Cantor |
| 2009/0235990 A1 | 9/2009 | Beer |
| 2009/0269248 A1 | 10/2009 | Falb et al. |
| 2009/0286687 A1 | 11/2009 | Dressman et al. |
| 2010/0035254 A1 | 2/2010 | Williams |
| 2010/0069263 A1 | 3/2010 | Shendure et al. |
| 2010/0086914 A1 | 4/2010 | Bentley et al. |
| 2010/0105112 A1 | 4/2010 | Holtze et al. |
| 2010/0105866 A1 | 4/2010 | Fraden et al. |
| 2010/0184928 A1 | 7/2010 | Kumacheva |
| 2010/0216153 A1 | 8/2010 | Lapidus et al. |
| 2010/0248991 A1 | 9/2010 | Roesler et al. |
| 2010/0304982 A1 | 12/2010 | Hinz et al. |
| 2011/0217736 A1 | 9/2011 | Hindson |
| 2011/0263457 A1 | 10/2011 | Krutzik et al. |
| 2011/0305761 A1 | 12/2011 | Shum et al. |
| 2012/0071331 A1 | 3/2012 | Casbon et al. |
| 2012/0172259 A1 | 7/2012 | Rigatti et al. |
| 2012/0196288 A1 | 8/2012 | Beer |
| 2012/0219947 A1 | 8/2012 | Yurkovetsky et al. |
| 2013/0028812 A1 | 1/2013 | Prieto et al. |
| 2013/0109575 A1 | 5/2013 | Kleinschmidt et al. |
| 2014/0065234 A1 | 3/2014 | Shum et al. |
| 2014/0155295 A1 | 6/2014 | Hindson et al. |
| 2014/0170653 A1 | 6/2014 | Ying |
| 2014/0221239 A1 | 8/2014 | Carman et al. |
| 2014/0242664 A1 | 8/2014 | Zhang et al. |
| 2014/0272996 A1 | 9/2014 | Bemis |
| 2014/0274740 A1 | 9/2014 | Srinivasan et al. |
| 2014/0302503 A1 | 10/2014 | Lowe et al. |
| 2014/0338753 A1 | 11/2014 | Sperling et al. |
| 2014/0378345 A1 | 12/2014 | Hindson et al. |
| 2015/0005188 A1 | 1/2015 | Levner et al. |
| 2015/0267191 A1 | 9/2015 | Steelman et al. |
| 2015/0361418 A1 | 12/2015 | Reed |
| 2015/0376605 A1 | 12/2015 | Jarosz et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0008778 A1 | 1/2016 | Weitz et al. |
| 2016/0024558 A1 | 1/2016 | Hardenbol et al. |
| 2016/0024572 A1 | 1/2016 | Shishkin et al. |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0122753 A1 | 5/2016 | Mikkelsen et al. |
| 2016/0122817 A1 | 5/2016 | Jarosz et al. |
| 2016/0153005 A1 | 6/2016 | Zhang et al. |
| 2016/0201125 A1 | 7/2016 | Samuels et al. |
| 2016/0203196 A1 | 7/2016 | Schnall-Levin et al. |
| 2016/0232291 A1 | 8/2016 | Kyriazopoulou-Panagiotopoulou et al. |
| 2016/0244809 A1 | 8/2016 | Belgrader et al. |
| 2016/0244828 A1 | 8/2016 | Mason |
| 2016/0281160 A1 | 9/2016 | Jarosz et al. |
| 2016/0289669 A1 | 10/2016 | Fan et al. |
| 2016/0289769 A1 | 10/2016 | Schwartz et al. |
| 2016/0314242 A1 | 10/2016 | Schnall-Levin et al. |
| 2016/0348093 A1 | 12/2016 | Price et al. |
| 2017/0009274 A1 | 1/2017 | Abate et al. |
| 2017/0016041 A1 | 1/2017 | Greenfield et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0235876 A1 | 8/2017 | Jaffe et al. |
| 2017/0260584 A1 | 9/2017 | Zheng et al. |
| 2018/0030515 A1 | 2/2018 | Regev et al. |
| 2018/0071695 A1 | 3/2018 | Weitz et al. |
| 2018/0080021 A1 | 3/2018 | Reuter et al. |
| 2018/0080075 A1 | 3/2018 | Brenner et al. |
| 2018/0105808 A1 | 4/2018 | Mikkelsen et al. |
| 2018/0112212 A1 | 4/2018 | Nicol et al. |
| 2018/0208975 A1 | 7/2018 | Peterson et al. |
| 2018/0251825 A1 | 9/2018 | Stoeckius et al. |
| 2018/0273933 A1 | 9/2018 | Gunderson et al. |
| 2018/0312822 A1 | 11/2018 | Lee et al. |
| 2018/0312873 A1 | 11/2018 | Zheng |
| 2018/0320224 A1 | 11/2018 | Gaublomme et al. |
| 2018/0340169 A1 | 11/2018 | Belhocine et al. |
| 2018/0371538 A1 | 12/2018 | Blauwkamp et al. |
| 2018/0371545 A1 | 12/2018 | Wong et al. |
| 2019/0040382 A1 | 2/2019 | Steemers et al. |
| 2019/0060890 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0100632 A1 | 4/2019 | Delaney et al. |
| 2019/0127731 A1 | 5/2019 | McDermott |
| 2019/0134633 A1 | 5/2019 | Bharadwaj et al. |
| 2019/0136316 A1 | 5/2019 | Hindson et al. |
| 2019/0153532 A1 | 5/2019 | Bharadwaj et al. |
| 2019/0176152 A1 | 6/2019 | Bharadwaj et al. |
| 2019/0177800 A1 | 6/2019 | Boutet et al. |
| 2019/0249248 A1* | 8/2019 | Beechem ............ C12Q 1/6841 |
| 2019/0276818 A1 | 9/2019 | Gehring et al. |
| 2019/0323088 A1 | 10/2019 | Boutet et al. |
| 2019/0345636 A1 | 11/2019 | McDermott et al. |
| 2019/0352717 A1 | 11/2019 | Schnall-Levin |
| 2019/0367997 A1 | 12/2019 | Bent et al. |
| 2019/0376118 A1 | 12/2019 | Belhocine et al. |
| 2020/0002763 A1 | 1/2020 | Belgrader et al. |
| 2020/0005902 A1 | 1/2020 | Mellen et al. |
| 2020/0032335 A1 | 1/2020 | Alvarado Martinez |
| 2020/0033237 A1 | 1/2020 | Hindson et al. |
| 2020/0033366 A1 | 1/2020 | Alvarado Martinez |
| 2020/0056223 A1 | 2/2020 | Bell |
| 2020/0105373 A1 | 4/2020 | Zheng |
| 2020/0263232 A1 | 8/2020 | Bell et al. |
| 2021/0190770 A1 | 6/2021 | Delaney et al. |
| 2021/0270703 A1 | 9/2021 | Abousoud |
| 2022/0403375 A1 | 12/2022 | Alvarado Martinez |
| 2023/0167496 A1 | 6/2023 | Bava |
| 2024/0002914 A1 | 1/2024 | Pfeiffer et al. |

FOREIGN PATENT DOCUMENTS

| | | | |
|---|---|---|---|
| EP | 1967592 B1 | | 4/2010 |
| EP | 2540389 A1 | | 1/2013 |
| EP | 2635679 B1 | | 4/2017 |
| GB | 2097692 A | | 11/1982 |
| GB | 2097692 B | | 5/1985 |
| WO | WO-84/02000 | | 5/1984 |
| WO | WO-95/30782 | | 11/1995 |
| WO | WO-99/52708 | | 10/1999 |
| WO | WO-2000008212 A1 | | 2/2000 |
| WO | WO-2001002850 A1 | | 1/2001 |
| WO | WO-0114589 A2 | | 3/2001 |
| WO | WO-0189787 A2 | | 11/2001 |
| WO | WO-0190418 A1 | | 11/2001 |
| WO | WO-2004002627 A2 | | 1/2004 |
| WO | WO-2004065617 A2 | | 8/2004 |
| WO | WO-2004069849 A2 | | 8/2004 |
| WO | WO-2004091763 A2 | | 10/2004 |
| WO | WO-2005021151 A1 | | 3/2005 |
| WO | WO-2005040406 A1 | | 5/2005 |
| WO | WO-2005049787 A9 | | 6/2005 |
| WO | WO-2005082098 A2 | | 9/2005 |
| WO | WO-2006040551 A2 | | 4/2006 |
| WO | WO-2006078841 A1 | | 7/2006 |
| WO | WO-2006096571 A2 | | 9/2006 |
| WO | WO-2007081385 A2 | | 7/2007 |

(56) References Cited

FOREIGN PATENT DOCUMENTS

| | | |
|---|---|---|
| WO | WO-2007081387 A1 | 7/2007 |
| WO | WO-2007089541 A2 | 8/2007 |
| WO | WO-2007133710 A2 | 11/2007 |
| WO | WO-2007140015 A2 | 12/2007 |
| WO | WO-2007147079 A2 | 12/2007 |
| WO | WO-2008021123 A1 | 2/2008 |
| WO | WO-2008109176 A2 | 9/2008 |
| WO | WO-2008121342 A2 | 10/2008 |
| WO | WO-2008134153 A1 | 11/2008 |
| WO | WO-2008150432 A1 | 12/2008 |
| WO | WO-2009011808 A1 | 1/2009 |
| WO | WO-2009015296 A1 | 1/2009 |
| WO | WO-2009085215 A1 | 7/2009 |
| WO | WO-2009152928 A2 | 12/2009 |
| WO | WO-2010033200 A2 | 3/2010 |
| WO | WO-2010104604 A1 | 9/2010 |
| WO | WO-2010117620 A2 | 10/2010 |
| WO | WO-2010148039 A2 | 12/2010 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2012048341 A1 | 4/2012 |
| WO | WO-2012061832 A1 | 5/2012 |
| WO | WO-2012083225 A2 | 6/2012 |
| WO | WO-2012106546 A2 | 8/2012 |
| WO | WO-2012112804 A1 | 8/2012 |
| WO | WO-2012112970 A2 | 8/2012 |
| WO | WO-2012116331 A2 | 8/2012 |
| WO | WO-2012142531 A2 | 10/2012 |
| WO | WO-2012142611 A2 | 10/2012 |
| WO | WO-2012149042 A2 | 11/2012 |
| WO | WO-2012166425 A2 | 12/2012 |
| WO | WO-2012167142 A2 | 12/2012 |
| WO | WO-2013019751 A1 | 2/2013 |
| WO | WO-2013036929 A1 | 3/2013 |
| WO | WO-2013055955 A1 | 4/2013 |
| WO | WO-2013096643 A1 | 6/2013 |
| WO | WO-2013126741 A1 | 8/2013 |
| WO | WO-2013134261 A1 | 9/2013 |
| WO | WO-2014028378 A2 | 2/2014 |
| WO | WO-2014108810 A2 | 7/2014 |
| WO | WO-2014165559 A2 | 10/2014 |
| WO | WO-2014182835 A1 | 11/2014 |
| WO | WO-2014200767 A1 | 12/2014 |
| WO | WO-2015015199 A2 | 2/2015 |
| WO | WO-2015044428 A1 | 4/2015 |
| WO | WO-2015164212 A1 | 10/2015 |
| WO | WO-2016040476 A1 | 3/2016 |
| WO | WO-2016061517 A2 | 4/2016 |
| WO | WO-2016126871 A2 | 8/2016 |
| WO | WO-2016168584 A1 | 10/2016 |
| WO | WO-2016174229 A1 | 11/2016 |
| WO | WO-2017015075 A1 | 1/2017 |
| WO | WO-2017066231 A1 | 4/2017 |
| WO | WO-2017075265 A1 | 5/2017 |
| WO | WO-2017075294 A1 | 5/2017 |
| WO | WO-2017117358 A1 | 7/2017 |
| WO | WO-2017180949 A1 | 10/2017 |
| WO | WO-2017184707 A1 | 10/2017 |
| WO | WO-2017197343 A2 | 11/2017 |
| WO | WO-2018039338 A1 | 3/2018 |
| WO | WO-2018058073 A2 | 3/2018 |
| WO | WO-2018091676 A1 | 5/2018 |
| WO | WO-2018119301 A1 | 6/2018 |
| WO | WO-2018119447 A2 | 6/2018 |
| WO | WO-2018125982 A1 | 7/2018 |
| WO | WO-2018172726 A1 | 9/2018 |
| WO | WO-2018174827 A1 | 9/2018 |
| WO | WO-2018191701 A1 | 10/2018 |
| WO | WO-2018213643 A1 | 11/2018 |
| WO | WO-2018226546 A1 | 12/2018 |
| WO | WO-2018236615 A1 | 12/2018 |
| WO | WO-2019028166 A1 | 2/2019 |
| WO | WO-2019040637 A1 | 2/2019 |
| WO | WO-2019083852 A1 | 5/2019 |
| WO | WO-2019084043 A1 | 5/2019 |
| WO | WO-2019084165 A1 | 5/2019 |
| WO | WO-2019108851 A1 | 6/2019 |
| WO | WO-2019113235 A1 | 6/2019 |
| WO | WO-2019118355 A1 | 6/2019 |
| WO | WO-2019126789 A1 | 6/2019 |
| WO | WO-2019148042 A1 | 8/2019 |
| WO | WO-2019152108 A1 | 8/2019 |
| WO | WO-2019157529 A1 | 8/2019 |
| WO | WO-2019165318 A1 | 8/2019 |
| WO | WO-2019169028 A1 | 9/2019 |
| WO | WO-2019169347 A1 | 9/2019 |
| WO | WO-2019173638 A1 | 9/2019 |
| WO | WO-2019191321 A1 | 10/2019 |
| WO | WO-2019217758 A1 | 11/2019 |
| WO | WO-2020028882 A1 | 2/2020 |
| WO | WO-2020041148 A1 | 2/2020 |
| WO | WO-2020142779 A1 | 7/2020 |
| WO | WO-2020168013 A1 | 8/2020 |
| WO | WO-2020198532 A1 | 10/2020 |
| WO | WO-2021046475 A1 | 3/2021 |
| WO | WO-2021133845 A1 | 7/2021 |
| WO | WO-2021207610 A1 | 10/2021 |
| WO | WO-2021212042 A1 | 10/2021 |
| WO | WO-2021/222302 A1 | 11/2021 |
| WO | WO-2021222301 A1 | 11/2021 |
| WO | WO-2022103712 A1 | 5/2022 |
| WO | WO-2022182682 A1 | 9/2022 |
| WO | WO-2022182785 A1 | 9/2022 |
| WO | WO-2022271908 A1 | 12/2022 |
| WO | WO-2023076528 A2 | 5/2023 |

OTHER PUBLICATIONS

Leuchowius et al. Supplementary figure legends and Supplementary figure 15. Parallel visualization of multiple protein complexes in individual cells in tumor tissue. Molecular & Cellular Proteomics. 12.6, 2013, 5 pages. (Year: 2013).*
Co-pending U.S. Appl. No. 17/148,942, inventors McDermott; Geoffrey et al., filed Jan. 14, 2021.
Co-pending U.S. Appl. No. 17/166,982, inventors McDermott; Geoffrey et al., filed Feb. 3, 2021.
Co-pending U.S. Appl. No. 17/175,542, inventors Maheshwari; Arundhati Shamoni et al., filed Feb. 12, 2021.
Co-pending U.S. Appl. No. 17/220,303, inventor Walter; Dagmar, filed Apr. 1, 2021.
Co-pending U.S. Appl. No. 17/381,612, inventor Martinez; Luigi Jhon Alvarado, filed Jul. 21, 2021.
Co-pending U.S. Appl. No. 17/499,039, inventors Pfeiffer; Katherine et al., filed Oct. 12, 2021.
Co-pending U.S. Appl. No. 17/512,241, inventors Hill; Andrew John et al., filed Oct. 27, 2021.
Co-pending U.S. Appl. No. 17/522,741, inventors Zheng; Xinying et al., filed Nov. 9, 2021.
Co-pending U.S. Appl. No. 17/545,862, inventor Katherine; Pfeiffer, filed Dec. 8, 2021.
Co-pending U.S. Appl. No. 17/573,350, inventor Corey; M. Nemec, filed Jan. 11, 2022.
Co-pending PCT Application No. PCT/US2022/017558, Walter, Dagmar et al. filed Feb. 23, 2022.
Co-pending PCT Application No. PCT/US2022/017377, Pfeiffer, Katherine et al. filed Feb. 22, 2022.
10X Genomics, Inc. CG000153 Rev A. Chromium Single Cell DNA Reagent Kits User Guide. 2018.
10X Genomics, Inc. CG000184 Rev A. Chromium Single Cell 3' Reagent Kits v3 User Guide with Feature Barcoding Technology for CRISPR Screening. 2018.
10X Genomics, Inc. CG000185 Rev B. Chromium Single Cell 3' Reagent Kits User Guide with Feature Barcoding Technology for Cell Surface Protein. 2018.
10X Genomics, Inc. CG000208 Rev E. Chromium Next GEM Single Cell V(D)J reagent Kits v1.1 User Guide with Feature Barcode Technology for Cell Surface Protein. 2020.

(56) References Cited

OTHER PUBLICATIONS

10X Genomics, Inc. CG000209 Rev D. Chromium Next GEM Single Cell ATAC Reagent Kits v1.1 User Guide. 2020.
10X Genomics, Inc. CG000239 Rev B. Visium Spatial Gene Expression Reagent Kits User Guide. 2020.
10X Genomics, Inc. CG00026. Chromium Single Cell 3' Reagent Kit User Guide. 2016.
10X Genomics, Inc. LIT00003 Rev B Chromium Genome Solution Application Note. 2017.
Abate, A.R. et al. "Beating Poisson encapsulation statistics using close-packed ordering" Lab on a Chip (Sep. 21, 2009) 9(18):2628-2631.
Adamson, et al. A Multiplexed Single-Cell CRISPR Screening Platform Enables Systematic Dissection of the Unfolded Protein Response. Cell. Dec. 15, 2016;167(7):1867-1882.e21. doi: 10.1016/j.cell.2016.11.048.
Adamson et al., "Production of arrays of chemically distinct nanolitre plugs via repeated splitting in microfluidic devices", Lab Chip 6(9): 1178-1186 (Sep. 2006).
Agasti, S.S. et al. "Photocleavable DNA barcode-antibody conjugates allow sensitive and multiplexed protein analysis in single cell" J Am Chem Soc (2012) 134(45):18499-18502.
Amini, S. et al. "Haplotype-resolved whole-genome sequencing by contiguity-preserving transposition and combinatorial indexing" Nature Genetics (2014) 46:1343-1349 doi:10.1038/ng.3119.
Anna et al.: Formation of dispersions using "flow focusing" in microchannels: Applied Physics Letters, vol. 82, No. 3, pp. 364-366 (2003).
Baret, "Surfactants in droplet-based microfluidics" Lab Chip (12(3):422-433 (2012).
Beer et al. On-Chip, Real-Time, Single-Copy Polymerase Chain Reaction in Picoliter Droplets. Anal Chem 79:8471-8475 (2007).
Braeckmans et al., Scanning the Code. Modern Drug Discovery. 2003:28-32.
Brenner, et al. "In vitro cloning of complex mixtures of DNA on microbeads: physical separation of differentially expressed cDNAs." Proc Natl Acad Sci U S A. Feb. 15, 2000;97(4):1665-70.
Buchman GW, et al. Selective RNA amplification: a novel method using dUMP-containing primers and uracil DNA glycosylase. PCR Methods Appl. Aug. 1993; 3(1):28-31.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-15. Epub Aug. 9, 2001.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Chien et al. "Multiport flow-control system for lab-on-a-chip microfluidic devices", Fresenius J. Anal Chem, 371:106-111 (Jul. 27, 2001).
Chu, et al. Controllable monodisperse multiple emulsions. Angew Chem Int Ed Engl. 2007;46(47):8970-4.
Clausell-Tormos et al., "Droplet-based microfluidic platforms for the encapsulation and screening of mammalian cells and multicellular organisms", Chem. Biol. 15:427-437 (2008).
Co-pending U.S. Appl. No. 16/434,076, filed Jun. 6, 2019.
Co-pending U.S. Appl. No. 16/434,084, filed Jun. 6, 2019.
Co-pending U.S. Appl. No. 16/434,102, filed Jun. 6, 2019.
Co-pending U.S. Appl. No. 16/708,214, filed Dec. 9, 2019.
Co-pending U.S. Appl. No. 16/737,762, filed Jan. 8, 2020.
Co-pending U.S. Appl. No. 16/737,770, filed Jan. 8, 2020.
Co-pending U.S. Appl. No. 16/789,273, filed Feb. 12, 2020.
Co-pending U.S. Appl. No. 16/789,287, filed Feb. 12, 2020.
Co-pending U.S. Appl. No. 16/800,450, filed Feb. 25, 2020.
Co-pending U.S. Appl. No. 16/814,908, filed Mar. 10, 2020.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
Datlinger et al. Pooled CRISPR screening with single-cell transcriptome readout. Nature Methods Advance Online Publication (Jan. 18, 2017). DOI: http://www.nature.com/doifinder/10.1038/nmeth.4177. 10 pages.
Delehanty, et al. Peptides for specific intracellular delivery and targeting of nanoparticles: implications for developing nanoparticle-mediated drug delivery. Ther Deliv. Sep. 2010;1(3):411-33.
Dey, et al. Integrated Genome and Transcriptome Sequencing from the Same Cell. Nature biotechnology 33.3 (2015): 285-289. PMC. Web. Dec. 18, 2017.
Dixit, et al. Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.
Drmanac et al., Sequencing by hybridization (SBH): advantages, achievements, and opportunities. Adv Biochem Eng Biotechnol. 2002;77 :75-101.
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Esser-Kahn, et al. Triggered release from polymer capsules. Macromolecules. 2011; 44:5539-5553.
Gaublomme, et al. Nuclei multiplexing with barcoded antibodies for single-nucleus genomics. Nat Commun. Jul. 2, 2019;10(1):2907. doi: 10.1038/s41467-019-10756-2.
Gehring, et al. Highly Multiplexed Single-Cell RNA-seq for Defining Cell Population and Transcriptional Spaces. bioRxiv (2018): 315333.
Gericke, et al. Functional cellulose beads: preparation, characterization, and applications. Chemical reviews 113.7 (2013): 4812-4836.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
Holtze, et al. Biocompatible surfactants for water-in-fluorocarbon emulsions. Lab Chip. Oct. 2008;8(10):1632-9. doi: 10.1039/b806706f. Epub Sep. 2, 2008.
Huebner, "Quantitative detection of protein expression in single cells using droplet microfluidics", Chem. Commun. 1218-1220 (2007).
Hug, et al. Measurement of the No. of molecules of a single mRNA species in a complex mRNA preparation. J Theor Biol. Apr. 21, 2003;221(4):615-24.
Islam, et al. Highly multiplexed and strand-specific single-cell RNA 5' end sequencing. Nat Protoc. Apr. 5, 2012;7(5):813-28. doi: 10.1038/nprot.2012.022.
Jaitin, et al. Massively parallel single-cell RNA-seq for marker-free decomposition of tissues into cell types. Science. Feb. 14, 2014;343(6172):776-9. doi: 10.1126/science.1247651.
Jarosz, M. et al. "Using 1ng of DNA to detect haplotype phasing and gene fusions from whole exome sequencing of cancer cell lines" Cancer Res (2015) 75(supp15):4742.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Kenis, et al. Microfabrication Inside Capillaries Using Multiphase Laminar Flow Patterning. Science. 1999; 285:83-85.

(56) References Cited

OTHER PUBLICATIONS

Kester, et al. Single-Cell Transcriptomics Meets Lineage Tracing. Cell Stem Cell. Aug. 2, 2018;23(2):166-179. doi: 10.1016/j.stem.2018.04.014. Epub May 10, 2018.
Kivioja, et al. Counting absolute Nos. of molecules using unique molecular identifiers. Nat Methods. Nov. 20, 2011;9(1):72-4.
Klein, et al. Droplet barcoding for single-cell transcriptomics applied to embryonic stem cells. Cell. May 21, 2015; 161:1187-1201.
Korlach et al., Methods in Enzymology, Real-Time DNA Sequencing from Single Polymerase Molecules, (2010) 472:431-455.
Koster et al., "Drop-based microfluidic devices for encapsulation of single cells", Lab on a Chip the Royal Soc. of Chem. 8: 1110-1115 (2008).
Lagally, et al. Single-Molecular DNA Amplification and Analysis in an Integrated Microfluidic Device. Anal Chem. Feb. 1, 2001;73(3):565-70.
Lennon et al. A scalable, fully automated process for construction of sequence-ready barcoded libraries for 454. Genome Biology 11:R15 (2010).
Love, "A microengraving method for rapid selection of single cells producing antigen-specific antibodies", Nature Biotech, 24:6 703 (Jun. 2006).
MacAulay, et al. G&T-seq: parallel sequencing of single-cell genomes and transcriptomes. Nature Methods, 2015, p. 1-7.
MacAulay, et al. Single-Cell Multiomics: Multiple Measurements from Single Cells. Trends in Genetics 33.2 (2017): 155-168. PMC. Web. Dec. 18, 2017.
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Madl, et al. "Bioorthogonal Strategies for Engineering Extracellular matrices", Madal, Chritopher, Adv. Funct. Master. Jan. 19, 2018, vol. 28, 1706046, pp. 1-21.
Mair, et al. Injection molded microfluidic chips featuring integrated interconnects. Lab Chip. Oct. 2006;6(10):1346-54. Epub Jul. 31, 2006.
Mazutis, et al. Single-Cell Analysis and Sorting Using Droplet-Based Microfluidics. Nat Protoc. 8(5): 870-891 (May 2013).
McCoy, R. et al. "Illumina TruSeq Synthetic Long-Reads Empower De Novo Assembly and Resolve Complex, Highly-Repetitive Transposable Elements" PLOS (2014) 9(9):e1016689.
McGinnis et al. Multi-seq: sample multiplexing for single-cell RNA sequencing using lipid-tagged indices. Nat Methods. Jul. 2019;16(7):619-626. doi: 10.1038/s41592-019-0433-8. Epub Jun. 17, 2019.
McGinnis, et al. Multi-seq: Scalable sample multiplexing for single-cell RNA sequencing using lipid-tagged indices. bioRxiv (2018) 387241; doi: https://doi.org/10.1101/387241. . . .
Microfluidic ChipShop. Microfluidic product catalogue. Oct. 2009.
Mimitou, et al. Expanding the CITE-seq tool-kit: Detection of proteins, transcriptomes, clonotypes and CRISPR perturbations with multiplexing, in a single assay. bioRxiv preprint first posted online Nov. 8, 2018; doi: http://dx.doi.org/10.1101/466466.
Navin. The first five years of single-cell cancer genomics and beyond. Genome Res. Oct. 2015;25(10):1499-507. doi: 10.1101/gr.191098.115.
Nisisako, et al. Droplet formation in a microchannel network. Lab Chip. Feb. 2002;2(1):24-6. Epub Jan. 18, 2002.
Nisisako, T. et al. Droplet Formation in a Microchannel on PMMA Plate. Micro Total Analysis Systems. 2001. Kluwer Academic Publishers. pp. 137-138.
Nisisako, T. et al., Microfluidics large-scale integration on a chip for mass production of monodisperse droplets and particles, The Royal Society of Chemistry: Lab Chip, (Nov. 23, 2007) 8:287-293.
Novak, R. et al., "Single cell multiplex gene detection and sequencing using microfluidicallygenerated agarose emulsions" Angew. Chem. Int. Ed. Engl. (2011) 50(2):390-395.
Orakdogen, N. "Novel responsive poly(N,N-dimethylaminoethyl methacrylate) gel beads: preparation, mechanical properties and pH-dependent swelling behavior" J Polym Res (2012) 19:9914.

Perrott, Jimmy. Optimization and Improvement of Emulsion PCR for the Ion Torrent Next-Generation Sequencing Platform. (2011) Thesis.
Peters, B.A. et al. Accurate whole-genome sequencing and haplotyping from 10 to 20 human cells. Nature, 487(7406):190-195 (Jul. 11, 2012).
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Priest, et al. Generation of Monodisperse Gel Emulsions in a Microfluidic Device, Applied Physics Letters, 88:024106 (2006).
Pushkarev et al. "Single-molecule sequencing of an individual human genome," Nature Biotech (2009) 27:847-850.
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-11. URL:http://454.com/downloads/my454/documentation/technical-bulletins/TCB-09004 Using MultiplexIdentifierAdaptorsForTheGSFLXTitaniumSeriesChemistry-BasicMIDSet.pdf.
Rosenberg, et al. Single-cell profiling of the developing mouse brain and spinal cord with split-pool barcoding. Science. Apr. 13, 2018;360(6385):176-182. doi: 10.1126/science.aam8999. Epub Mar. 15, 2018.
Rotem, A. et al., "High-throughput single-cell labeling (Hi-SCL) for RNA-Seq using drop-based microfluidics" PLOS One (May 22, 2015) 0116328 (14 pages).
Saikia, et al. Simultaneous multiplexed amplicon sequencing and transcriptome profiling in single cells. Nat Methods. Jan. 2019; 16(1):59-62. doi: 10.1038/s41592-018-0259-9. Epub Dec. 17, 2018.
Schmidt, et al. Quantitative analysis of synthetic cell lineage tracing using nuclease barcoding. ACS synthetic biology 6.6 (2017): 936-942.
Schubert, et al. Microemulsifying fluorinated oils with mixtures of fluorinated and hydrogenated surfactants. Colloids and Surfaces A; Physicochemical and Engineering Aspects, 84(1994) 97-106.
Seiffert, et al. Microfluidic fabrication of smart microgels from macromolecular precursors.Polymer. vol. 51, Issue 25, Nov. 26, 2010, pp. 5883-5889.
Seiffert, S. et al., "Smart microgel capsules from macromolecular precursors" J. Am. Chem. Soc. (2010) 132:6606-6609.
Shah, et al. "Fabrication of mono disperse thermosensitive microgels and gel capsules in micro fluidic devices", Soft Matter, 4:2303-2309 (2008).
Shahi, et al. Abseq: Ultrahigh-throughput single cell protein profiling with droplet microfluidic barcoding. Sci Rep. 2017; 7: 44447. Published online Mar. 14, 2017. doi: 10.1038/srep44447.
Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/Science.1117839.
Smith, et al. Highly-multiplexed barcode sequencing: an efficient method for parallel analysis of pooled samples. Nucleic Acids Research, 38(13): e142 (2010).
Song, et al. Reactions in droplets in microfluidic channels. Angew Chem Int Ed Engl. Nov. 13, 2006;45(44):7336-56.
Srivatsan, et al. Massively multiplex chemical transcriptomics at single-cell resolution. Science (New York, NY) 367.6473 (2020): 45-51.
Stoeckius, et al. Cell Hashing with barcoded antibodies enables multiplexing and doublet detection for single cell genomics. Genome Biol. Dec. 19, 2018;19(1):224. doi: 10.1186/s13059-018-1603-1.
Stoeckius, et al. Large-scale simultaneous measurement of epitopes and transcriptomes in single cells. bioRxiv 113068; doi: https://doi.org/10.1101/113068; (Mar. 2, 2017).
Stoeckius, et al. Simultaneous epitope and transcriptome measurement in single cells. Nature methods. Jul. 31, 2017.

(56) References Cited

OTHER PUBLICATIONS

Thaxton, C.S. et al. "A Bio-Bar-Code Assay Based Upon Dithiothreitol Oligonucleotide Release" Anal Chem (2005) 77:8174-8178.

Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.

Thorsen, et al. Dynamic pattern formation in a vesicle-generating microfluidic device. Physical Review Letters. American Physical Society. 2001; 86(18):4163-4166.

Tonelli, et al. Perfluoropolyether functional oligomers: unusual reactivity in organic chemistry. Journal of fluorine chemistry. 2002; 118(1)107-121.

Turchinovich, et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.

Ullal et al. Cancer Cell Profiling by Barcoding Allows Multiplexed Protein Analysis in Fine-Needle Aspirates. Sci Transl Med. Jan. 15, 2014; 6(219): 219ra9.

Uttamapinant, et al. Fast, cell-compatible click chemistry with copper-chelating azides for biomolecular labeling.Angew. Chem. Int. End. Engl., Jun. 11, 2012: 51(24) pp. 5852-5856.

Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.

Weigl, et al. Microfluidic Diffusion-Based Separation and Detection. Science. 1999; pp. 346-347.

Williams, et al. Amplification of complex gene libraries by emulsion PCR. Nature Methods. 2006;3(7):545-50.

Wong, et al. Multiplexed Barcoded CRISPR-Cas9 Screening Enabled By CombiGEM. PNAS. Mar. 1, 2016, vol. 113, pp. 2544-2549.

Zapata et al. Engineering linear F(ab')2 fragments for efficient production in *Escherichia coli* and enhanced antiproliferative activity. Protein Eng. 8(10):1057-1062 (1995).

Zhang, et al. One-step fabrication of supramolecular microcapsules from microfluidic droplets. Science. Feb. 10, 2012;335(6069):690-4. doi: 10.1126/science.1215416.

Zheng, et al. Massively parallel digital transcriptional profiling of single cells. Nat Commun. Jan. 16, 2017;8:14049. doi: 10.1038/ncomms14049.

Zheng, X.Y. et al. "Haplotyping germline and cancer genomes with high-throughput linked-read sequencing" Nature Biotech (Feb. 1, 2016) 34(3):303-311.

Zhu, et al. Reverse transcriptase template switching: a SMART approach for full-length cDNA library construction. Biotechniques. Apr. 2001;30(4):892-7.

PCT/US2020/017785 Application filed on Feb. 11, 2020 by Ziraldo, Solongo B. et al.

PCT/US2020/017789 Application filed on Feb. 11, 2020 by Belhocine, Zahara Kamila et al.

Co-pending U.S. Appl. No. 17/517,408, inventors Salmanzadeh; Alireza et al., filed Nov. 2, 2021.

Co-pending U.S. Appl. No. 17/518,213, inventor Lund; Paul Eugene, filed Nov. 3, 2021.

Co-pending U.S. Appl. No. 17/580,947, inventor Gibbons; Michael, filed Jan. 21, 2022.

Co-pending U.S. Appl. No. 18/046,843, inventor Toh; Mckenzi, filed Oct. 14, 2022.

Co-pending U.S. Appl. No. 18/152,650, inventor Shastry; Shankar, filed Jan. 10, 2023.

Co-pending U.S. Appl. No. 18/392,684, inventors Fernandes; Sunjay Jude et al., filed Dec. 21, 2023.

Co-pending U.S. Appl. No. 18/643,684, inventor Bava; Felice Alessio, filed Apr. 23, 2024.

Co-pending U.S. Appl. No. 18/743,583, inventor Nagendran; Monica, filed Jun. 14, 2024.

Duffy et al., Rapid Protyping of Microfluidic Systems and Polydimethylsiloxane, Anal Chem 70:4974-4984 (1998).

* cited by examiner

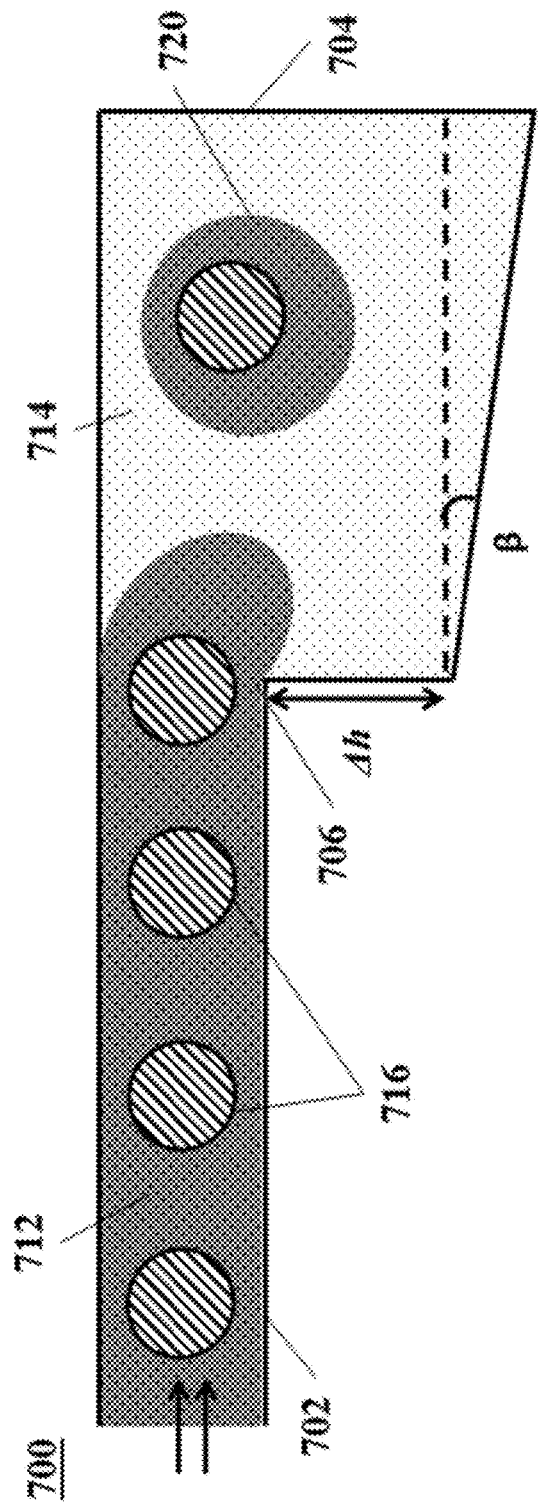
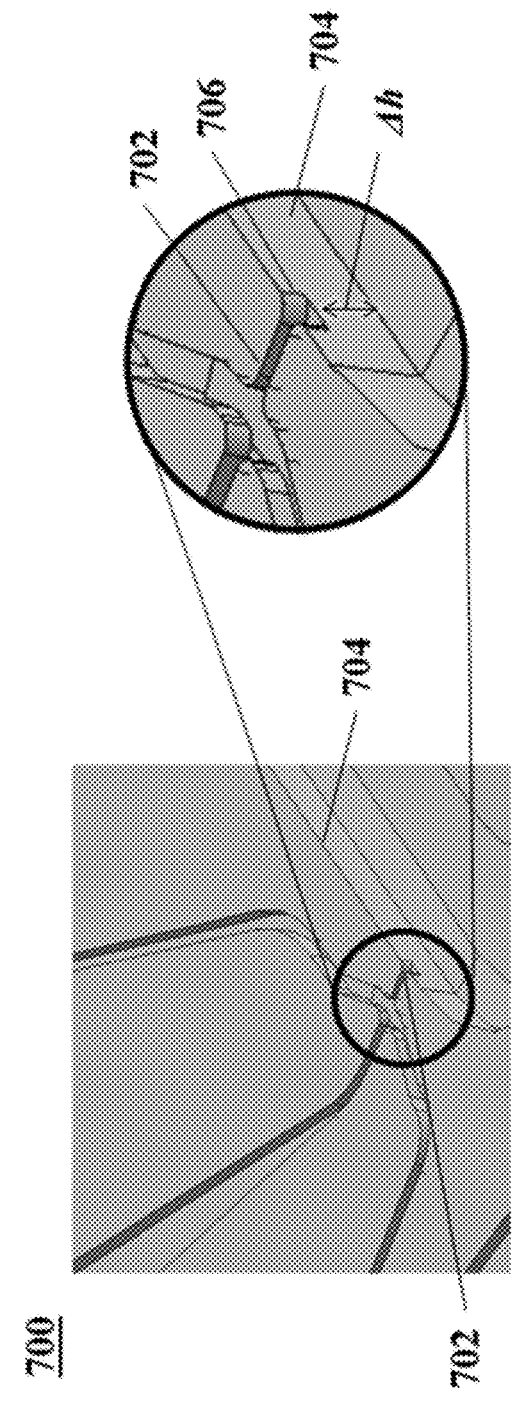
FIG. 7A
FIG. 7B

METHODS AND SYSTEMS FOR SINGLE CELL PROTEIN ANALYSIS

CROSS REFERENCE

This application claims the benefit of U.S. Provisional Patent Application No. 62/897,698, filed Sep. 9, 2019, which is incorporated by reference herein in its entirety for all purposes.

BACKGROUND

A number of techniques have been developed for mapping the abundance of proteins within individual cells, including fluorescence-activated cell sorting (FACS) and mass cytometry (e.g., cytometry by time of flight (CyTOF)). However, these techniques can only provide a measure of the total abundance of a given set of protein targets and are not able to resolve the spatial and physical interactions within a given cell. While a number of techniques have been developed to accomplish this task, including co-immunoprecipitation and fluorescence resonance energy transfer (FRET), these procedures either only work in a bulk setting or have extremely limited resolution and therefore cannot provide information about this activity in single cells. The challenge for combining these two different types of readouts therefore is to incorporate information that enables the resolution of protein interaction events that occur within a single cell.

SUMMARY

The following disclosure provides methods and systems that overcome at least the abovementioned limitations and allow for measuring the abundance and spatial relationships of protein-protein interactions in a single cell context.

In an aspect, provided herein is a method for processing a labelled cell, comprising: (a) partitioning a plurality of labelled cells into a plurality of partitions, wherein a partition comprises a cell barcode molecule and a labelled cell, wherein the labelled cell comprises (i) a first labelling agent to a first protein of the labelled cell, and (ii) a second labelling agent to a second protein of the labelled cell, wherein the first labelling agent comprises a first proximity probe comprising a first barcode sequence, wherein the second labelling agent comprises a second proximity probe comprising a second barcode sequence, and wherein the cell barcode molecule comprises a cell barcode sequence that is complementary to the first and second barcode sequences; (b) generating a barcoded molecule in the partition, wherein the barcoded molecule comprises the first barcode sequence, the second barcode sequence and the cell barcode sequence, or derivatives thereof.

In some embodiments, the first protein is a surface protein. In some embodiments, the second protein is a surface protein. In some embodiments, the first protein is an internal protein. In some embodiments, the second protein is an internal protein. In some embodiments, the second protein is a surface protein. In some embodiments, the first barcode sequence comprises a barcode sequence corresponding to a type of the first labelling agent or a type of the first protein. In some embodiments, the first barcode sequence comprises a unique molecular identifier corresponding to the first labelling agent. In some embodiments, the first labeling agent comprises a feature barcode sequence. In some embodiments, the first labeling agent comprises at least one additional proximity probe. In some embodiments, the additional proximity probe comprises a donor probe comprising a donor sequence and/or an acceptor probe comprising an acceptor sequence. In some embodiments, the donor sequence and the acceptor sequence are different sequences. In some embodiments, the donor sequence and the acceptor sequence are the same sequence. In some embodiments, the first proximity probe is single stranded. In some embodiments, the first proximity probe comprises a donor sequence or an acceptor sequence at an end of the first proximity probe, wherein the cell barcode molecule comprises a first attachment sequence complementary to the donor sequence and a second attachment sequence complementary to the acceptor sequence. In some embodiments, the first attachment sequence and the second attachment sequence flank opposing ends of the cell barcode molecule. In some embodiments, (b) comprises hybridizing the first attachment sequence or the second attachment sequence to the donor sequence or the acceptor sequence, respectively. In some embodiments, the donor sequence and the acceptor sequence are different sequences. In some embodiments, the donor sequence and the acceptor sequence are the same sequence. In some embodiments, the first proximity probe comprises a double stranded portion and a single stranded portion. In some embodiments, the single stranded portion comprises a donor sequence or an acceptor sequence, wherein the cell barcode molecule comprises a first attachment sequence complementary to the donor sequence and a second attachment sequence complementary to the acceptor sequence. In some embodiments, the first attachment sequence and the second attachment sequence flank opposing ends of the cell barcode molecule. In some embodiments, (b) comprises hybridizing the first attachment sequence or the second attachment sequence to the donor sequence or the acceptor sequence, respectively. In some embodiments, the donor sequence and the acceptor sequence are different sequences. In some embodiments, the donor sequence and the acceptor sequence are the same sequence. In some embodiments, the cell barcode molecule comprises a double stranded portion and a single stranded portion. In some embodiments, the cell barcode molecule comprises a first single stranded portion, a double stranded portion, and a second single stranded portion, the first single stranded portion and the second single stranded portion flanking the double stranded portion, wherein the first single stranded portion comprises a first attachment sequence complementary to a donor sequence, and wherein the second single stranded portion comprises a second attachment sequence complementary to an acceptor sequence. In some embodiments, the first proximity probe comprises the acceptor sequence, wherein the second proximity probe comprises the donor sequence, and wherein (b) comprises hybridizing the first attachment sequence to the donor sequence of the second proximity probe and hybridizing the second attachment sequence to the acceptor sequence of the first proximity probe. In some embodiments, the donor sequence and the acceptor sequence are different sequences. In some embodiments, the donor sequence and the acceptor sequence are the same sequence. In some embodiments, the double stranded portion comprises the cell barcode sequence. In some embodiments, the double stranded sequence comprises a unique molecular identifier specific to the cell barcode molecule. In some embodiments, the method further comprises, prior to (b), providing a support comprising the cell barcode molecule attached thereto. In some embodiments, the support comprises a plurality of cell barcode molecules, including the cell barcode molecule, attached thereto. In some embodiments, each of the plurality of cell barcode molecules comprises the cell barcode sequence. In some embodiments, the cell barcode sequence is specific to the support or the cell. In some embodiments, the cell barcode molecule is releasably attached to the support. In some embodiments, one or both of (a) and (b) are performed in a partition. In some embodiments, the partition is a droplet. In some embodiments, the partition is a well. In some embodiments, the method further comprises co-partitioning the cell and a plurality of antibodies, including the first labeling agent and the second labeling agent, in the partition. In some embodiments, the method further comprises co-partitioning the cell and a plurality of cell barcode molecules, including the cell barcode molecule, in the partition. In some embodiments, the cell barcode sequence is specific to the partition. In some embodiments, the first proximity probe comprises a length between 40-80 base pairs (bp). In some embodiments, the first proximity probe comprises a length between 50-60 bp. In some embodiments, the cell barcode molecules comprises a length between 5-40 bp. In some embodiments, the cell barcode molecule comprises a length between 10-20 bp. In some embodiments, the method further comprises sequencing the barcoded molecule or a derivative thereof to generate a sequence associated with the first barcode sequence, the second barcode sequence, and the cell barcode sequence, to determine a relationship between the first protein and the second protein of the cell. In some embodiments, the relationship comprises distribution of the first protein and the second protein in the cell. In some embodiments, the determined relationship comprises interactions between the first protein and the second protein in the cell. In some embodiments, the method further comprises generating a map of relationships between a plurality of proteins of the cell. In some embodiments, the map of relationships comprises relationships between the first protein and the second protein.

In another aspect, disclosed herein is a method for processing proteins of a cell, comprising: (a) providing a plurality of labelled cells, wherein a labelled cell comprises (i) a first labelling agent to a first protein of the labelled cell, and (ii) a second labelling agent to a second protein of the labelled cell, wherein the first labelling agent comprises a first proximity probe comprising a first barcode sequence and wherein the second labelling agent comprises a second proximity probe comprising a second barcode sequence; (b) generating a barcoded molecule from the first proximity probe, the second proximity probe, and a linking molecule, wherein the linking molecule comprises a third barcode sequence that is complementary to the first and second barcode sequences, wherein the barcoded molecule comprises the first barcode sequence, the second barcode sequence and the third barcode sequence, or derivatives thereof.

In some embodiments, the first protein is a surface protein or an internal protein. In some embodiments, the second protein is a surface protein or an internal protein. In some embodiments, the first barcode sequence comprises (i) a barcode sequence corresponding to a type of the first labelling agent or a type of the first protein, and/or (ii) a unique molecular identifier corresponding to the first labelling agent. In some embodiments, the first labeling agent comprises a feature barcode sequence. In some embodiments, the first labeling agent comprises at least one additional proximity probe. In some embodiments, the donor sequence and the acceptor sequence are the same sequence or are different sequences. In some embodiments, the first proximity probe is
(a) single stranded; or (b) single stranded and comprises a donor sequence or an acceptor sequence at an end of the first proximity probe, wherein the linking molecule comprises a first attachment sequence complementary to the donor sequence and a second attachment sequence complementary to the acceptor sequence. In some embodiments, in (a) the first attachment sequence and the second attachment sequence flank opposing ends of the linking molecule; or
(b) wherein the donor sequence and the acceptor sequence are the same sequence or are different sequences. In some embodiments, (b) comprises hybridizing the first attachment sequence or the second attachment sequence to the donor sequence or the acceptor sequence, respectively. In some embodiments, the first proximity probe comprises a double stranded portion and a single stranded portion. In some embodiments, the single stranded portion comprises a donor sequence or an acceptor sequence, wherein the linking molecule comprises a first attachment sequence complementary to the donor sequence and a second attachment sequence complementary to the acceptor sequence. In some embodiments, (a) the first attachment sequence and the second attachment sequence flank opposing ends of the cell barcode molecule; and/or (b) the donor sequence and the acceptor sequence are the same sequence or are different sequences. In some embodiments, (b) comprises hybridizing the first attachment sequence or the second attachment sequence to the donor sequence or the acceptor sequence, respectively. In some embodiments, the linking molecule comprises a double stranded portion and a single stranded portion. In some embodiments, the linking molecule comprises a first single stranded portion, a double stranded portion, and a second single stranded portion, the first single stranded portion and the second single stranded portion flanking the double stranded portion, wherein the first single stranded portion comprises a first attachment sequence complementary to a donor sequence, and wherein the second single stranded portion comprises a second attachment sequence complementary to an acceptor sequence. In some embodiments, the first proximity probe comprises the acceptor sequence, wherein the second proximity probe comprises the donor sequence, and wherein (b) comprises hybridizing the first attachment sequence to the donor sequence of the second proximity probe and hybridizing the second attachment sequence to the acceptor sequence of the first proximity probe. In some embodiments, the donor sequence and the acceptor sequence are the same sequence or are different sequences. In some embodiments, the double stranded portion comprises the third barcode sequence. In some embodiments, the double stranded sequence comprises a unique molecular identifier specific to the third barcode molecule. In some embodiments, the method further comprises, prior to (b), providing a support comprising the linking molecule attached thereto. In some embodiments, wherein the support comprises a plurality of linking molecules, including the cell barcode molecule, attached thereto. In some embodiments, each of the plurality of linking molecules comprises the third barcode sequence. In some embodiments, the third barcode sequence is specific to the support or the cell. In some embodiments, the third barcode molecule is releasably attached to the support. In some embodiments, (b) is performed in a partition. In some embodiments, the partition is a droplet or a well. In some embodiments, the method further comprises co-partitioning (i) the cell and a plurality of antibodies, including the first labeling agent and the second labeling agent, in the partition; or (ii) the cell and a plurality of linking molecules, including the linking molecule, in the partition. In some embodiments, the linking sequence is specific to the partition. In some embodiments, the first proximity probe comprises (i) a length between about 40 to about 80 base pairs (bp); or (ii) a length between about 50 to about 60 bp. In some embodiments, the first proximity probe comprises (i) a length between about 40 to about 80 base pairs (bp); or (ii) a length between about 50 to about 60 bp. In some embodiments, the linking molecule comprises (i) a length between about 5 and about 40 bp; or (ii) a length between about 10 and about 20 bp. In some embodiments, the method further comprises sequencing the barcoded molecule or a derivative thereof to generate a sequence associated with the first barcode sequence, the second barcode sequence, and the third barcode sequence, to determine a relationship between the first protein and the second protein of the cell. In some embodiments, the relationship comprises distribution of the first protein and the second protein in the cell. In some embodiments, the determined relationship comprises interactions between the first protein and the second protein in the cell. In some embodiments, the method further comprises generating a map of relationships between a plurality of proteins of the cell. In some embodiments, the map of relationships comprises relationships between the first protein and the second protein.

In yet another aspect, provided herein is a composition comprising (a) a plurality of labelled cells, wherein a labelled cell comprises (i) a first labelling agent to a first protein of the labelled cell, and (ii) a second labelling agent to a second protein of the labelled cell, wherein the first labelling agent comprises a first proximity probe comprising a first barcode sequence and wherein the second labelling agent comprises a second proximity probe comprising a second barcode sequence; (b) a plurality of cell barcode molecules, wherein a cell barcode molecule comprises a cell barcode sequence that is complementary to the first and second barcode sequences.

In another aspect of the present disclosure, provided herein is a composition comprising a plurality of partitions comprising labelled cells and barcoded molecules, wherein a partition comprises (a) a labelled cell which comprises (i) a first labelling agent to a first protein of the labelled cell, and (ii) a second labelling agent to a second protein of the labelled cell, wherein the first labelling agent comprises a first proximity probe comprising a first barcode sequence, wherein the second labelling agent comprises a second proximity probe comprising a second barcode sequence; and (b) a barcoded molecule which comprises the first barcode sequence, the second barcode sequence and a cell barcode sequence corresponding to the labelled cell, or derivatives thereof.

In another aspect, disclosed herein is a kit comprising (a) a first labelling agent to a first protein of a cell, and (b) a second labelling agent to a second protein of a cell, and (c) a cell barcode molecule comprising a cell barcode sequence, wherein the first labelling agent comprises a first proximity probe comprising a first barcode sequence, wherein the second labelling agent comprises a second proximity probe comprising a second barcode sequence, and wherein the cell barcode sequence is complementary to the first and second barcode sequences.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 7A shows a cross-section view of another example of a microfluidic channel structure with a geometric feature for controlled partitioning. FIG. 7B shows a perspective view of the channel structure of FIG. 7A.

FIGS. 15 A-B depict representative steps of an example processing scheme for mapping protein abundance and interactions in single cells.

DETAILED DESCRIPTION

Figure 1:
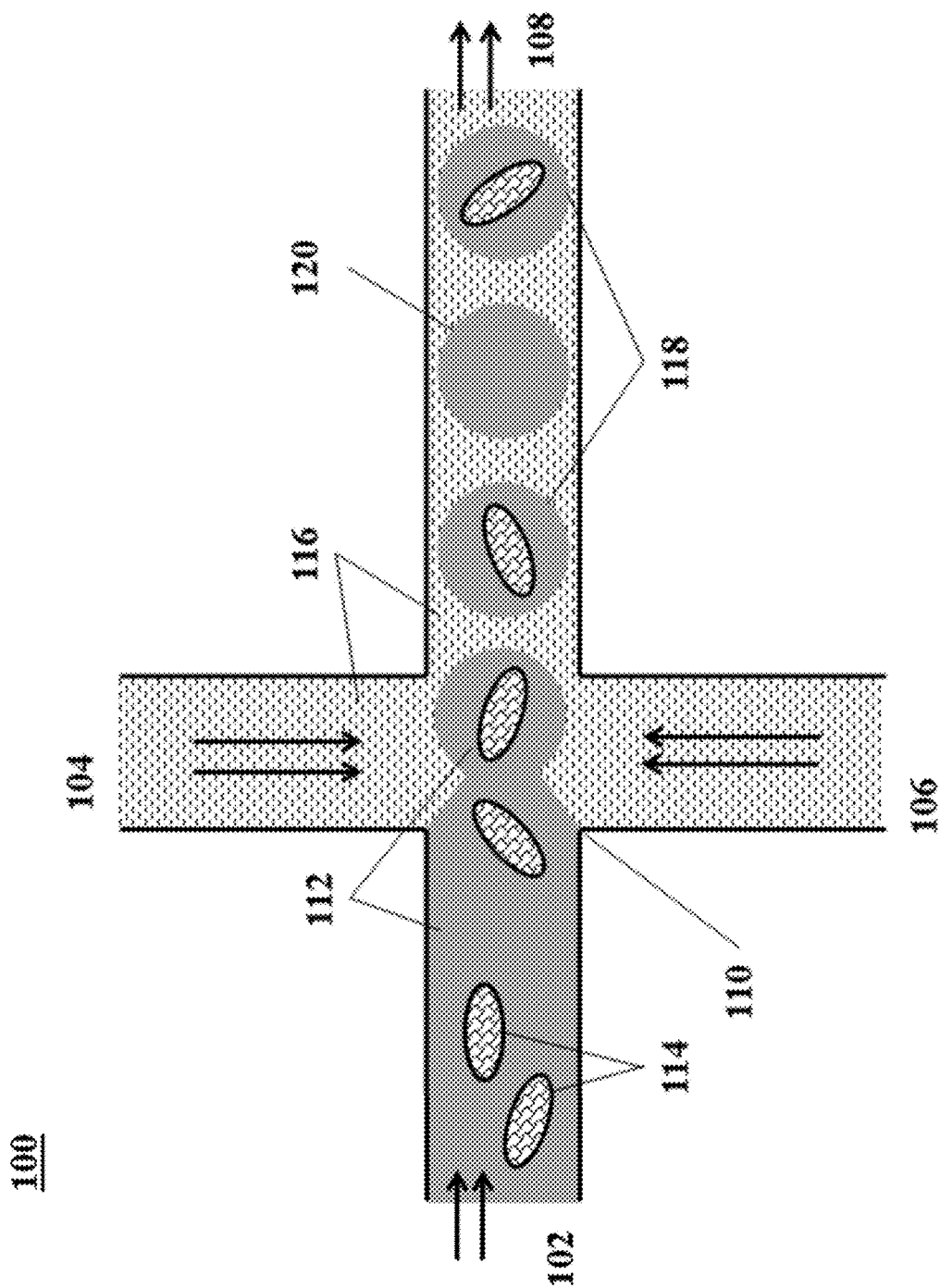
FIG. 1 shows an example of a microfluidic channel structure for partitioning individual analyte carriers.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The terms "a," "an," and "the," as used herein, generally refers to singular and plural references unless the context clearly dictates otherwise.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

The term "real time," as used herein, can refer to a response time of less than about 1 second, a tenth of a second, a hundredth of a second, a millisecond, or less. The response time may be greater than 1 second. In some instances, real time can refer to simultaneous or substantially simultaneous processing, detection or identification.

The term "subject," as used herein, generally refers to an animal, such as a mammal (e.g., human) or avian (e.g., bird), or other organism, such as a plant. For example, the subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses).

The term "genome," as used herein, generally refers to genomic information from a subject, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach, including ligation, hybridization, or other approaches.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "bead," as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Crosslinking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

As used herein, the term "barcoded nucleic acid molecule" generally refers to a nucleic acid molecule that results from, for example, the processing of a nucleic acid barcode molecule with a nucleic acid sequence (e.g., nucleic acid sequence complementary to a nucleic acid primer sequence encompassed by the nucleic acid barcode molecule). The nucleic acid sequence may be a targeted sequence or a non-targeted sequence. For example, in the methods and systems described herein, hybridization and reverse transcription of a nucleic acid molecule (e.g., a messenger RNA (mRNA) molecule) of a cell with a nucleic acid barcode molecule (e.g., a nucleic acid barcode molecule containing a barcode sequence and a nucleic acid primer sequence complementary to a nucleic acid sequence of the mRNA molecule) results in a barcoded nucleic acid molecule that has a sequence corresponding to the nucleic acid sequence of the mRNA and the barcode sequence (or a reverse complement thereof). A barcoded nucleic acid molecule may serve as a template, such as a template polynucleotide, that can be further processed (e.g., amplified) and sequenced to obtain the target nucleic acid sequence. For example, in the methods and systems described herein, a barcoded nucleic acid molecule may be further processed (e.g., amplified) and sequenced to obtain the nucleic acid sequence of the mRNA.

The term "sample," as used herein, generally refers to a biological sample of a subject. The biological sample may comprise any number of macromolecules, for example, cellular macromolecules. The sample may be a cell sample. The sample may be a cell line or cell culture sample. The sample can include one or more cells. The sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "analyte carrier," as used herein, generally refers to a discrete biological system derived from a biological sample. The analyte carrier may be or comprise a biological particle. The analyte carrier may be a macromolecule. The analyte carrier may be a small molecule. The analyte carrier may be a virus. The analyte carrier may be a cell or derivative of a cell. The analyte carrier may be an organelle. The analyte carrier may be a rare cell from a population of cells. The analyte carrier may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The analyte carrier may be a constituent of a cell. The analyte carrier may be or may include DNA, RNA, organelles, proteins, or any combination thereof. The analyte carrier may be or may include a matrix (e.g., a gel or polymer matrix) comprising a cell or one or more constituents from a cell (e.g., cell bead), such as DNA, RNA, organelles, proteins, or any combination thereof, from the cell. The analyte carrier may be obtained from a tissue of a subject. The analyte carrier may be a hardened cell. Such hardened cell may or may not include a cell wall or cell membrane. The analyte carrier may include one or more constituents of a cell but may not include other constituents of the cell. An example of such constituents is a nucleus or an organelle. A cell may be a live cell. The live cell may be capable of being cultured, for example, being cultured when enclosed in a gel or polymer matrix, or cultured when comprising a gel or polymer matrix.

The term "macromolecular constituent," as used herein, generally refers to a macromolecule contained within or from an analyte carrier or biological particle. The macromolecular constituent may comprise a nucleic acid. In some cases, the analyte carrier may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

The term "partition," as used herein, generally, refers to a space or volume that may be suitable to contain one or more species or conduct one or more reactions. A partition may be a physical compartment, such as a droplet or well. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

The term "labelling agent", as used herein generally refers to an agent capable of interacting with some part of a cell including, without limitation, the cell membrane, a molecule on and/or within the cell membrane, an intracellular molecule of the cell, etc. The labelling agent may be configured to couple to an analyte of a cell. The interaction between the agent and some part of the cell may be a covalent interaction or a non-covalent interaction, a reversible interaction, or an irreversible interaction. The labelling agent may be specific to some part of the cell including, without limitation, a biological molecule of the cell (e.g., a polypeptide, a nucleic acid, a lipid, etc.). In some embodiments, the labelling agent may have specificity to a biological target, such as an antibody or an antibody fragment. In some instances, the labelling agent is or comprises an antibody, antibody fragment, or epitope-binding fragment, which may have specificity to a biological molecule of the cell (e.g., a polypeptide, protein, epitope, nucleic acid, lipid, carbohydrate, etc.).

The term "antibody", as used herein generally refers to monoclonal antibodies, polyclonal antibodies, multispecific antibodies (e.g. bispecific antibodies) formed from at least two intact or partial antibodies. In some embodiments, the term "antibody" includes antibody-derived polypeptides, such as single chain variable fragments (scFv), diabodies or other multimeric scFvs, heavy chain antibodies, single domain antibodies, or other polypeptides comprising a sufficient portion of an antibody (e.g., one or more complementarity determining regions (CDRs)) to confer specific antigen binding ability to the polypeptide.

Antibodies are naturally occurring immunoglobulin molecules which have varying structures, all based upon the immunoglobulin fold. For example, IgG antibodies have two "heavy" chains and two "light" chains that are disulfide-bonded to form a functional antibody. Each heavy and light chain itself comprises a "constant" (C) and a "variable" (V) region. The V regions determine the antigen binding specificity of the antibody, whilst the C regions provide structural support and function in non-antigen-specific interactions with immune effectors. The antigen binding specificity of an antibody or antigen-binding fragment of an antibody is the ability of an antibody to specifically bind to a particular antigen.

"Antibody fragments" or "epitope binding fragments", as used herein, generally comprise a portion of an intact antibody, preferably comprising the antigen binding region thereof. Examples of antibody fragments include Fab, Fab', F(ab')2, and Fv fragments; diabodies; tandem diabodies (taDb), linear antibodies (e.g., U.S. Pat. No. 5,641,870, Example 2; Zapata et al., Protein Eng. 8(10):1057-1062 (1995)); one-armed antibodies, single variable domain antibodies, minibodies, single-chain antibody molecules; multispecific antibodies formed from antibody fragments (e.g., including but not limited to, Db-Fc, taDb-Fc, taDb-CH3, (scFV)4-Fc, di-scFv, bi-scFv, or tandem (di,tri)-scFv); and Bi-specific T-cell engagers (BiTEs). In general, the fragments are capable of binding the same epitope as the intact antibody, albeit not necessarily to the same extent. Although multiple types of fragments are possible, an exemplary fragment typically comprises at least one pair of heavy and light chain variable regions (VH and VL, respectively) held together (e.g., by disulfide bonds) to preserve the antigen binding site, and does not contain all or a portion of the Fc region. Fragments of an antibody can be obtained from a given antibody by any suitable technique (e.g., recombinant DNA technology or enzymatic or chemical cleavage of a complete antibody), and typically can be screened for specificity in the same manner in which complete antibodies are screened. In some embodiments, a fragment comprises an $F(ab')_2$ fragment, Fab' fragment, Fab fragment, Fd fragment, or Fv fragment.

Fixed Samples

A sample may be a fixed sample. For example, a sample may comprise a plurality of fixed samples, such as a plurality of fixed cells or fixed nuclei. Alternatively, or in addition to, a sample may comprise a fixed tissue. Fixation of cell or cellular constituent, or a tissue comprising a plurality of cells or nuclei, may comprise application of a chemical species or chemical stimulus. The term "fixed" as used herein with regard to biological samples refers to the state of being preserved from decay and/or degradation. "Fixation" refers to a process that results in a fixed sample, and in some instances can include contacting the biomolecules within a biological sample with a fixative (or fixation reagent) for some amount of time, whereby the fixative results in covalent bonding interactions such as crosslinks between biomolecules in the sample. A "fixed biological sample" refers to a biological sample that has been contacted with a fixation reagent or fixative. For example, a formaldehyde-fixed biological sample has been contacted with the fixation reagent formaldehyde. "Fixed cells" or "fixed tissues" refer to cells or tissues that have been in contact with a fixative under conditions sufficient to allow or result in the formation of intra- and inter-molecular covalent crosslinks between biomolecules in the biological sample. Generally, contact of biological sample (e.g., a cell or nucleus) with a fixation reagent (e.g., paraformaldehyde or PFA) results the formation of intra- and inter-molecular covalent crosslinks between biomolecules in the biological sample. In some cases, the fixation reagent, formaldehyde, is known to result in covalent aminal crosslinks within RNA, DNA, and/or protein molecules. For example, the widely used fixative reagent, paraformaldehyde or PFA, fixes tissue samples by catalyzing crosslink formation between basic amino acids in proteins, such as lysine and glutamine. Both intra-molecular and inter-molecular crosslinks can form in the protein. These crosslinks can preserve protein secondary structure and also eliminate enzymatic activity in the preserved tissue sample. Examples of fixation reagents include but are not limited to aldehyde fixatives (e.g., formaldehyde, also commonly referred to as "paraformaldehyde," "PFA," and "formalin"; glutaraldehyde; etc.), imidoesters, NHS (N-Hydroxysuccinimide) esters, and the like.

In some embodiments, the fixative or fixation reagent useful for fixing samples is formaldehyde. The term "formaldehyde" when used in the context of a fixative also refers "paraformaldehyde" (or "PFA") and "formalin", both of which are terms with specific meanings related to the formaldehyde composition (e.g., formalin is a mixture of formaldehyde and methanol). Thus, a formaldehyde-fixed biological sample may also be referred to as formalin-fixed or PFA-fixed. Protocols and methods for the use of formaldehyde as a fixation reagent to prepare fixed biological samples are well known in the art and can be used in the methods and compositions of the present disclosure. For example, suitable ranges of formaldehyde concentrations for use in preparing a fixed biological sample is 0.1 to 10%, 1-8%, 1-4%, 1-2%, 3-5%, or 3.5-4.5%. In some embodiments of the present disclosure the biological sample is fixed using a final concentration of 1% formaldehyde, 4% formaldehyde, or 10% formaldehyde. Typically, the formaldehyde is diluted from a more concentrated stock solution—e.g., a 35%, 25%, 15%, 10%, 5% PFA stock solution.

Other examples of fixatives include, for example, organic solvents such as alcohols (e.g., methanol or ethanol), ketones (e.g., acetone), and aldehydes (e.g., paraformaldehyde, formaldehyde (e.g., formalin), or glutaraldehyde). As described herein, cross-linking agents may also be used for fixation including, without limitation, disuccinimidyl suberate (DSS), dimethylsuberimidate (DMS), formalin, and dimethyladipimidate (DMA), dithio-bis(-succinimidyl propionate) (DSP), disuccinimidyl tartrate (DST), and ethylene glycol bis(succinimidyl succinate) (EGS). In some cases, a cross-linking agent may be a photocleavable cross-linking agent.

In some cases, more than one fixation reagent can be used in combination in preparing a fixed biological sample. For example, a first fixation agent, such as an organic solvent, may be used in combination with a second fixation agent, such as a cross-linking agent. The organic solvent may be an alcohol (e.g., ethanol or methanol), ketone (e.g., acetone), or aldehyde (e.g., paraformaldehyde, formaldehyde, or glutaraldehyde). The cross-linking agent may be selected from the group consisting of disuccinimidyl suberate (DSS), dimethylsuberimidate (DMS), formalin, and dimethyladipimidate (DMA), dithio-bis(-succinimidyl propionate) (DSP), disuccinimidyl tartrate (DST), and ethylene glycol bis(succinimidyl succinate) (EGS). In some cases, a first fixation agent may be provided to or brought into contact with the cell to bring about a change in a first characteristic or set of characteristics of the cell, and a fixation agent may be provided to or brought into contact with the cell to bring about a change in a second characteristic or set of characteristics of the cell. For example, a first fixation agent may be provided to or brought into contact with a cell to bring about a change in a dimension of the cell (e.g., a reduction in cross-sectional diameter, see US 20200033237, which is incorporated herein by reference in its entirety), and a second fixation agent may be provided to or brought into contact with a cell to bring about a change in a second characteristic or set of characteristics of the cell (e.g., forming crosslinks within and/or surrounding the cell). The first and second fixation agents may be provided to or brought into contact with the cell at the same or different times.

In an example, a first fixation agent that is an organic solvent may be provided to a cell to change a first characteristic (e.g., cell size) and a second fixation agent that is a cross-linking agent may be provided to a cell to change a second characteristic (e.g., cell fluidity or rigidity). The first fixation agent may be provided to the cell before the second fixation agent.

In another embodiment, biomolecules (e.g., biological samples such as tissue specimens) are contacted with a fixation reagent containing both formaldehyde and glutaraldehyde, and thus the contacted biomolecules can include fixation crosslinks resulting both from formaldehyde induced fixation and glutaraldehyde induced fixation. Typically, a suitable concentration of glutaraldehyde for use as a fixation reagent is 0.1 to 1%.

Changes to a characteristic or a set of characteristics of a cell or cellular constituents (e.g., incurred upon interaction with one or more fixation agents) may be at least partially reversible (e.g., via rehydration or de-crosslinking). Alternatively, changes to a characteristic or set of characteristics of a cell or cellular constituents (e.g., incurred upon interaction with one or more fixation agents) may be substantially irreversible.

A sample (e.g., a cell sample) may be subjected to a fixation process at any useful point in time. For example, cells and/or cellular constituents of a sample may be subjected to a fixation process involving one or more fixation agents (e.g., as described herein) prior to commencement of any subsequent processing, such as for storage. Cells and/or cellular constituents, such as cells and/or cellular constituents of a tissue sample, subjected to a fixation process prior to storage, may be stored in an aqueous solution, optionally in combination with one or more preserving agents configured to preserve morphology, size, or other features of the cells and/or cellular components. Fixed cells and/or cellular constituents may be stored below room temperature, such as in a freezer. Alternatively, cells and/or cellular constituents of a sample may be subjected to a fixation process involving one or more fixation agents subsequent to one or more other processes, such as filtration, centrifugation, agitation, selective precipitation, purification, permeabilization, isolation, heating, etc. For example, cells, nuclei, and/or cellular constituents of a given type from a sample may be subjected to a fixation process following a separation and/or enrichment procedure (e.g., as described herein). In an example, a sample comprising a plurality of cells including a plurality of cells of a given type may be subjected to a positive separation process to provide a sample enriched in the plurality of cells of the given type. The enriched sample may then be subjected to a fixation process involving one or more fixation agents (e.g., as described herein) to provide an enriched sample comprising a plurality of fixed cells. A fixation process may be performed in a bulk solution. In some cases, fixed samples (e.g., fixed cells, fixed nuclei, and/or cellular constituents) may be partitioned amongst a plurality of partitions (e.g., droplets or wells) and subjected to processing as described elsewhere herein. In some cases, fixed samples may undergo additional processing, such as partial or complete reversal of a fixation process by, for example, rehydration or de-crosslinking, prior to partitioning and any subsequent processing. In some cases, fixed samples may undergo partial or complete reversal of a fixation process within a plurality of partitions (e.g., prior to or concurrent with additional processing described elsewhere herein).

In some cases, a tissue specimen comprising a plurality of cells and/or cellular constituents may be processed to provide formalin-fixed paraffin-embedded (FFPE) tissue. A tissue specimen may be contacted (e.g., saturated) with formalin and then embedded in paraffin wax. FFPE processing may facilitate preservation of a tissue sample (e.g., prior to subsequent processing and analysis). A tissue sample, including an FFPE tissue sample, may also or alternatively be subjected to storage in a low-temperature freezer. Cells and/or cellular constituents may be dissociated from a tissue sample (e.g., FFPE tissue sample) prior to undergoing subsequent processing. In some cases, individual cells and/or cellular constituents of a tissue sample such as an FFPE tissue sample may be optically detected, labeled, or otherwise processed prior to any such dissociation. Such detection, labeling, or other processing may be performed according to a 2- or 3-dimensional array and optionally according to a pre-determined pattern.

Methods for Processing Proteins in a Single Cell

The disclosure herein provides methods for the detection of protein-protein interactions within a single cell context. In some cases, the methods provide for measuring the abundance of protein-protein interactions in a single cell context. In some cases, the methods provide for determining a relationship between proteins in a single cell context (e.g., a spatial relationship). Generally, the methods provided herein involve the use of a proximity-ligation approach to physically link information regarding protein-protein interactions which can be read using traditional sequencing methods. In some cases, this information may be used to identify protein-protein interactions within a single cell. Additionally or alternatively, this information may be used to determine a spatial relationship of proteins within a single cell. Advantageously, the methods described herein may be used to analyze a plurality of different protein-protein interactions simultaneously (e.g., multiplexing). Additionally, the methods described herein may maintain spatial relationship information, which would normally be lost using traditional methods.

Methods are provided for processing proteins in a cell. In some cases, the methods comprise: (a) attaching (i) a first labelling agent (e.g., protein binding agent such as an antibody) to a first protein of the cell, and (ii) a second labelling agent (e.g., antibody) to a second protein of the cell, wherein the first labelling agent comprises a first proximity probe comprising a first barcode sequence, and wherein the second labelling agent comprises a second proximity probe comprising a second barcode sequence; (b) attaching a synthetic oligonucleotide molecule with the first proximity probe and the second proximity probe to generate a barcoded molecule, wherein the synthetic oligonucleotide molecule comprises a common barcode sequence; and (c) sequencing the barcoded molecule or a derivative thereof to generate a sequence associated with the first barcode sequence, the second barcode sequence, and the common barcode sequence, to determine a relationship between the first protein and the second protein of the cell.

In various aspects, the methods involve attaching a first labelling agent (e.g., protein binding agent such as an antibody) to a first protein of a cell. The first labelling agent (e.g., antibody) may be incubated or otherwise contacted with the cell under conditions that enable the first labelling agent to bind to the first protein. In some cases, the first protein may be a cell-surface protein (e.g., a cell-surface receptor). In some cases, the first protein may be an intracellular or an internal protein. In some cases, the first protein may be a protein associated with a subcellular organelle or a subcellular compartment. For example, the first protein may be a protein associated with the nuclear envelope, the endoplasmic reticulum (ER), the mitochondria, and the like. In some instances, the first labelling agent (e.g., antibody) selectively binds to the first protein.

In various aspects, the first labelling agent may be coupled to a first proximity probe. In some cases, the first proximity probe may be an oligonucleotide. In some cases, the oligonucleotide may be a single-stranded oligonucleotide. In other cases, the oligonucleotide may be a double-stranded oligonucleotide. In some cases, the double-stranded oligonucleotide may comprise a single-stranded overhang. In some cases, the single-stranded overhang may be complementary to a single-stranded portion of a different oligonucleotide (e.g., a synthetic oligonucleotide probe or splint oligonucleotide, as further described herein). In some cases, the first proximity probe may comprise a first barcode sequence. The first barcode sequence may comprise a labelling agent-specific (e.g., an antibody specific) barcode sequence that is specific to a type of the first labelling agent or to a type of the first protein. For example, the first labelling agent may be a first antibody (A) that selectively binds to a first protein (W) which may be coupled to a first proximity probe that comprises a first barcode sequence that corresponds to the first antibody (A) or the first protein (W). Similarly, a first antibody (B) that selectively binds to a first protein (X) may be coupled to a first proximity probe that comprises a first barcode sequence that corresponds to the first antibody (B) or the first protein (X). In some examples, each different type of first antibody (e.g., that bind to different target proteins) are coupled to a first proximity probe comprising a first barcode sequence unique for each type of first antibody. Generally, each individual first antibody molecule may be coupled to a plurality of first proximity probes, each having the same first barcode sequence. In such cases, a plurality of different types of first antibodies, each coupled to a unique first barcode sequence, and each capable of binding to a different protein target, may be used. The identity of the first protein may then be indirectly ascertained by identifying the first barcode sequence in a downstream process (e.g., by sequencing). Labeling each first antibody with a different first barcode sequence may provide for the analysis of multiple different protein-protein interactions in the same sample (or cell).

In various aspects, the first proximity probe may further comprise a donor probe or an acceptor probe. In some cases, the donor probe may comprise a donor sequence. In some cases, the donor sequence may be a single-stranded oligonucleotide sequence. In some cases, the first proximity probe may comprise a double-stranded oligonucleotide with a single-stranded overhang at a terminal end. In such cases, the donor sequence may include the single-stranded overhang, or a portion thereof. In some cases, the donor probe may be positioned at the 5' terminal end or the 3' terminal end of the first proximity probe. In some cases, the donor sequence may be complementary (or partially complementary) to an oligonucleotide sequence found on a different oligonucleotide molecule. For example, in some cases, the donor sequence may be complementary to a first attachment sequence located on a synthetic oligonucleotide molecule (or splint oligonucleotide). In some cases, the acceptor probe may comprise an acceptor sequence. In some cases, the acceptor sequence may be a single-stranded oligonucleotide sequence. In some cases, the first proximity probe may comprise a double-stranded oligonucleotide with a single-stranded overhang at a terminal end. In such cases, the acceptor sequence may include the single-stranded overhang, or a portion thereof. In some cases, the acceptor probe may be positioned at the 5' terminal end or the 3' terminal end of the first proximity probe. In some cases, the acceptor sequence may be complementary (or partially complementary) to an oligonucleotide sequence found on a different oligonucleotide molecule. For example, in some cases, the acceptor sequence may be complementary to a second attachment sequence located on a synthetic oligonucleotide molecule (or splint oligonucleotide). In some cases, the donor sequence and the acceptor sequence may be different oligonucleotide sequences. In some cases, the donor sequence and the acceptor sequence may be the same oligonucleotide sequence. In some cases, each individual first antibody molecule may comprise a plurality of first proximity probes, with some of the plurality of first proximity probes having a donor probe, and some of the plurality of first proximity probes having an acceptor probe.

In various aspects, the first proximity probe may further comprise a unique molecular index (UMI) sequence. In some cases, the UMI may be specific to an individual first labelling agent (e.g., antibody molecule). In some cases, each individual first labelling agent (e.g., antibody molecule) may be coupled to a plurality of first proximity probes, wherein each of the plurality of first proximity probes comprises a UMI. Preferentially, each first proximity probe coupled to an individual first labelling agent (e.g., antibody molecule) comprises the same UMI sequence. In some cases, each individual labelling agent (e.g., antibody molecule) of a plurality of first labelling agents comprises a different UMI sequence. For example, a plurality of first antibody molecules may comprise 1000 individual antibody molecules, each capable of selectively binding to the same protein target. Each of the 1000 individual antibody molecules may be coupled to a plurality of first proximity probes. Each of the plurality of first proximity probes may comprise a first barcode sequence that corresponds to the type of first antibody, such that the plurality of first antibodies are coupled to the same first barcode sequence. Each of the plurality of first proximity probes may further comprise a UMI sequence, such that each of the 1000 individual antibody molecules have a different UMI sequence. Thus, in this example, 1000 UMI sequences could be used to individually label each individual first antibody molecule. The identity of the individual first antibody molecule may be indirectly ascertained by identifying the UMI in a downstream process (e.g., by sequencing).

In various aspects, the first proximity probe may further comprise one or more additional features. In some cases, the first proximity probe may comprise a feature barcode. In some cases, the first proximity probe may comprise one or more sequencing adapters suitable for a downstream sequencing platform (e.g., P5 and/or P7 for Illumina-based sequencing platforms), one or more functional sequences, e.g., primer sequences (e.g., sequencing primer sequences, e.g., R1 and/or R2 for Illumina-based sequencing platforms or partial sequencing primer sequences) or additional barcodes, adapters, tags, and combinations thereof.

In various aspects, the first proximity probe may comprise a length. In some cases, the first proximity probe may comprise a length of from 40 to 80 nucleotides (and/or base pairs). For example, the first proximity probe may comprise a length of 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides (and/or base pairs). In particular aspects, the first proximity probe may comprise a length of from 50 to 60 nucleotides (and/or base pairs). In some cases, the length of the first proximity probe may be selected based on, e.g., a scope of a relationship (e.g., a spatial relationship) of a first protein and a second protein. For example, the length of the first proximity probe may be selected based on the distance of a first protein to a second protein within or adjacent to a cell. In some cases, the length of the first proximity probe may be selected based on a desired radius of survey around the first protein in the cell. For example, a shorter first proximity probe will have a smaller radius of survey and therefore will only be able to investigate the relationship of proteins that are close to the first protein. Similarly, a longer first proximity probe will have a larger radius of survey and will be able to investigate the spatial relationship of proteins that are further from the first protein. Thus, by varying the length of the first proximity probe, the scope of investigation can be adjusted.

In various aspects, the methods involve attaching a second labelling agent (e.g., antibody, antibody molecule, antibody fragment, epitope-binding fragment) to a second protein of a cell. The second labelling agent (e.g., antibody) may be incubated or otherwise contacted with the cell and allowed to bind to the second protein. In some cases, the second protein may be a cell-surface protein (e.g., a cell-surface receptor). In some cases, the second protein may be an intracellular or an internal protein. In some cases, the second protein may be a protein associated with a subcellular organelle or compartment. For example, the second protein may be a protein associated with the nuclear envelope, the endoplasmic reticulum (ER), the mitochondria, the Golgi apparatus, the cytoskeleton, the lysosome, the centriole, the vacuole, and the like. Preferentially, the second labelling agent (e.g., antibody) selectively binds to the second protein.

In various aspects, the second labelling agent may be coupled to a second proximity probe. In some cases, the second proximity probe may be an oligonucleotide. In some cases, the oligonucleotide may be a single-stranded oligonucleotide. In other cases, the oligonucleotide may be a double-stranded oligonucleotide. In some cases, the double-stranded oligonucleotide may comprise a single-stranded overhang. In some cases, the single-stranded overhang may be complementary to a single-stranded portion of a different oligonucleotide (e.g., a synthetic oligonucleotide probe). In some cases, the second proximity probe may comprise a second barcode sequence. The second barcode sequence may comprise a labelling agent-specific (e.g., an antibody specific) barcode sequence that is specific to a type of the second labelling agent (e.g., antibody) or to a type of the second protein. For example, a second antibody (C) that selectively binds to a first protein (Y) may be coupled to a second proximity probe that comprises a second barcode sequence that corresponds to the second antibody (C) or the second protein (Y). Similarly, a second antibody (D) that selectively binds to a second protein (Z) may be coupled to a second proximity probe that comprises a second barcode sequence that corresponds to the second antibody (D) or the second protein (Z). Preferentially, each different type of second antibody (e.g., that bind to different target proteins) is coupled to a second proximity probe comprising a second barcode sequence unique for each type of second antibody. Generally, each individual second antibody molecule may be coupled to a plurality of second proximity probes, each having the same second barcode sequence. In such cases, a plurality of different types of second antibodies, each coupled to a unique second barcode sequence, and each capable of binding to a different protein target, may be used. The identity of the second protein may then be indirectly ascertained by identifying the second barcode sequence in a downstream process (e.g., by sequencing). Labeling each second antibody with a different second barcode sequence provides for the analysis of multiple different protein-protein interactions in the same sample.

In various aspects, the second proximity probe may further comprise a donor probe or an acceptor probe. In some cases, the donor probe may comprise a donor sequence. In some cases, the donor sequence may be a single-stranded oligonucleotide sequence. In some cases, the second proximity probe may comprise a double-stranded oligonucleotide with a single-stranded overhang at a terminal end. In such cases, the donor sequence may include the single-stranded overhang, or a portion thereof. In some cases, the donor probe may be positioned at the 5' terminal end or the 3' terminal end of the first proximity probe. In some cases, the donor sequence may be complementary (or partially complementary) to an oligonucleotide sequence found on a different oligonucleotide molecule. For example, in some cases, the donor sequence may be complementary to a first attachment sequence located on a synthetic oligonucleotide molecule (or splint oligonucleotide). In some cases, the acceptor probe may comprise an acceptor sequence. In some cases, the acceptor oligonucleotide sequence may be a single-stranded oligonucleotide sequence. In some cases, the first proximity probe may comprise a double-stranded oligonucleotide with a single-stranded overhang at a terminal end. In such cases, the acceptor sequence may include the single-stranded overhang, or a portion thereof. In some cases, the acceptor probe may be positioned at the 5' terminal end or the 3' terminal end of the second proximity probe. In some cases, the acceptor sequence may be complementary (or partially complementary) to an oligonucleotide sequence found on a different oligonucleotide molecule. For example, in some cases, the acceptor sequence may be complementary to a second attachment sequence located on a synthetic oligonucleotide molecule (or splint oligonucleotide). In some cases, the donor sequence and the acceptor sequence may be different oligonucleotide sequences. In some cases, the donor sequence and the acceptor sequence may be the same oligonucleotide sequence. In some cases, each individual second labelling agent (e.g., antibody molecule) may comprise a plurality of second proximity probes, with some of the plurality of second proximity probes having a donor probe, and some of the plurality of second proximity probes having an acceptor probe.

In various aspects, the second proximity probe may comprise, in addition to a second barcode sequence, one or more suitable features. For example, in some cases, the second proximity probe may comprise a unique molecular index (UMI) sequence. In some cases, the UMI may be specific to an individual second labelling agent (e.g., antibody molecule). In some cases, each individual second labelling agent (e.g., antibody molecule) may be coupled to a plurality of second proximity probes, wherein each of the plurality of second proximity probes comprises a UMI. Preferentially, each second proximity probe coupled to an individual second labelling agent molecule comprises the same UMI sequence. In some cases, each individual labelling agent (e.g., antibody molecule) of a plurality of second labelling agents (e.g., antibody molecules) comprises a different UMI sequence. For example, a plurality of second antibody molecules may comprise 1000 individual antibody molecules, each capable of selectively binding to the same protein target. Each of the 1000 individual antibody molecules may be coupled to a plurality of second proximity probes. Each of the plurality of second proximity probes may comprise a second barcode sequence that corresponds to the type of second antibody, such that the plurality of second antibodies are coupled to the same second barcode sequence. Each of the plurality of second proximity probes may further comprise a UMI sequence. Each of the 1000 individual antibody molecules may be coupled to a plurality of second proximity probes, each of the 1000 individual antibody molecules having a different UMI sequence. Thus, in this example, 1000 different UMI sequences could be used to individually label each second antibody molecule. The identity of the individual second antibody molecule may be indirectly ascertained by identifying the UMI in a downstream process (e.g., by sequencing).

In various aspects, the second proximity probe may further comprise one or more suitable features. In some cases, the second proximity probe may comprise a feature barcode. In some cases, the second proximity probe may comprise one or more sequencing adapters suitable for a downstream sequencing platform (e.g., P5 and/or P7 for Illumina-based sequencing platforms), one or more functional sequences, e.g., primer sequences (e.g., sequencing primer sequences, e.g., R1 and/or R2 for Illumina-based sequencing platforms or partial sequencing primer sequences), or additional barcodes, adapters, tags, and combinations thereof.

In various aspects, the second proximity probe may comprise a length. In some cases, the second proximity probe may comprise a length of from 40 to 80 nucleotides (and/or base pairs). For example, the second proximity probe may comprise a length of 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides (and/or base pairs). In particular aspects, the second proximity probe may comprise a length of from 50 to 60 nucleotides (and/or base pairs). In some cases, the length of the second proximity probe may be selected based on, e.g., a scope of a relationship (e.g., a spatial relationship) of a first protein and a second protein. For example, the length of the second proximity probe may be selected based on the distance of a first protein to a second protein within a cell. In some cases, the length of the second proximity probe may be selected based on a desired radius of survey around the second protein in the cell. For example, a shorter second proximity probe will have a smaller radius of survey and therefore will only be able to investigate the relationship of proteins that are close to the second protein. Similarly, a longer second proximity probe will have a larger radius of survey and will be able to investigate the spatial relationship of proteins that are further from the second protein. Thus, by varying the length of the second proximity probe, the scope of investigation can be adjusted.

In some cases, the cell may be processed prior to attaching the first labelling agent (e.g., antibody) to the first protein, and/or the second labelling agent (e.g., antibody) to the second protein. For example, in some cases, the cell may be fixed (e.g., by treating with a fixative reagent) and/or permeabilized prior to attaching the first labelling agent to the first protein and/or the second labelling agent to the second protein. In such cases where an intracellular protein is investigated, the cell may be permeabilized prior to attaching the first labelling agent to the first protein, and/or the second labelling agent to the second protein. Cells may be permeabilized by any suitable methods, including, but not limited to, treatment with a permeabilization agent (e.g., saponin, Triton X-100, Tween-20, and the like) or by sonication. In some cases, the cell may be fixed and/or permeabilized prior to attaching labelling agents (e.g., antibodies) to proteins.

In various aspects, the method further comprises attaching a synthetic oligonucleotide molecule (a splint oligonucleotide) with the first proximity probe and the second proximity probe to generate a barcoded molecule. In some cases, the synthetic oligonucleotide molecule comprises a single-stranded oligonucleotide. In some cases, the synthetic oligonucleotide molecule comprises a double-stranded oligonucleotide, with a single-stranded overhang at both ends. In some cases, the synthetic oligonucleotide molecule comprises a first attachment sequence at a first end, which is capable of hybridizing to a sequence located at the end of the first proximity probe (e.g., a donor sequence). In some cases, the synthetic oligonucleotide molecule further comprises a second attachment sequence at a second end, which is capable of hybridizing to a sequence located at the end of the second proximity probe (e.g., an acceptor sequence). Generally, the first attachment sequence is complementary to the donor sequence, and the second attachment sequence is complementary to the acceptor sequence. In some cases, the synthetic oligonucleotide molecule may be attached to the first proximity probe and the second proximity probe by ligation. In other cases, the synthetic oligonucleotide molecule may be attached to the first proximity probe and the second proximity probe by extension (e.g., using a polymerase enzyme). In some instances, the first attachment sequence may hybridize to a donor sequence (on a first proximity probe) coupled to an individual labelling agent (e.g., antibody molecule), and the second attachment sequence may hybridize to an acceptor sequence (on a second proximity probe) coupled to the same individual labelling agent (e.g., antibody molecule). This approach may be used to investigate intra-labelling agent (e.g., intra-antibody) interactions. Additionally or alternatively, the first attachment sequence may hybridize to a donor sequence (on a first proximity probe) coupled to a first labelling agent (e.g., antibody molecule), and the second attachment sequence may hybridize to an acceptor sequence (on a second proximity probe) coupled to a second labelling agent (e.g., antibody molecule), thereby linking the first and second labelling agents together. This approach may be used to investigate inter-labelling agent interactions, such as inter-antibody interactions. In some cases, the synthetic oligonucleotide molecule may further comprise a common barcode sequence. In some cases, the common barcode sequence may be a cell barcode or a droplet barcode as described herein. In some cases, the double-stranded portion of the synthetic oligonucleotide molecule comprises the common barcode sequence. In some cases, the synthetic oligonucleotide molecule may further comprise a UMI. In some cases, the UMI is specific for the individual synthetic oligonucleotide molecule.

In various aspects, the synthetic oligonucleotide molecule may have a length. In some cases, the length may be from 5 to 40 nucleotides (and/or base pairs). For example, the length of the synthetic oligonucleotide molecule may be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides (and/or base pairs). In particular aspects, the length of the synthetic oligonucleotide molecule may be from 10 to 20 nucleotides (and/or base pairs).

In various aspects, the methods further comprise sequencing the barcoded molecule (or a derivative thereof) to generate a sequence associated with the first barcode sequence, the second barcode sequence, and the common barcode sequence. In some cases, the methods may further comprise determining a relationship between the first protein and the second protein based on the sequencing information. For example, the sequencing information may indicate a spatial relationship between the first protein and the second protein within the cell.

In various non-limiting aspects, any of the methods may be performed in a partition. In some cases, a plurality of cells may be partitioned into a plurality of partitions, such that each one of the plurality of partitions contains, on average, a single cell. In some cases, the cells may be partitioned prior to attaching the first labelling agent (e.g., antibody) to the first protein and/or the second labelling agent (e.g., antibody) to the second protein. In other cases, the cells may be partitioned after attaching the first labelling agent (e.g., antibody) to the first protein and/or the second labelling agent (e.g., antibody) to the second protein. For example, a first antibody and/or a second antibody may be introduced into a partition comprising a single cell (or co-partitioned with a single cell) and incubated under conditions suitable to allow the first antibody to bind to the first protein and the second antibody to bind to the second protein. In both cases, the synthetic oligonucleotide molecule may be introduced into the partition, for example, by co-partitioning the synthetic oligonucleotide molecule with a single cell into a partition.

The partition may be a droplet emulsion or a well. In some cases, each partition may comprise, on average, a single cell. Each partition may further comprise a single substrate coated with a plurality of synthetic oligonucleotide molecules. In some cases, the substrate may be a particle (e.g., a bead or gel bead). Each of the plurality of synthetic oligonucleotide molecules may be attached to the surface of the substrate. In some cases, each of the plurality of synthetic oligonucleotide molecules may be releasably attached to the surface of the substrate. Each of the plurality of synthetic oligonucleotide molecules may comprise a cell barcode. A cell barcode may be a nucleic acid sequence that, when sequenced and identified, provides information as to the cell source of the sequenced molecule. Each cell barcode coupled to an individual substrate may be the same cell barcode, such that, when the synthetic oligonucleotide molecule is coupled to the first proximity probe and the second proximity probe, the cell barcode labels each resulting barcoded molecule as being from the same cell. Each of the synthetic oligonucleotide molecules may further comprise a UMI. Each UMI coupled to a single substrate may be different, such that, when the synthetic oligonucleotide molecule is coupled to the first proximity probe and the second proximity probe, the UMI labels each resulting barcoded molecule as a unique molecule. In downstream processes (e.g., a sequencing reaction), the cell or partition from which the barcoded molecule is obtained may be indirectly ascertained (e.g., by reading the cell barcode), thereby linking the protein-protein interaction information with a single cell. Similarly, the UMI labels may be used for quantification of such protein-protein interactions for a single cell.

In various aspects, the methods may further comprise generating a map of relationships between a plurality of proteins within a cell. In some cases, the map of relationships may comprise a relationship (e.g., a spatial relationship) between a first protein and a second protein. In some cases, a map of relationships may be generated for a single cell. In some cases, the map of relationships may comprise relationship information related to at least 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000 or more different proteins.

Figure 15A:
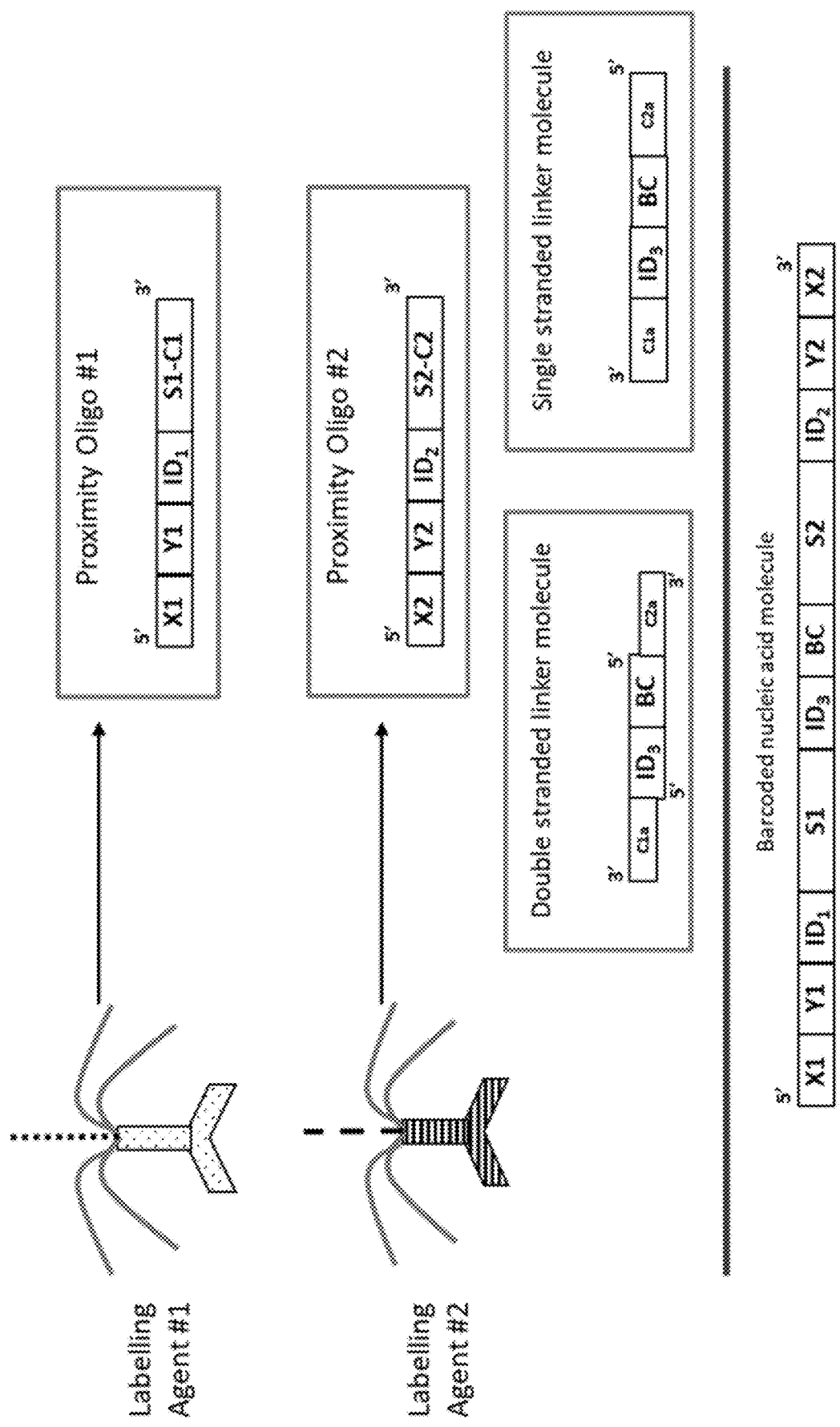
FIG. 15A shows an example processing scheme.
Figure 15B:
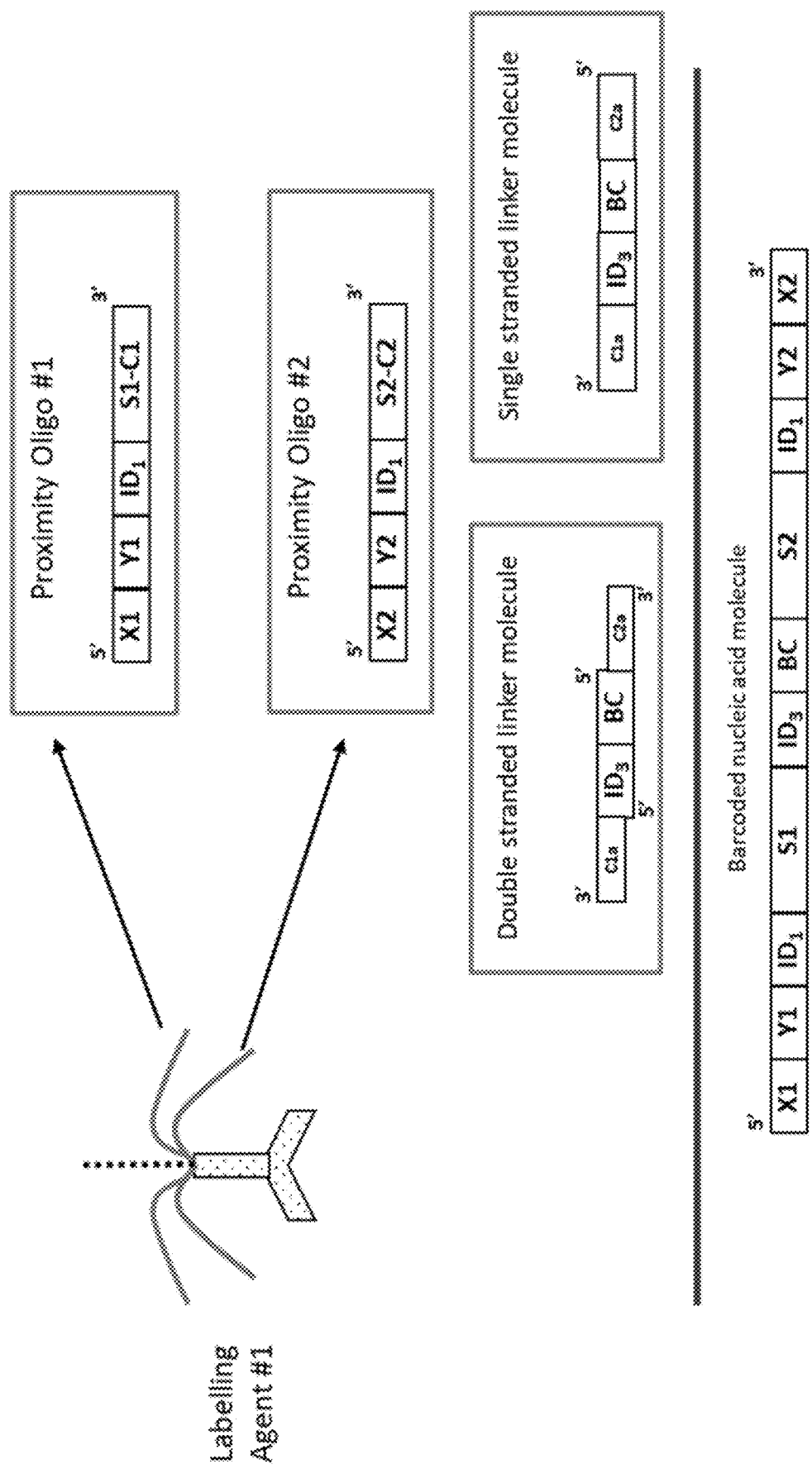
FIG. 15B shows another example processing scheme.

FIGS. 15A-B depict non-limiting examples of the methods described herein. FIGS. 15A-B show at least one Labelling Agent (e.g., #1, #2), which correspond to labelling agents for analyte carriers (e.g., cells). In one embodiment, the labelling agent is capable of or configured to couple (or specifically bind) to an analyte of a cell. In some instances, the analyte is a macromolecular constituent, such as a peptide, polypeptide, or protein. The protein may be a cell-surface protein (such as a cell-surface receptor), an intracellular protein, a protein associated with an intracellular organelle or compartment, or any combination thereof.

In some instances, the labelling agent is a protein binding agent, such as an antibody, antibody fragment, or epitope binding fragment. In FIG. 15A, Labelling Agent #1 and #2 include a component for binding or labelling an analyte carrier (depicted as a "Y" shape) and a plurality of proximity oligonucleotides (depicted as curved lines). In one embodiment, the proximity oligonucleotide comprises a number of elements including (i) a unique identifier sequence shown as $ID_1$ or $ID_2$ and (ii) an element having a sequence specific to the labelling agent (S1 or S2) and a sequence configured to couple to (e.g., capture or hybridize) a sequence of a linker molecule (C1 or C2). This element (ii) is depicted as S1-C1 or S2-C2 in FIG. 15A. The unique identifier sequence may be a unique molecular index or identifier (UMI) as described herein. In one embodiment, the unique identifier sequence corresponds to a specific labelling agent. The proximity oligo nucleotides may optionally include additional functional elements or sequences (depicted a X1, Y1, X2, and Y2) for downstream processing, e.g., sequencing reaction. In one embodiment, the additional functional elements may include, without limitation, any suitable adapters, primer sequences (e.g., primers, sequencing primer sequences, partial sequencing primer sequences, etc.), barcodes, tags, and the like as further described herein.

As shown in FIG. 15A, a labelling agent (e.g., Labelling Agent #1 or #2) may comprise a plurality of proximity oligonucleotides (depicted as curved lines), which comprise nucleic acid sequences. In one embodiment, the plurality of proximity oligonucleotides comprises identical nucleic acid sequences, or a subset of said plurality of proximity oligonucleotides comprises identical nucleic acid sequences. In another embodiment, the plurality of proximity oligonucleotides, or a subset thereof, of a labelling agent (e.g., Labelling Agent #1) comprises identical nucleic acid sequences that are different than nucleic acid sequences from another plurality of proximity oligonucleotides, or a subset thereof, from another labelling agent (e.g., Labelling Agent #2). FIG. 15A also shows linker molecules for the creation of a barcoded nucleic acid molecule comprising sequences from proximity oligonucleotides (e.g., Proximity Oligo #1 and #2). The linker molecules may be single-stranded or double-stranded (optionally with single-stranded overhangs) nucleic acid molecules. In either case, the linker molecule is configured to couple to elements of at least two proximity oligonucleotides (e.g., C1 and C2) to bring them close enough for a nucleic acid reaction involving the proximity oligonucleotides and the linker molecule. The linker molecule comprises (i) a sequence C1a configured to couple to sequence C1 and (ii) a sequence C2a configured to couple to sequence C2. In another embodiment, the linker molecule further comprises a nucleic acid barcode sequence (e.g., depicted as BC) corresponding to the cell to be analyzed. This nucleic acid barcode sequence can be referred to herein as the cell barcode sequence or the partition barcode sequence (e.g., a droplet or well barcode sequence). In addition, the linker molecule may further comprise a unique identifier molecule (e.g., as depicted as $ID_3$). In the case of a double stranded linker molecule, C1a hybridizes to C1 and C2a hybridizes to C2 followed by ligation (not shown) to provide a barcoded nucleic acid molecule as shown in FIG. 15A. The remaining single stranded regions of Proximity Oligo #1 and #2 can be extended through a nucleic acid extension reaction to provide a barcoded nucleic acid molecule that is double-stranded. The barcoded nucleic acid molecule comprises elements from Proximity Oligo #1 (e.g., $ID_1$ and S1) and Proximity Oligo #2 (e.g., $ID_2$ and S2) and may optionally include functional sequences as described further herein.

In the case of a single-stranded linker molecule, the Proximity Oligo #1 and #2 may comprise additional sequences such as a sequence complementary to one or more additional sequences of the single stranded linker molecule. For example, Proximity Oligo #1 may comprise C1 as well as sequences complementary to $ID_3$ and/or BC and Proximity Oligo #2 may comprise C2 as well as sequences complementary to BC and/or $ID_3$. In this manner, hybridization of the single-stranded linker molecule to the proximity oligonucleotides can occur without any gaps and ligase may be used to join the two proximity oligonucleotides followed by nucleic acid extension to provide a double-stranded barcoded nucleic acid molecule. Alternatively, in the case of a single-stranded linker molecule, C1a hybridizes to C1 and C2a hybridizes to C2 leaving a gap represented by the $ID_3$ and BC sequences (not shown in FIG. 15A). The gap may be filled by nucleic acid extension followed by ligation to provide a barcoded nucleic acid molecule that still includes the original single stranded linker molecule. The remaining single stranded regions can be extended though a nucleic acid extension reaction to provide a barcoded nucleic acid molecule that is double-stranded. Alternatively or in addition to, in either case, the original single stranded linker molecule can be removed (e.g., by denaturing) to provide a barcoded nucleic acid molecule that is single stranded. The barcoded nucleic acid molecules generated from a single stranded linker molecule comprise elements from Proximity Oligo #1 (e.g., $ID_1$ and S1) and Proximity Oligo #2 (e.g., $ID_2$ and S2) and may optionally include functional sequences as described further herein.

FIG. 15B depicts Labelling Agent #1 which comprises two different types of proximity oligonucleotides. In some embodiments, the labelling agent comprises Proximity Oligo #1, as previously described in FIG. 15A. In one other embodiment, the labelling agent comprises an additional proximity oligonucleotide Proximity Oligo #2, which comprises a sequence that is different from that of Proximity Oligo #1, as previously described in FIG. 15A. However, unlike FIG. 15A, Labelling Agent #1 comprises both types of proximity oligonucleotides, wherein Proximity Oligo #2 comprises a unique identifier sequence that is identical to the unique identifier sequence of Proximity Oligo #1—$ID_1$. The presence of the same unique identifier sequence on the same labelling agent allows for the detection of intra-antibody interactions as the same unique identifier sequence may be present twice in the barcoded nucleic acid molecule. If intra-antibody information is not required, then different unique identifier sequences may be used for Labelling Agent #1 (e.g., $ID_1$ for Proximity Oligo #1 and $ID_2$ for Proximity Oligo #2) which may provide barcoded nucleic acid molecules comprising different unique identifiers, or complements thereof, from Proximity Oligo #1 or #2 and the same unique identifier may not be present twice in the same barcoded molecule.

In FIGS. 15A-B, the labelling agent may optionally comprise an additional reporter nucleic acid sequence (depicted as a dotted line for Labelling Agent #1 and a dashed line for Labelling Agent #2) that corresponds to the target molecule of the labelling agent (also referred to herein as a "feature barcode"). For instance, the reporter nucleic acid sequence may correspond to a protein that can be specifically bound by the labelling agent. The reporter nucleic acid sequence can provide information about the extent of labelling of the single cell by the labelling agent. In one embodiment, the reporter nucleic acid sequence (or a complement thereof) is designed to couple to a nucleic acid barcode molecule from a barcode carrying support (e.g., a bead). For example, the reporter nucleic acid sequence (or a complement thereof) may be configured to couple to (i) a sequence from bead 804 in FIG. 8 or (ii) a sequence 980 in FIG. 9, where the reporter nucleic acid sequence (or a complement thereof) comprises a sequence 985 coupled to an antibody. In one embodiment, the reporter nucleic acid sequence may be used to generate an additional barcoded nucleic acid molecule that is different from the barcoded nucleic acid molecule depicted at the bottom of FIGS. 15A-B. In another embodiment, the additional barcoded nucleic acid molecule comprises the reporter sequence, or a complement thereof, and an additional barcode sequence. In some embodiments, the additional barcode sequence is a cell or partition-specific barcode sequence, or complement thereof (e.g., to partition-specific sequence 910 of FIG. 9). In one embodiment, the additional barcode sequence, or complement thereof, is identical to the cell barcode sequence of the linker molecule, as described herein.

In one aspect, the methods described herein can be used to map protein interactions on a single cell level. In one embodiment, the methods allow the detection of the abundance of a set of protein targets, as well as the interactions between such protein targets. In another embodiment, the method comprises detecting a plurality of barcoded nucleic acid molecules, wherein a single barcoded nucleic acid molecule comprises elements of both a first proximity oligonucleotide and a second proximity oligonucleotide, thereby indicating the presence of a set of protein targets in proximity to one another (each target of the labelling agents used). In another embodiment, the plurality of barcoded nucleic acid molecule comprises unique identifiers, which allow for detection of the abundance of a set of protein targets in proximity to one another.

Figure 11:
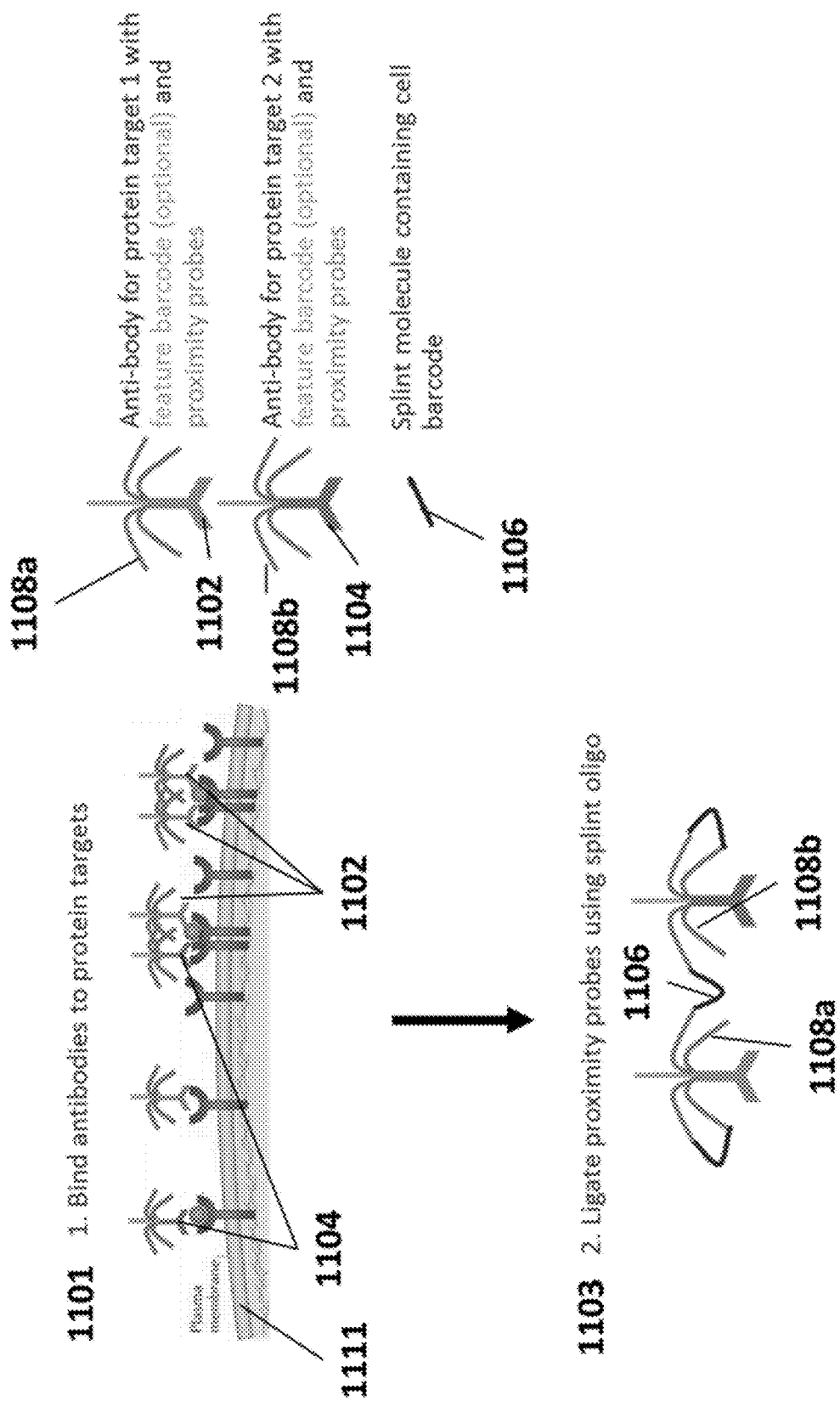
FIG. 11 depicts a representative steps of an exemplary processing scheme for mapping protein abundance and interactions in single cells.

FIG. 11 depicts non-limiting examples of the methods described herein. As shown in FIG. 11, an individual cell may be contacted 1101 with a first type of antibody 1102 that binds to a first protein, and a second type of antibody 1104 that binds to a second protein. For example, the first protein and the second protein may be positioned relative to a membrane 1110 of the cell. The first protein and the second protein may be a cell-surface protein (such as a cell-surface receptor), an intracellular protein, a protein associated with an intracellular organelle or compartment, or any combination thereof. The first protein and the second protein may be the same type of protein. Alternatively, the first protein and the second protein may be different types of protein. The first type of antibody 1102 may be coupled to a first proximity probe 1108a, and the second type of antibody 1104 may be coupled to a second proximity probe 1108b. The first type of antibody 1102 and the second type of antibody 1104 may be the same type of antibody. Alternatively, the first type of antibody 1102 and the second type of antibody 1104 may be different types of antibodies. After the first type of antibody 1102 has bound to the first protein, and the second type of antibody 1104 has bound to the second protein, a splint oligonucleotide 1106 may be contacted with the cell such that a portion of the splint oligonucleotide 1106 hybridizes 1103 with a portion of the first proximity probe 1108a, and a portion of the splint oligonucleotide 1106 hybridizes with a portion of the second proximity probe 1108b. The splint oligonucleotide 1106 may mediate both inter-antibody and intra-antibody interactions. The splint oligonucleotide may be coupled to the two proximity probes to generate a final barcoded molecule. The final barcoded molecule, compris-ing all or portions of the splint oligonucleotide 1106, the first proximity probe 1108a, and the second proximity probe 1108b, may be used in a downstream process (e.g., a sequencing reaction). In some instances, the proximity probes described herein (e.g., first proximity probe, second proximity probe) may further comprise a feature barcode, which may be any barcode sequence described elsewhere herein.

Figure 12:
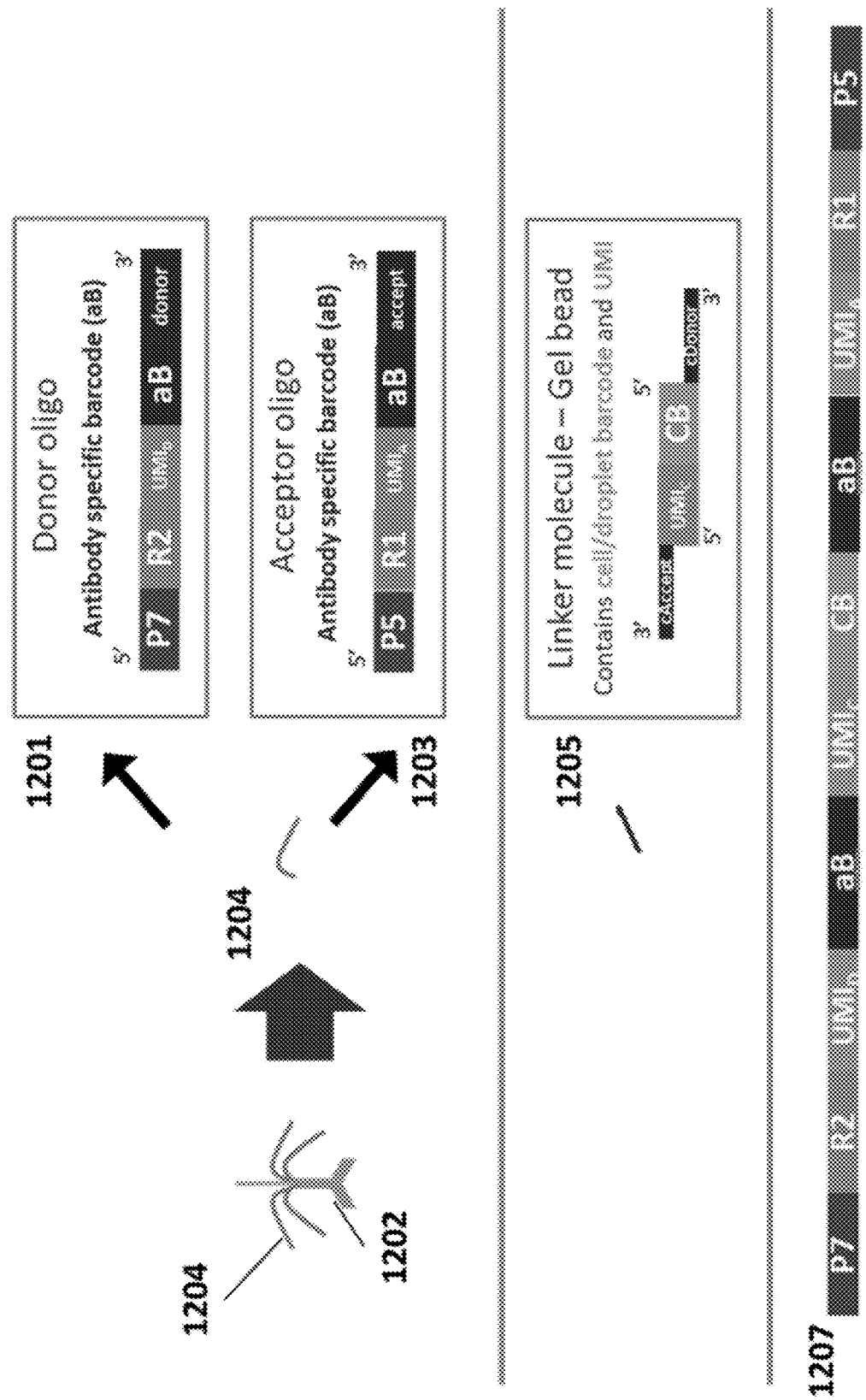
FIG. 12 depicts non-limiting examples of oligonucleotide compositions suitable for use with the methods and systems described herein.

FIG. 12 depicts non-limiting examples of oligonucleotide compositions suitable for use with the methods provided herein. An antibody 1202 described herein may be coupled to a proximity oligonucleotide 1204. Proximity oligonucleotides may be either single-stranded, or double-stranded with a single-stranded overhang at the end. Generally, a single-stranded portion at a terminal end of the proximity oligonucleotide may be complementary to a single-stranded portion of a splint oligonucleotide. Proximity oligonucleotides (e.g., 1204) may comprise either a donor probe 1201 or an acceptor probe 1203. A proximity oligonucleotide comprising a donor probe 1201 may include a donor sequence at a 3' end of the oligonucleotide ("donor", 1201). The proximity oligonucleotide may further comprise one or more of an antibody barcode ("aB", 1201), a unique molecular index ("UMI$_D$", 1201), and any additional suitable adapters, primer sequences, barcodes, tags, and the like ("P7", and "R2", 1201). A proximity oligonucleotide comprising an acceptor probe 1203 may include an acceptor sequence at a 3' end of the oligonucleotide ("accept", 1203). The proximity oligonucleotide may further comprise one or more of an antibody barcode ("aB", 1203), a unique molecular index ("UMI$_A$", 1203), and any additional suitable adapters, primer sequences, barcodes, tags, and the like ("P5", and "R1", 1203). A splint oligonucleotide 1005 may be a double-stranded oligonucleotide with single-stranded overhangs at both ends. The splint oligonucleotide may include a sequence at the 3' end that is complementary to the donor sequence found on the "donor" proximity probe 1201 ("cDonor", 1205), and a sequence at the 5' end that is complementary to the acceptor sequence found on the "acceptor" proximity probe 1203 ("cAcceptor", 1205). The splint oligonucleotide may further comprise one or more additional features including, but not limited to, a cell barcode ("CB", 1205) and a unique molecular index ("UMI$_C$", 1205). The donor proximity probe and the acceptor proximity probe may comprise the same sequence. Alternatively, the donor proximity probe and the acceptor proximity probe may comprise different sequences. A non-limiting example of a final barcoded molecule for sequencing is depicted in FIG. 12, 1207. For example, such final barcoded molecule 1207 may comprise one or more of the "P7" sequence from the donor probe, the "R2" sequence from the donor probe, the UMI$_D$ sequence from the donor probe, the antibody barcode sequence from the donor probe, the UMI$_C$ sequence from the splint oligonucleotide, the cell barcode from the splint oligonucleotide, the antibody barcode sequence from the acceptor probe, the UMI$_A$ sequence from the acceptor probe, the "R1" sequence from the acceptor probe, and the "P5" sequence from the acceptor probe (or derivative sequences thereof). The identity of the protein-protein interaction may be obtained by identifying the antibody barcodes in the barcoded molecule.

Systems and Methods for Sample Compartmentalization

In an aspect, the systems and methods described herein provide for the compartmentalization, depositing, or partitioning of one or more particles (e.g., analyte carriers, macromolecular constituents of analyte carriers, beads, reagents, etc.) into discrete compartments or partitions (referred to interchangeably herein as partitions), where each partition maintains separation of its own contents from the contents of other partitions. The partition can be a droplet in an emulsion. The partition can be a well of a microwell array. A partition may comprise one or more other partitions.

A partition may include one or more particles. A partition may include one or more types of particles. For example, a partition of the present disclosure may comprise one or more analyte carriers and/or macromolecular constituents thereof. A partition may comprise one or more gel beads. A partition may comprise one or more cell beads. A partition may include a single gel bead, a single cell bead, or both a single cell bead and single gel bead. A partition may include one or more reagents. Alternatively, a partition may be unoccupied. For example, a partition may not comprise a bead. A cell bead can be an analyte carrier and/or one or more of its macromolecular constituents encased inside of a gel or polymer matrix, such as via polymerization of a droplet containing the analyte carrier and precursors capable of being polymerized or gelled. Unique identifiers, such as barcodes, may be injected into the droplets previous to, subsequent to, or concurrently with droplet generation, such as via a microcapsule (e.g., bead), as described elsewhere herein. Microfluidic channel networks (e.g., on a chip) can be utilized to generate partitions as described herein. Alternative mechanisms may also be employed in the partitioning of individual analyte carriers, including porous membranes through which aqueous mixtures of cells are extruded into non-aqueous fluids.

The partitions can be flowable within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions may be provided in a water-in-oil emulsion or oil-in-water emulsion. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

In some instances, a droplet is formed by creating an emulsion by mixing or agitating immiscible phases. Mixing or agitation may comprise various agitation techniques, such as vortexing, pipetting, tube flicking, or other agitation techniques. In some cases, mixing or agitation may be performed without using a microfluidic device. In some examples, a droplet may be formed by exposing a mixture to ultrasound or sonication. For example, to partition contents into droplets, a mixture comprising a first fluid, a second fluid, optionally a surfactant, and the contents can be subject to such agitation techniques to generate a plurality of droplets (first fluid-in-second fluid or second fluid-in-first fluid) comprising the contents, or subsets thereof. In an example, a mixture comprises beads. Upon agitation, the beads in the mixture may limit droplet break-up into droplets smaller than the size of the beads, and a substantially monodisperse population of droplets comprising the beads may result.

In the case of droplets in an emulsion, allocating individual particles to discrete partitions may in one example be accomplished by introducing a flowing stream of particles in an aqueous fluid into a flowing stream or reservoir of a non-aqueous fluid, such that droplets are generated (see generally, e.g., FIGS. 1-7B). Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of analyte carrier per partition, number of beads per partition, etc.). For example, partition occupancy can be controlled by providing the aqueous stream at a certain concentration and/or flow rate of particles. To generate single analyte carrier partitions, the relative flow rates of the immiscible fluids can be selected such that, on average, the partitions may contain less than one analyte carrier per partition in order to ensure that those partitions that are occupied are primarily singly occupied. In some cases, partitions among a plurality of partitions may contain at most one analyte carrier (e.g., bead, DNA, cell or cellular material). In some examples, the various parameters (e.g., fluid properties, particle properties, microfluidic architectures, etc.) may be selected or adjusted such that a majority of partitions are occupied, for example, allowing for a small percentage of unoccupied partitions. The flows and channel architectures can be controlled as to ensure a given number of singly occupied partitions, less than a certain level of unoccupied partitions and/or less than a certain level of multiply occupied partitions.

FIG. 1 shows an example of a microfluidic channel structure 100 for partitioning individual analyte carriers. The channel structure 100 can include channel segments 102, 104, 106 and 108 communicating at a channel junction 110. In operation, a first aqueous fluid 112 that includes suspended analyte carriers (or cells) 114 may be transported along channel segment 102 into junction 110, while a second fluid 116 that is immiscible with the aqueous fluid 112 is delivered to the junction 110 from each of channel segments 104 and 106 to create discrete droplets 118, 120 of the first aqueous fluid 112 flowing into channel segment 108 and flowing away from junction 110. The channel segment 108 may be fluidically coupled to an outlet reservoir where the discrete droplets can be stored and/or harvested. A discrete droplet generated may include an individual analyte carrier 114 (such as droplets 118). A discrete droplet generated may include more than one individual analyte carrier 114 (not shown in FIG. 1). A discrete droplet may contain no analyte carrier 114 (such as droplet 120). Each discrete partition may maintain separation of its own contents (e.g., individual analyte carrier 114) from the contents of other partitions.

The second fluid 116 can comprise an oil, such as a fluorinated oil, that includes a fluorosurfactant for stabilizing the resulting droplets, for example, inhibiting subsequent coalescence of the resulting droplets 118, 120. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 100 may have other geometries. For example, a microfluidic channel structure can have more than one channel junction. For example, a microfluidic channel structure can have 2, 3, 4, or 5 channel segments each carrying particles (e.g., analyte carriers, cell beads, and/or gel beads) that meet at a channel junction. Fluid may be directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 118, containing one or more analyte carriers 114, and (2) unoccupied droplets 120, not containing any analyte carriers 114. Occupied droplets 118 may comprise singly occupied droplets (having one analyte carrier) and multiply occupied droplets (having more than one analyte carrier). As described elsewhere herein, in some cases, the majority of occupied partitions can include no more than one analyte carrier per occupied partition and some of the generated partitions can be unoccupied (of any analyte carrier). In some cases, though, some of the occupied partitions may include more than one analyte carrier. In some cases, the partitioning process may be controlled such that fewer than about 25% of the occupied partitions contain more than one analyte carrier, and in many cases, fewer than about 20% of the occupied partitions have more than one analyte carrier, while in some cases, fewer than about 10% or even fewer than about 5% of the occupied partitions include more than one analyte carrier per partition.

In some cases, it may be desirable to minimize the creation of excessive numbers of empty partitions, such as to reduce costs and/or increase efficiency. While this minimization may be achieved by providing a sufficient number of analyte carriers (e.g., analyte carriers 114) at the partitioning junction 110, such as to ensure that at least one analyte carrier is encapsulated in a partition, the Poissonian distribution may expectedly increase the number of partitions that include multiple analyte carriers. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In some cases, the flow of one or more of the analyte carriers (e.g., in channel segment 102), or other fluids directed into the partitioning junction (e.g., in channel segments 104, 106) can be controlled such that, in many cases, no more than about 50% of the generated partitions, no more than about 25% of the generated partitions, or no more than about 10% of the generated partitions are unoccupied. These flows can be controlled so as to present a non-Poissonian distribution of single-occupied partitions while providing lower levels of unoccupied partitions. The above noted ranges of unoccupied partitions can be achieved while still providing any of the single occupancy rates described above. For example, in many cases, the use of the systems and methods described herein can create resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

Figure 2:
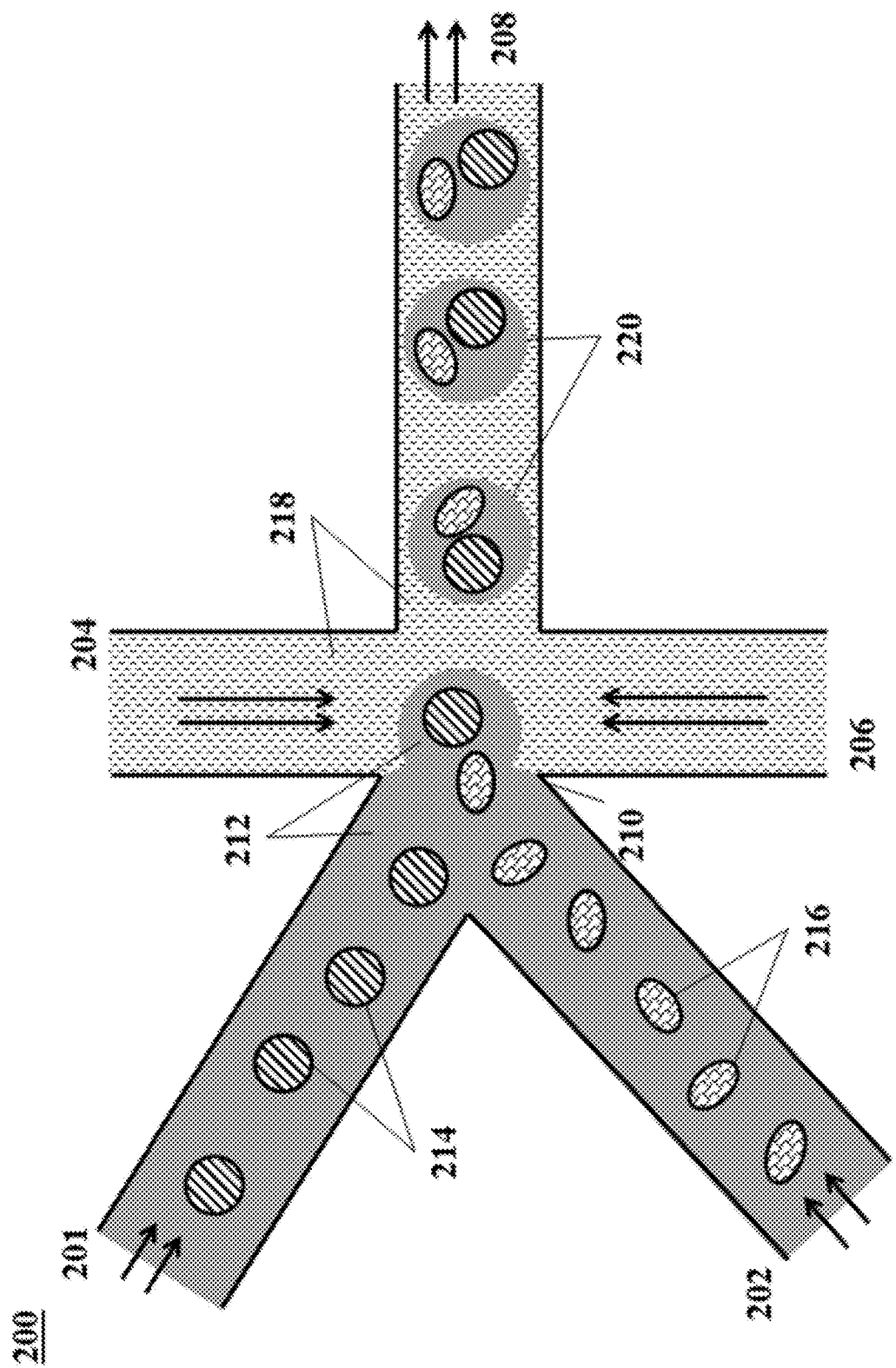
FIG. 2 shows an example of a microfluidic channel structure for delivering barcode carrying beads to droplets.

As will be appreciated, the above-described occupancy rates are also applicable to partitions that include both analyte carriers and additional reagents, including, but not limited to, microcapsules or beads (e.g., gel beads) carrying barcoded nucleic acid molecules (e.g., oligonucleotides) (described in relation to FIG. 2). The occupied partitions (e.g., at least about 10%, 20%, 30%, 40%, 50%, 60%, 70%, 80%, 90%, 95%, or 99% of the occupied partitions) can include both a microcapsule (e.g., bead) comprising barcoded nucleic acid molecules and an analyte carrier.

In another aspect, in addition to or as an alternative to droplet based partitioning, analyte carriers may be encapsulated within a microcapsule that comprises an outer shell, layer or porous matrix in which is entrained one or more individual analyte carriers or small groups of analyte carriers. The microcapsule may include other reagents. Encapsulation of analyte carriers may be performed by a variety of processes. Such processes may combine an aqueous fluid containing the analyte carriers with a polymeric precursor material that may be capable of being formed into a gel or other solid or semi-solid matrix upon application of a particular stimulus to the polymer precursor. Such stimuli can include, for example, thermal stimuli (e.g., either heating or cooling), photo-stimuli (e.g., through photo-curing), chemical stimuli (e.g., through crosslinking, polymerization initiation of the precursor (e.g., through added initiators)), mechanical stimuli, or a combination thereof.

Preparation of microcapsules comprising analyte carriers may be performed by a variety of methods. For example, air knife droplet or aerosol generators may be used to dispense droplets of precursor fluids into gelling solutions in order to form microcapsules that include individual analyte carriers or small groups of analyte carriers. Likewise, membrane based encapsulation systems may be used to generate microcapsules comprising encapsulated analyte carriers as described herein. Microfluidic systems of the present disclosure, such as that shown in FIG. 1, may be readily used in encapsulating cells as described herein. In particular, and with reference to FIG. 1, the aqueous fluid 112 comprising (i) the analyte carriers 114 and (ii) the polymer precursor material (not shown) is flowed into channel junction 110, where it is partitioned into droplets 118, 120 through the flow of non-aqueous fluid 116. In the case of encapsulation methods, non-aqueous fluid 116 may also include an initiator (not shown) to cause polymerization and/or crosslinking of the polymer precursor to form the microcapsule that includes the entrained analyte carriers. Examples of polymer precursor/initiator pairs include those described in U.S. Patent Application Publication No. 2014/0378345, which is entirely incorporated herein by reference for all purposes.

For example, in the case where the polymer precursor material comprises a linear polymer material, such as a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent such as tetraethylmethylenediamine (TEMED) may be provided within the second fluid streams 116 in channel segments 104 and 106, which can initiate the copolymerization of the acrylamide and BAC into a cross-linked polymer network, or hydrogel.

Upon contact of the second fluid stream 116 with the first fluid stream 112 at junction 110, during formation of droplets, the TEMED may diffuse from the second fluid 116 into the aqueous fluid 112 comprising the linear polyacrylamide, which will activate the crosslinking of the polyacrylamide within the droplets 118, 120, resulting in the formation of gel (e.g., hydrogel) microcapsules, as solid or semi-solid beads or particles entraining the cells 114. Although described in terms of polyacrylamide encapsulation, other 'activatable' encapsulation compositions may also be employed in the context of the methods and compositions described herein. For example, formation of alginate droplets followed by exposure to divalent metal ions (e.g., $Ca^{2+}$ ions), can be used as an encapsulation process using the described processes. Likewise, agarose droplets may also be transformed into capsules through temperature based gelling (e.g., upon cooling, etc.).

In some cases, encapsulated analyte carriers can be selectively releasable from the microcapsule, such as through passage of time or upon application of a particular stimulus, that degrades the microcapsule sufficiently to allow the analyte carriers (e.g., cell), or its other contents to be released from the microcapsule, such as into a partition (e.g., droplet). For example, in the case of the polyacrylamide polymer described above, degradation of the microcapsule may be accomplished through the introduction of an appropriate reducing agent, such as DTT or the like, to cleave disulfide bonds that cross-link the polymer matrix. See, for example, U.S. Patent Application Publication No. 2014/0378345, which is entirely incorporated herein by reference for all purposes.

The analyte carrier can be subjected to other conditions sufficient to polymerize or gel the precursors. The conditions sufficient to polymerize or gel the precursors may comprise exposure to heating, cooling, electromagnetic radiation, and/or light. The conditions sufficient to polymerize or gel the precursors may comprise any conditions sufficient to polymerize or gel the precursors. Following polymerization or gelling, a polymer or gel may be formed around the analyte carrier. The polymer or gel may be diffusively permeable to chemical or biochemical reagents. The polymer or gel may be diffusively impermeable to macromolecular constituents of the analyte carrier. In this manner, the polymer or gel may act to allow the analyte carrier to be subjected to chemical or biochemical operations while spatially confining the macromolecular constituents to a region of the droplet defined by the polymer or gel. The polymer or gel may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

The polymer or gel may be functionalized to bind to targeted analytes, such as nucleic acids, proteins, carbohydrates, lipids or other analytes. The polymer or gel may be polymerized or gelled via a passive mechanism. The polymer or gel may be stable in alkaline conditions or at elevated temperature. The polymer or gel may have mechanical properties similar to the mechanical properties of the bead. For instance, the polymer or gel may be of a similar size to the bead. The polymer or gel may have a mechanical strength (e.g. tensile strength) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The polymer may comprise poly(acrylamide-co-acrylic acid) crosslinked with disulfide linkages. The preparation of the polymer may comprise a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). Following the two steps, the analyte carrier may be surrounded by polyacrylamide strands linked together by disulfide bridges. In this manner, the analyte carrier may be encased inside of or comprise a gel or matrix (e.g., polymer matrix) to form a "cell bead."

A cell bead can contain analyte carriers (e.g., a cell) or macromolecular constituents (e.g., RNA, DNA, proteins, etc.) of analyte carriers. A cell bead may include a single cell or multiple cells, or a derivative of the single cell or multiple cells. For example after lysing and washing the cells, inhibitory components from cell lysates can be washed away and the macromolecular constituents can be bound as cell beads. Systems and methods disclosed herein can be applicable to both cell beads (and/or droplets or other partitions) containing analyte carriers and cell beads (and/or droplets or other partitions) containing macromolecular constituents of analyte carriers. Cell beads may be or include a cell, cell derivative, cellular material and/or material derived from the cell in, within, or encased in a matrix, such as a polymeric matrix. In some cases, a cell bead may comprise a live cell. In some instances, the live cell may be capable of being cultured when enclosed in a gel or polymer matrix, or of being cultured when comprising a gel or polymer matrix. In some instances, the polymer or gel may be diffusively permeable to certain components and diffusively impermeable to other components (e.g., macromolecular constituents).

Encapsulated analyte carriers can provide certain potential advantages of being more storable and more portable than droplet-based partitioned analyte carriers. Furthermore, in some cases, it may be desirable to allow analyte carriers to incubate for a select period of time before analysis, such as in order to characterize changes in such analyte carriers over time, either in the presence or absence of different stimuli (or reagents). In such cases, encapsulation may allow for longer incubation than partitioning in emulsion droplets, although in some cases, droplet partitioned analyte carriers may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of analyte carriers may constitute the partitioning of the analyte carriers into which other reagents are co-partitioned. Alternatively or in addition, encapsulated analyte carriers may be readily deposited into other partitions (e.g., droplets) as described above.

As described herein, one or more processes may be performed in a partition, which may be a well. The well may be a well of a plurality of wells of a substrate, such as a microwell of a microwell array or plate, or the well may be a microwell or microchamber of a device (e.g., microfluidic device) comprising a substrate. The well may be a well of a well array or plate, or the well may be a well or chamber of a device (e.g., fluidic device). Accordingly, the wells or microwells may assume an "open" configuration, in which the wells or microwells are exposed to the environment (e.g., contain an open surface) and are accessible on one planar face of the substrate, or the wells or microwells may assume a "closed" or "sealed" configuration, in which the microwells are not accessible on a planar face of the substrate. In some instances, the wells or microwells may be configured to toggle between "open" and "closed" configurations. For instance, an "open" microwell or set of microwells may be "closed" or "sealed" using a membrane (e.g., semi-permeable membrane), an oil (e.g., fluorinated oil to cover an aqueous solution), or a lid, as described elsewhere herein.

The well may have a volume of less than 1 milliliter (mL). For instance, the well may be configured to hold a volume of at most 1000 microliters (μL), at most 100 μL, at most 10 μL, at most 1 μL, at most 100 nanoliters (nL), at most 10 nL, at most 1 nL, at most 100 picoliters (μL), at most 10 (μL), or less. The well may be configured to hold a volume of about 1000 μL, about 100 μL, about 10 μL, about 1 μL, about 100 nL, about 10 nL, about 1 nL, about 100 μL, about 10 μL, etc. The well may be configured to hold a volume of at least 10 μL, at least 100 μL, at least 1 nL, at least 10 nL, at least 100 nL, at least 1 μL, at least 10 μL, at least 100 μL, at least 1000 μL, or more. The well may be configured to hold a volume in a range of volumes listed herein, for example, from about 5 nL to about 20 nL, from about 1 nL to about 100 nL, from about 500 μL to about 100 μL, etc. The well may be of a plurality of wells that have varying volumes and may be configured to hold a volume appropriate to accommodate any of the partition volumes described herein.

In some instances, a microwell array or plate comprises a single variety of microwells. In some instances, a microwell array or plate comprises a variety of microwells. For instance, the microwell array or plate may comprise one or more types of microwells within a single microwell array or plate. The types of microwells may have different dimensions (e.g., length, width, diameter, depth, cross-sectional area, etc.), shapes (e.g., circular, triangular, square, rectangular, pentagonal, hexagonal, heptagonal, octagonal, nonagonal, decagonal, etc.), aspect ratios, or other physical characteristics. The microwell array or plate may comprise any number of different types of microwells. For example, the microwell array or plate may comprise 1, 2, 3, 4, 5, 6, 7, 8, 9, 10, 20, 30, 40, 50, 60, 70, 80, 90, 100, 200, 300, 400, 500, 600, 700, 800, 900, 1000 or more different types of microwells. A well may have any dimension (e.g., length, width, diameter, depth, cross-sectional area, volume, etc.), shape (e.g., circular, triangular, square, rectangular, pentagonal, hexagonal, heptagonal, octagonal, nonagonal, decagonal, other polygonal, etc.), aspect ratios, or other physical characteristics described herein with respect to any well.

In certain instances, the microwell array or plate comprises different types of microwells that are located adjacent to one another within the array or plate. For instance, a microwell with one set of dimensions may be located adjacent to and in contact with another microwell with a different set of dimensions. Similarly, microwells of different geometries may be placed adjacent to or in contact with one another. The adjacent microwells may be configured to hold different articles; for example, one microwell may be used to contain a cell, cell bead, or other sample (e.g., cellular components, nucleic acid molecules, etc.) while the adjacent microwell may be used to contain a microcapsule, droplet, bead, or other reagent. In some cases, the adjacent microwells may be configured to merge the contents held within, e.g., upon application of a stimulus, or spontaneously, upon contact of the articles in each microwell.

As is described elsewhere herein, a plurality of partitions may be used in the systems, compositions, and methods described herein. For example, any suitable number of partitions (e.g., wells or droplets) can be generated or otherwise provided. For example, in the case when wells are used, at least about 1,000 wells, at least about 5,000 wells, at least about 10,000 wells, at least about 50,000 wells, at least about 100,000 wells, at least about 500,000 wells, at least about 1,000,000 wells, at least about 5,000,000 wells at least about 10,000,000 wells, at least about 50,000,000 wells, at least about 100,000,000 wells, at least about 500,000,000 wells, at least about 1,000,000,000 wells, or more wells can be generated or otherwise provided. Moreover, the plurality of wells may comprise both unoccupied wells (e.g., empty wells) and occupied wells.

A well may comprise any of the reagents described herein, or combinations thereof. These reagents may include, for example, barcode molecules, enzymes, adapters, and combinations thereof. The reagents may be physically separated from a sample (e.g., a cell, cell bead, or cellular components, e.g., proteins, nucleic acid molecules, etc.) that is placed in the well. This physical separation may be accomplished by containing the reagents within, or coupling to, a microcapsule or bead that is placed within a well. The physical separation may also be accomplished by dispensing the reagents in the well and overlaying the reagents with a layer that is, for example, dissolvable, meltable, or permeable prior to introducing the polynucleotide sample into the well. This layer may be, for example, an oil, wax, membrane (e.g., semi-permeable membrane), or the like. The well may be sealed at any point, for example, after addition of the microcapsule or bead, after addition of the reagents, or after addition of either of these components. The sealing of the well may be useful for a variety of purposes, including preventing escape of beads or loaded reagents from the well, permitting select delivery of certain reagents (e.g., via the use of a semi-permeable membrane), for storage of the well prior to or following further processing, etc.

A well may comprise free reagents and/or reagents encapsulated in, or otherwise coupled to or associated with, microcapsules, beads, or droplets. Any of the reagents described in this disclosure may be encapsulated in, or otherwise coupled to, a microcapsule, droplet, or bead, with any chemicals, particles, and elements suitable for sample processing reactions involving biomolecules, such as, but not limited to, nucleic acid molecules and proteins. For example, a bead or droplet used in a sample preparation reaction for DNA sequencing may comprise one or more of the following reagents: enzymes, restriction enzymes (e.g., multiple cutters), ligase, polymerase, fluorophores, oligonucleotide barcodes, adapters, buffers, nucleotides (e.g., dNTPs, ddNTPs) and the like.

Additional examples of reagents include, but are not limited to: buffers, acidic solution, basic solution, temperature-sensitive enzymes, pH-sensitive enzymes, light-sensitive enzymes, metals, metal ions, magnesium chloride, sodium chloride, manganese, aqueous buffer, mild buffer, ionic buffer, inhibitor, enzyme, protein, polynucleotide, antibodies, saccharides, lipid, oil, salt, ion, detergents, ionic detergents, non-ionic detergents, oligonucleotides, nucleotides, deoxyribonucleotide triphosphates (dNTPs), dideoxyribonucleotide triphosphates (ddNTPs), DNA, RNA, peptide polynucleotides, complementary DNA (cDNA), double stranded DNA (dsDNA), single stranded DNA (ssDNA), plasmid DNA, cosmid DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA, polymerase, ligase, restriction enzymes, proteases, nucleases, protease inhibitors, nuclease inhibitors, chelating agents, reducing agents, oxidizing agents, fluorophores, probes, chromophores, dyes, organics, emulsifiers, surfactants, stabilizers, polymers, water, small molecules, pharmaceuticals, radioactive molecules, preservatives, antibiotics, aptamers, and pharmaceutical drug compounds. As described herein, one or more reagents in the well may be used to perform one or more reactions, including but not limited to: cell lysis, cell fixation, permeabilization, nucleic acid reactions, e.g., nucleic acid extension reactions, amplification, reverse transcription, transposase reactions (e.g., tagmentation), etc.

The wells may be provided as a part of a kit. For example, a kit may comprise instructions for use, a microwell array or device, and reagents (e.g., beads). The kit may comprise any useful reagents for performing the processes described herein, e.g., nucleic acid reactions, barcoding of nucleic acid molecules, sample processing (e.g., for cell lysis, fixation, and/or permeabilization).

In some cases, a well comprises a microcapsule, bead, or droplet that comprises a set of reagents that has a similar attribute (e.g., a set of enzymes, a set of minerals, a set of oligonucleotides, a mixture of different barcode molecules, a mixture of identical barcode molecules). In other cases, a microcapsule, bead, or droplet comprises a heterogeneous mixture of reagents. In some cases, the heterogeneous mixture of reagents can comprise all components necessary to perform a reaction. In some cases, such mixture can comprise all components necessary to perform a reaction, except for 1, 2, 3, 4, 5, or more components necessary to perform a reaction. In some cases, such additional components are contained within, or otherwise coupled to, a different microcapsule, droplet, or bead, or within a solution within a partition (e.g., microwell) of the system.

Figure 13:
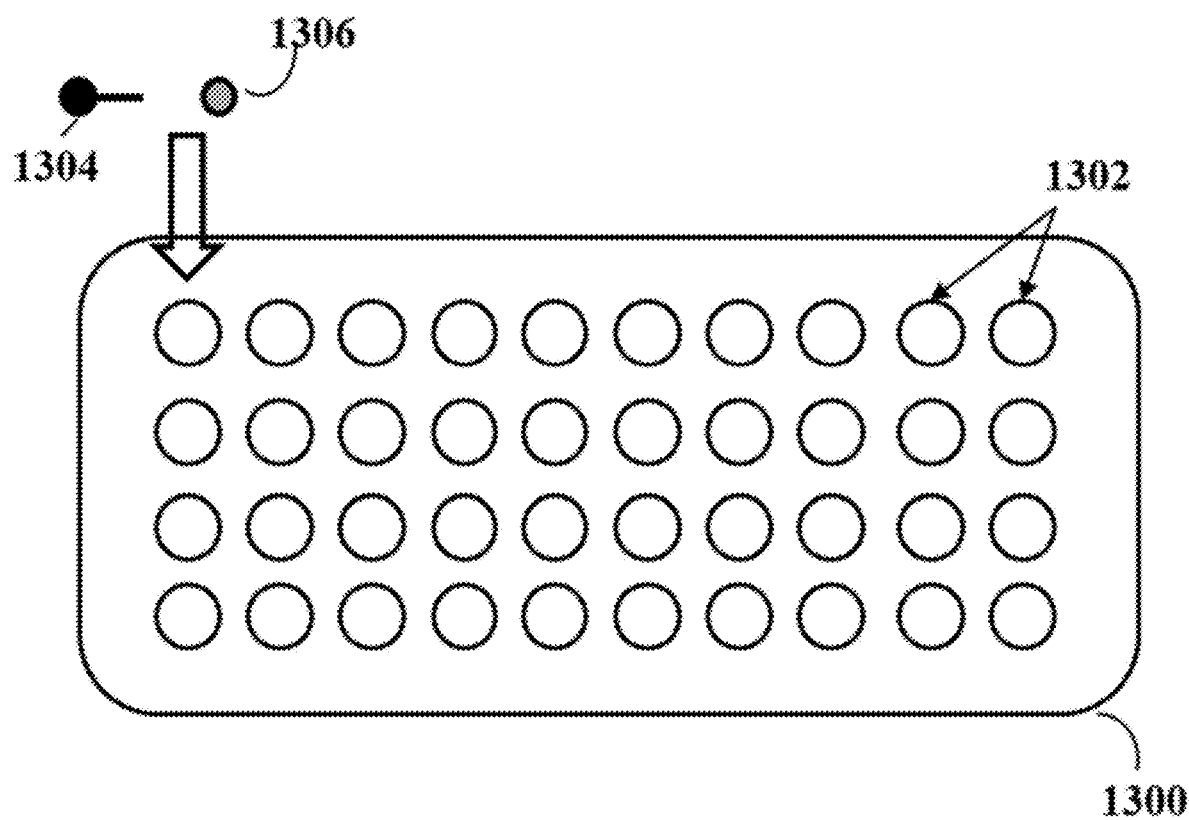
FIG. 13 schematically illustrates an example microwell array.

FIG. 13 schematically illustrates an example of a microwell array. The array can be contained within a substrate 1300. The substrate 1300 comprises a plurality of wells 1302. The wells 1302 may be of any size or shape, and the spacing between the wells, the number of wells per substrate, as well as the density of the wells on the substrate 1300 can be modified, depending on the particular application. In one such example application, a sample molecule 1306, which may comprise a cell or cellular components (e.g., nucleic acid molecules) is co-partitioned with a bead 1304, which may comprise a nucleic acid barcode molecule coupled thereto. The wells 1302 may be loaded using gravity or other loading technique (e.g., centrifugation, liquid handler, acoustic loading, optoelectronic, etc.). In some instances, at least one of the wells 1302 contains a single sample molecule 1306 (e.g., cell) and a single bead 1304.

Reagents may be loaded into a well either sequentially or concurrently. In some cases, reagents are introduced to the device either before or after a particular operation. In some cases, reagents (which may be provided, in certain instances, in microcapsules, droplets, or beads) are introduced sequentially such that different reactions or operations occur at different steps. The reagents (or microcapsules, droplets, or beads) may also be loaded at operations interspersed with a reaction or operation step. For example, microcapsules (or droplets or beads) comprising reagents for fragmenting polynucleotides (e.g., restriction enzymes) and/or other enzymes (e.g., transposases, ligases, polymerases, etc.) may be loaded into the well or plurality of wells, followed by loading of microcapsules, droplets, or beads comprising reagents for attaching nucleic acid barcode molecules to a sample nucleic acid molecule. Reagents may be provided concurrently or sequentially with a sample, e.g., a cell or cellular components (e.g., organelles, proteins, nucleic acid molecules, carbohydrates, lipids, etc.). Accordingly, use of wells may be useful in performing multi-step operations or reactions.

As described elsewhere herein, the nucleic acid barcode molecules and other reagents may be contained within a microcapsule, bead, or droplet. These microcapsules, beads, or droplets may be loaded into a partition (e.g., a microwell) before, after, or concurrently with the loading of a cell, such that each cell is contacted with a different microcapsule, bead, or droplet. This technique may be used to attach a unique nucleic acid barcode molecule to nucleic acid molecules obtained from each cell. Alternatively or in addition to, the sample nucleic acid molecules may be attached to a support. For instance, the partition (e.g., microwell) may comprise a bead which has coupled thereto a plurality of nucleic acid barcode molecules. The sample nucleic acid molecules, or derivatives thereof, may couple or attach to the nucleic acid barcode molecules on the support. The resulting barcoded nucleic acid molecules may then be removed from the partition, and in some instances, pooled and sequenced. In such cases, the nucleic acid barcode sequences may be used to trace the origin of the sample nucleic acid molecule. For example, polynucleotides with identical barcodes may be determined to originate from the same cell or partition, while polynucleotides with different barcodes may be determined to originate from different cells or partitions.

The samples or reagents may be loaded in the wells or microwells using a variety of approaches. The samples (e.g., a cell, cell bead, or cellular component) or reagents (as described herein) may be loaded into the well or microwell using an external force, e.g., gravitational force, electrical force, magnetic force, or using mechanisms to drive the sample or reagents into the well, e.g., via pressure-driven flow, centrifugation, optoelectronics, acoustic loading, electrokinetic pumping, vacuum, capillary flow, etc. In certain cases, a fluid handling system may be used to load the samples or reagents into the well. The loading of the samples or reagents may follow a Poissonian distribution or a non-Poissonian distribution, e.g., super Poisson or sub-Poisson. The geometry, spacing between wells, density, and size of the microwells may be modified to accommodate a useful sample or reagent distribution; for instance, the size and spacing of the microwells may be adjusted such that the sample or reagents may be distributed in a super-Poissonian fashion.

In one particular non-limiting example, the microwell array or plate comprises pairs of microwells, in which each pair of microwells is configured to hold a droplet (e.g., comprising a single cell) and a single bead (such as those described herein, which may, in some instances, also be encapsulated in a droplet). The droplet and the bead (or droplet containing the bead) may be loaded simultaneously or sequentially, and the droplet and the bead may be merged, e.g., upon contact of the droplet and the bead, or upon application of a stimulus (e.g., external force, agitation, heat, light, magnetic or electric force, etc.). In some cases, the loading of the droplet and the bead is super-Poissonian. In other examples of pairs of microwells, the wells are configured to hold two droplets comprising different reagents and/or samples, which are merged upon contact or upon application of a stimulus. In such instances, the droplet of one microwell of the pair can comprise reagents that may react with an agent in the droplet of the other microwell of the pair. For instance, one droplet can comprise reagents that are configured to release the nucleic acid barcode molecules of a bead contained in another droplet, located in the adjacent microwell. Upon merging of the droplets, the nucleic acid barcode molecules may be released from the bead into the partition (e.g., the microwell or microwell pair that are in contact), and further processing may be performed (e.g., barcoding, nucleic acid reactions, etc.). In cases where intact or live cells are loaded in the microwells, one of the droplets may comprise lysis reagents for lysing the cell upon droplet merging.

A droplet or microcapsule may be partitioned into a well. The droplets may be selected or subjected to pre-processing prior to loading into a well. For instance, the droplets may comprise cells, and only certain droplets, such as those containing a single cell (or at least one cell), may be selected for use in loading of the wells. Such a pre-selection process may be useful in efficient loading of single cells, such as to obtain a non-Poissonian distribution, or to pre-filter cells for a selected characteristic prior to further partitioning in the wells. Additionally, the technique may be useful in obtaining or preventing cell doublet or multiplet formation prior to or during loading of the microwell.

In some instances, the wells can comprise nucleic acid barcode molecules attached thereto. The nucleic acid barcode molecules may be attached to a surface of the well (e.g., a wall of the well). The nucleic acid barcode molecule (e.g., a partition barcode sequence) of one well may differ from the nucleic acid barcode molecule of another well, which can permit identification of the contents contained with a single partition or well. In some cases, the nucleic acid barcode molecule can comprise a spatial barcode sequence that can identify a spatial coordinate of a well, such as within the well array or well plate. In some cases, the nucleic acid barcode molecule can comprise a unique molecular identifier for individual molecule identification. In some instances, the nucleic acid barcode molecules may be configured to attach to or capture a nucleic acid molecule within a sample or cell distributed in the well. For example, the nucleic acid barcode molecules may comprise a capture sequence that may be used to capture or hybridize to a nucleic acid molecule (e.g., RNA, DNA) within the sample. In some instances, the nucleic acid barcode molecules may be releasable from the microwell. For instance, the nucleic acid barcode molecules may comprise a chemical cross-linker which may be cleaved upon application of a stimulus (e.g., photo-, magnetic, chemical, biological, stimulus). The released nucleic acid barcode molecules, which may be hybridized or configured to hybridize to a sample nucleic acid molecule, may be collected and pooled for further processing, which can include nucleic acid processing (e.g., amplification, extension, reverse transcription, etc.) and/or characterization (e.g., sequencing). In such cases, the unique partition barcode sequences may be used to identify the cell or partition from which a nucleic acid molecule originated.

Characterization of samples within a well may be performed. Such characterization can include, in non-limiting examples, imaging of the sample (e.g., cell, cell bead, or cellular components) or derivatives thereof. Characterization techniques such as microscopy or imaging may be useful in measuring sample profiles in fixed spatial locations. For instance, when cells are partitioned, optionally with beads, imaging of each microwell and the contents contained therein may provide useful information on cell doublet formation (e.g., frequency, spatial locations, etc.), cell-bead pair efficiency, cell viability, cell size, cell morphology, expression level of a biomarker (e.g., a surface marker, a fluorescently labeled molecule therein, etc.), cell or bead loading rate, number of cell-bead pairs, etc. In some instances, imaging may be used to characterize live cells in the wells, including, but not limited to: dynamic live-cell tracking, cell-cell interactions (when two or more cells are co-partitioned), cell proliferation, etc. Alternatively or in addition to, imaging may be used to characterize a quantity of amplification products in the well.

In operation, a well may be loaded with a sample and reagents, simultaneously or sequentially. When cells or cell beads are loaded, the well may be subjected to washing, e.g., to remove excess cells from the well, microwell array, or plate. Similarly, washing may be performed to remove excess beads or other reagents from the well, microwell array, or plate. In the instances where live cells are used, the cells may be lysed in the individual partitions to release the intracellular components or cellular analytes. Alternatively, the cells may be fixed and/or permeabilized in the individual partitions. The intracellular components or cellular analytes may couple to a support, e.g., on a surface of the microwell, on a solid support (e.g., bead), or they may be collected for further downstream processing. For instance, after cell lysis, the intracellular components or cellular analytes may be transferred to individual droplets or other partitions for barcoding. Alternatively, or in addition to, the intracellular components or cellular analytes (e.g., nucleic acid molecules) may couple to a bead comprising a nucleic acid barcode molecule; subsequently, the bead may be collected and further processed, e.g., subjected to nucleic acid reaction such as reverse transcription, amplification, or extension, and the nucleic acid molecules thereon may be further characterized, e.g., via sequencing. Alternatively, or in addition to, the intracellular components or cellular analytes may be barcoded in the well (e.g., using a bead comprising nucleic acid barcode molecules that are releasable or on a surface of the microwell comprising nucleic acid barcode molecules). The barcoded nucleic acid molecules or analytes may be further processed in the well, or the barcoded nucleic acid molecules or analytes may be collected from the individual partitions and subjected to further processing outside the partition. Further processing can include nucleic acid processing (e.g., performing an amplification, extension) or characterization (e.g., fluorescence monitoring of amplified molecules, sequencing). At any convenient or useful step, the well (or microwell array or plate) may be sealed (e.g., using an oil, membrane, wax, etc.), which enables storage of the assay or selective introduction of additional reagents.

Figure 14:
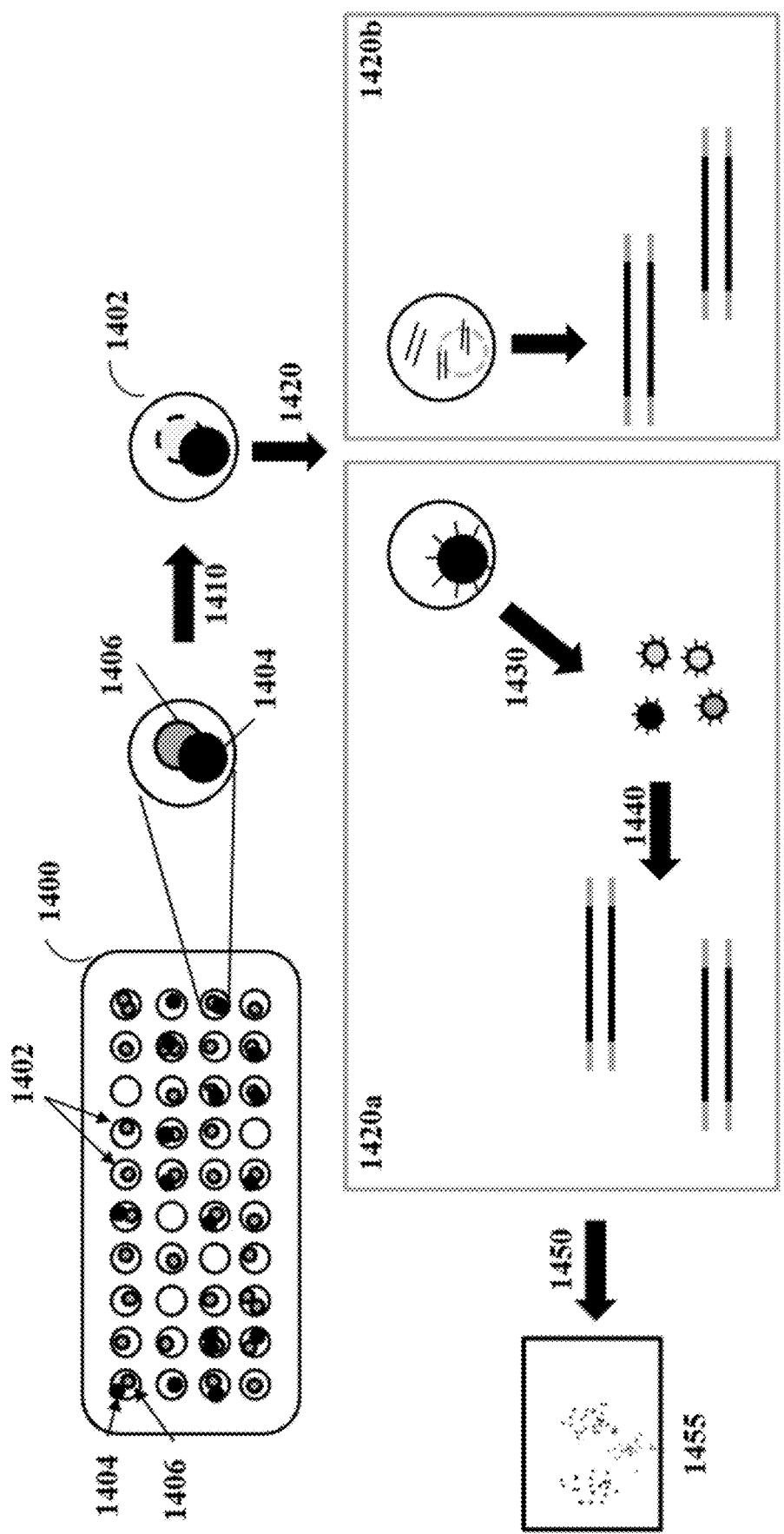
FIG. 14 schematically illustrates an example workflow for processing nucleic acid molecules.

FIG. 14 schematically shows an example workflow for processing nucleic acid molecules within a sample. A substrate 1400 comprising a plurality of microwells 1402 may be provided. A sample 1406 which may comprise a cell, cell bead, cellular components or analytes (e.g., proteins and/or nucleic acid molecules) can be co-partitioned, in a plurality of microwells 1402, with a plurality of beads 1404 comprising nucleic acid barcode molecules. During process 1410, the sample 1406 may be processed within the partition. For instance, in the case of live cells, the cell may be subjected to conditions sufficient to lyse the cells and release the analytes contained therein. In process 1420, the bead 1404 may be further processed. By way of example, processes 1420*a* and 1420*b* schematically illustrate different workflows, depending on the properties of the bead 1404.

In 1420*a*, the bead comprises nucleic acid barcode molecules that are attached thereto, and sample nucleic acid molecules (e.g., RNA, DNA) may attach, e.g., via hybridization of ligation, to the nucleic acid barcode molecules. Such attachment may occur on the bead. In process 1430, the beads 1404 from multiple wells 1402 may be collected and pooled. Further processing may be performed in process 1440. For example, one or more nucleic acid reactions may be performed, such as reverse transcription, nucleic acid extension, amplification, ligation, transposition, etc. In some instances, adapter sequences are ligated to the nucleic acid molecules, or derivatives thereof, as described elsewhere herein. For instance, sequencing primer sequences may be appended to each end of the nucleic acid molecule. In process 1450, further characterization, such as sequencing may be performed to generate sequencing reads. The sequencing reads may yield information on individual cells or populations of cells, which may be represented visually or graphically, e.g., in a plot 1455.

In 1420*b*, the bead comprises nucleic acid barcode molecules that are releasably attached thereto, as described below. The bead may degrade or otherwise release the nucleic acid barcode molecules into the well 1402; the nucleic acid barcode molecules may then be used to barcode nucleic acid molecules within the well 1402. Further processing may be performed either inside the partition or outside the partition. For example, one or more nucleic acid reactions may be performed, such as reverse transcription, nucleic acid extension, amplification, ligation, transposition, etc. In some instances, adapter sequences are ligated to the nucleic acid molecules, or derivatives thereof, as described elsewhere herein. For instance, sequencing primer sequences may be appended to each end of the nucleic acid molecule. In process 1450, further characterization, such as sequencing may be performed to generate sequencing reads. The sequencing reads may yield information on individual cells or populations of cells, which may be represented visually or graphically, e.g., in a plot 1455.

Beads

Nucleic acid barcode molecules may be delivered to a partition (e.g., a droplet or well) via a solid support or carrier (e.g., a bead). In some cases, nucleic acid barcode molecules are initially associated with the solid support and then released from the solid support upon application of a stimulus, which allows the nucleic acid barcode molecules to dissociate or to be released from the solid support. In specific examples, nucleic acid barcode molecules are initially associated with the solid support (e.g., bead) and then released from the solid support upon application of a biological stimulus, a chemical stimulus, a thermal stimulus, an electrical stimulus, a magnetic stimulus, and/or a photo stimulus.

A nucleic acid barcode molecule may contain a barcode sequence and a functional sequence, such as a nucleic acid primer sequence or a template switch oligonucleotide (TSO) sequence.

The solid support may be a bead. A solid support, e.g., a bead, may be porous, non-porous, hollow (e.g., a microcapsule), solid, semi-solid, and/or a combination thereof. Beads may be solid, semi-solid, semi-fluidic, fluidic, and/or a combination thereof. In some instances, a solid support, e.g., a bead, may be dissolvable, disruptable, and/or degradable. In some cases, a solid support, e.g., a bead, may not be degradable. In some cases, the solid support, e.g., a bead, may be a gel bead. A gel bead may be a hydrogel bead. A gel bead may be formed from molecular precursors, such as a polymeric or monomeric species. A semi-solid support, e.g., a bead, may be a liposomal bead. Solid supports, e.g., beads, may comprise metals including iron oxide, gold, and silver. In some cases, the solid support, e.g., the bead, may be a silica bead. In some cases, the solid support, e.g., a bead, can be rigid. In other cases, the solid support, e.g., a bead, may be flexible and/or compressible.

A partition may comprise one or more unique identifiers, such as barcodes. Barcodes may be previously, subsequently or concurrently delivered to the partitions that hold the compartmentalized or partitioned analyte carrier. For example, barcodes may be injected into droplets or deposited in microwells previous to, subsequent to, or concurrently with droplet generation or providing of reagents in the microwells, respectively. The delivery of the barcodes to a particular partition allows for the later attribution of the characteristics of the individual analyte carrier to the particular partition. Barcodes may be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can comprise a bead. Beads are described in further detail below.

In some cases, barcoded nucleic acid molecules can be initially associated with the microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus may disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

FIG. 2 shows an example of a microfluidic channel structure 200 for delivering barcode carrying beads to droplets. The channel structure 200 can include channel segments 201, 202, 204, 206 and 208 communicating at a channel junction 210. In operation, the channel segment 201 may transport an aqueous fluid 212 that includes a plurality of beads 214 (e.g., with nucleic acid molecules, oligonucleotides, molecular tags) along the channel segment 201 into junction 210. The plurality of beads 214 may be sourced from a suspension of beads. For example, the channel segment 201 may be connected to a reservoir comprising an aqueous suspension of beads 214. The channel segment 202 may transport the aqueous fluid 212 that includes a plurality of analyte carriers 216 along the channel segment 202 into junction 210. The plurality of biological particles 216 may be sourced from a suspension of analyte carriers. For example, the channel segment 202 may be connected to a reservoir comprising an aqueous suspension of analyte carriers 216. In some instances, the aqueous fluid 212 in either the first channel segment 201 or the second channel segment 202, or in both segments, can include one or more reagents, as further described below. A second fluid 218 that is immiscible with the aqueous fluid 212 (e.g., oil) can be delivered to the junction 210 from each of channel segments 204 and 206. Upon meeting of the aqueous fluid 212 from each of channel segments 201 and 202 and the second fluid 218 from each of channel segments 204 and 206 at the channel junction 210, the aqueous fluid 212 can be partitioned as discrete droplets 220 in the second fluid 218 and flow away from the junction 210 along channel segment 208. The channel segment 208 may deliver the discrete droplets to an outlet reservoir fluidly coupled to the channel segment 208, where they may be harvested.

As an alternative, the channel segments 201 and 202 may meet at another junction upstream of the junction 210. At such junction, beads and analyte carriers may form a mixture that is directed along another channel to the junction 210 to yield droplets 220. The mixture may provide the beads and analyte carriers in an alternating fashion, such that, for example, a droplet comprises a single bead and a single analyte carrier.

Beads, analyte carriers and droplets may flow along channels at substantially regular flow profiles (e.g., at regular flow rates). Such regular flow profiles may permit a droplet to include a single bead and a single analyte carrier. Such regular flow profiles may permit the droplets to have an occupancy (e.g., droplets having beads and analyte carriers) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

The second fluid 218 can comprise an oil, such as a fluorinated oil, that includes a fluorosurfactant for stabilizing the resulting droplets, for example, inhibiting subsequent coalescence of the resulting droplets 220.

A discrete droplet that is generated may include an individual analyte carrier 216. A discrete droplet that is generated may include a barcode or other reagent carrying bead 214. A discrete droplet generated may include both an individual analyte carrier and a barcode carrying bead, such as droplets 220. In some instances, a discrete droplet may include more than one individual analyte carrier or no analyte carrier. In some instances, a discrete droplet may include more than one bead or no bead. A discrete droplet may be unoccupied (e.g., no beads, no analyte carriers).

Beneficially, a discrete droplet partitioning an analyte carrier and a barcode carrying bead may effectively allow the attribution of the barcode to macromolecular constituents of the analyte carrier within the partition. The contents of a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 200 may have other geometries. For example, a microfluidic channel structure can have more than one channel junctions. For example, a microfluidic channel structure can have 2, 3, 4, or 5 channel segments each carrying beads that meet at a channel junction. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

A bead may be porous, non-porous, solid, semi-solid, semi-fluidic, fluidic, and/or a combination thereof. In some instances, a bead may be dissolvable, disruptable, and/or degradable. In some cases, a bead may not be degradable. In some cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

A bead may be of any suitable shape. Examples of bead shapes include, but are not limited to, spherical, non-spherical, oval, oblong, amorphous, circular, cylindrical, and variations thereof.

Beads may be of uniform size or heterogeneous size. In some cases, the diameter of a bead may be at least about 10 nanometers (nm), 100 nm, 500 nm, 1 micrometer ($\mu m$), 5 $\mu m$, 10 $\mu m$, 20 $\mu m$, 30 $\mu m$, 40 $\mu m$, 50 $\mu m$, 60 $\mu m$, 70 $\mu m$, 80 $\mu m$, 90 $\mu m$, 100 $\mu m$, 250 $\mu m$, 500 $\mu m$, 1 mm, or greater. In some cases, a bead may have a diameter of less than about 10 nm, 100 nm, 500 nm, 1 $\mu m$, 5 $\mu m$, 10 $\mu m$, 20 $\mu m$, 30 $\mu m$, 40 $\mu m$, 50 $\mu m$, 60 $\mu m$, 70 $\mu m$, 80 $\mu m$, 90 $\mu m$, 100 $\mu m$, 250 $\mu m$, 500 $\mu m$, 1 mm, or less. In some cases, a bead may have a diameter in the range of about 40-75 $\mu m$, 30-75 $\mu m$, 20-75 $\mu m$, 40-85 $\mu m$, 40-95 $\mu m$, 20-100 $\mu m$, 10-100 $\mu m$, 1-100 $\mu m$, 20-250 $\mu m$, or 20-500 $\mu m$.

In certain aspects, beads can be provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

A bead may comprise natural and/or synthetic materials. For example, a bead can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly (vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some instances, the bead may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers. In some cases, the bead may comprise covalent or ionic bonds between polymeric precursors (e.g., monomers, oligomers, linear polymers), nucleic acid molecules (e.g., oligonucleotides), primers, and other entities. In some cases, the covalent bonds can be carbon-carbon bonds, thioether bonds, or carbon-heteroatom bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

In some cases, disulfide linkages can be formed between molecular precursor units (e.g., monomers, oligomers, or linear polymers) or precursors incorporated into a bead and nucleic acid molecules (e.g., oligonucleotides). Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some cases, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some cases, a bead may comprise an acrydite moiety, which in certain aspects may be used to attach one or more nucleic acid molecules (e.g., barcode sequence, barcoded nucleic acid molecule, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as a nucleic acid molecule (e.g., barcode sequence, barcoded nucleic acid molecule, barcoded oligonucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment can be reversible, such that when the disulfide bond is broken (e.g., in the presence of a reducing agent), the attached species is released from the bead. In other cases, an acrydite moiety can comprise a reactive hydroxyl group that may be used for attachment.

Functionalization of beads for attachment of nucleic acid molecules (e.g., oligonucleotides) may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule (e.g., oligonucleotide) that comprises one or more functional sequences, such as a TSO sequence or a primer sequence (e.g., a poly T sequence, or a nucleic acid primer sequence complementary to a target nucleic acid sequence and/or for amplifying a target nucleic acid sequence, a random primer, or a primer sequence for messenger RNA) that is useful for incorporation into the bead and/or one or more barcode sequences. The one or more barcode sequences may include sequences that are the same for all nucleic acid molecules coupled to a given bead and/or sequences that are different across all nucleic acid molecules coupled to the given bead. The nucleic acid molecule may be incorporated into the bead.

In some cases, the nucleic acid molecule can comprise a functional sequence, for example, for attachment to a sequencing flow cell, such as, for example, a P5 sequence (or a portion thereof) for Illumina® sequencing. In some cases, the nucleic acid molecule or derivative thereof (e.g., oligonucleotide or polynucleotide generated from the nucleic acid molecule) can comprise another functional sequence, such as, for example, a P7 sequence (or a portion thereof) for attachment to a sequencing flow cell for Illumina sequencing. In some cases, the nucleic acid molecule can comprise a barcode sequence. In some cases, the nucleic acid molecule can further comprise a unique molecular identifier (UMI). In some cases, the nucleic acid molecule can comprise an R1 primer sequence for Illumina sequencing. In some cases, the nucleic acid molecule can comprise an R2 primer sequence for Illumina sequencing. In some cases, a functional sequence can comprise a partial sequence, such as a partial barcode sequence, partial anchoring sequence, partial sequencing primer sequence (e.g., partial R1 sequence, partial R2 sequence, etc.), a partial sequence configured to attach to the flow cell of a sequencer (e.g., partial P5 sequence, partial P7 sequence, etc.), or a partial sequence of any other type of sequence described elsewhere herein. A partial sequence may contain a contiguous or continuous portion or segment, but not all, of a full sequence, for example. In some cases, a downstream procedure may extend the partial sequence, or derivative thereof, to achieve a full sequence of the partial sequence, or derivative thereof.

Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

Figure 8:
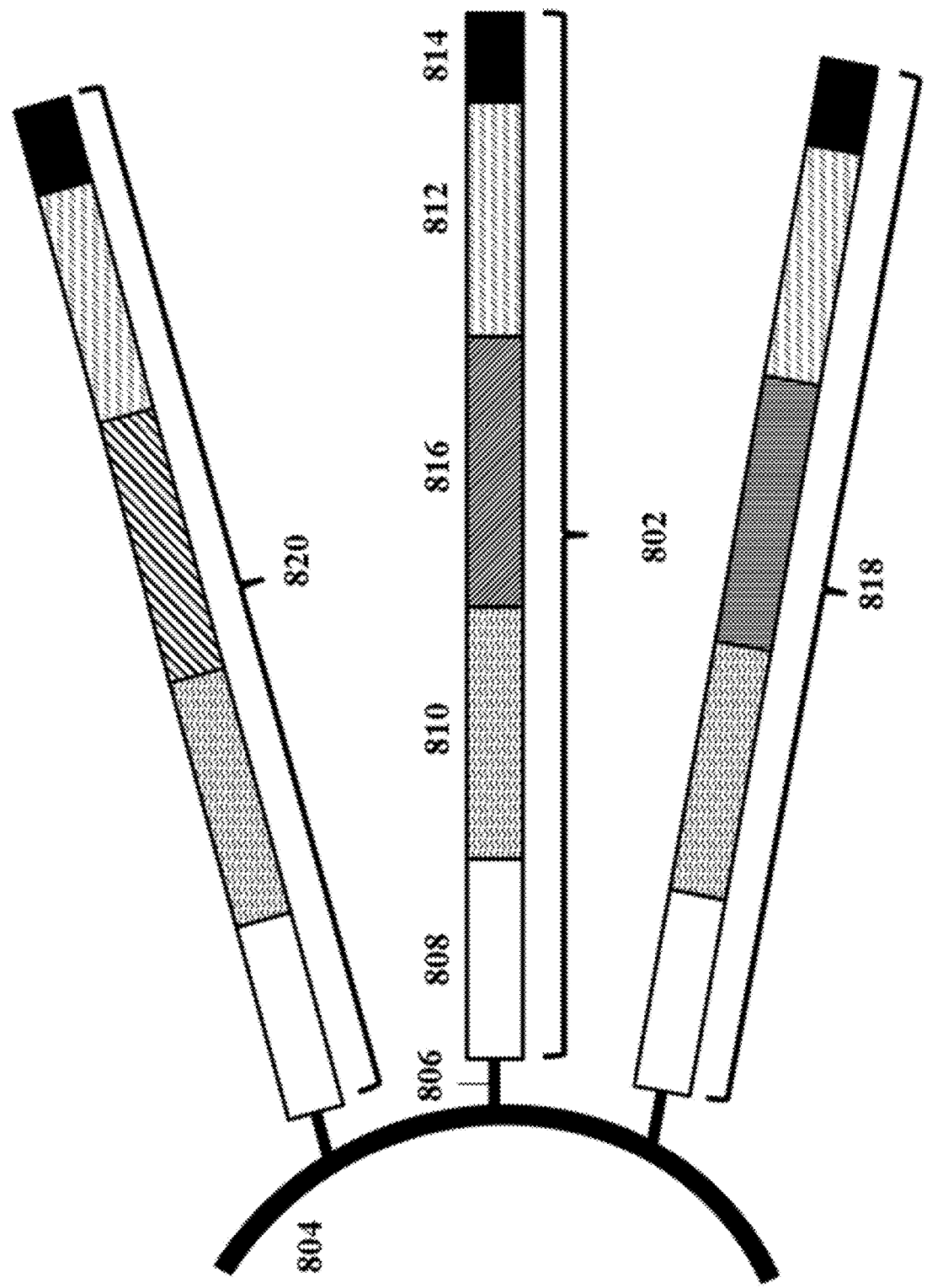
FIG. 8 illustrates an example of a barcode carrying bead.

FIG. 8 illustrates an example of a barcode carrying bead. A nucleic acid molecule 802, such as an oligonucleotide, can be coupled to a bead 804 by a releasable linkage 806, such as, for example, a disulfide linker. The same bead 804 may be coupled (e.g., via releasable linkage) to one or more other nucleic acid molecules 818, 820. The nucleic acid molecule 802 may be or comprise a barcode. As noted elsewhere herein, the structure of the barcode may comprise a number of sequence elements. The nucleic acid molecule 802 may comprise a functional sequence 808 that may be used in subsequent processing. For example, the functional sequence 808 may include one or more of a sequencer specific flow cell attachment sequence (e.g., a P5 sequence for Illumina® sequencing systems) and a sequencing primer sequence (e.g., a R1 primer for Illumina® sequencing systems, or partial sequence(s) thereof). The nucleic acid molecule 802 may comprise a barcode sequence 810 for use in barcoding the sample (e.g., DNA, RNA, protein, etc.). In some cases, the barcode sequence 810 can be bead-specific such that the barcode sequence 810 is common to all nucleic acid molecules (e.g., including nucleic acid molecule 802) coupled to the same bead 804. Alternatively or in addition, the barcode sequence 810 can be partition-specific such that the barcode sequence 810 is common to all nucleic acid molecules coupled to one or more beads that are partitioned into the same partition. The nucleic acid molecule 802 may comprise a specific priming sequence 812, such as an mRNA specific priming sequence (e.g., poly-T sequence), a targeted priming sequence, and/or a random priming sequence. The nucleic acid molecule 802 may comprise an anchoring sequence 814 to ensure that the specific priming sequence 812 hybridizes at the sequence end (e.g., of the mRNA). For example, the anchoring sequence 814 can include a random short sequence of nucleotides, such as a 1-mer, 2-mer, 3-mer or longer sequence, which can ensure that a poly-T segment is more likely to hybridize at the sequence end of the poly-A tail of the mRNA.

The nucleic acid molecule 802 may comprise a unique molecular identifying sequence 816 (e.g., unique molecular identifier (UMI)). In some cases, the unique molecular identifying sequence 816 may comprise from about 5 to about 8 nucleotides. Alternatively, the unique molecular identifying sequence 816 may compress less than about 5 or more than about 8 nucleotides. The unique molecular identifying sequence 816 may be a unique sequence that varies across individual nucleic acid molecules (e.g., 802, 818, 820, etc.) coupled to a single bead (e.g., bead 804). In some cases, the unique molecular identifying sequence 816 may be a random sequence (e.g., such as a random N-mer sequence). For example, the UMI may provide a unique identifier of the starting mRNA molecule that was captured, in order to allow quantitation of the number of original expressed RNA. As will be appreciated, although FIG. 8 shows three nucleic acid molecules 802, 818, 820 coupled to the surface of the bead 804, an individual bead may be coupled to any number of individual nucleic acid molecules, for example, from one to tens to hundreds of thousands or even millions of individual nucleic acid molecules. The respective barcodes for the individual nucleic acid molecules can comprise both common sequence segments or relatively common sequence segments (e.g., 808, 810, 812, etc.) and variable or unique sequence segments (e.g., 816) between different individual nucleic acid molecules coupled to the same bead.

In operation, an analyte carrier (e.g., cell, DNA, RNA, etc.) can be co-partitioned along with a barcode bearing bead 804. The barcoded nucleic acid molecules 802, 818, 820 can be released from the bead 804 in the partition. By way of example, in the context of analyzing sample RNA, the poly-T segment (e.g., 812) of one of the released nucleic acid molecules (e.g., 802) can hybridize to the poly-A tail of a mRNA molecule. Reverse transcription may result in a cDNA transcript of the mRNA, but which transcript includes each of the sequence segments 808, 810, 816 of the nucleic acid molecule 802. Because the nucleic acid molecule 802 comprises an anchoring sequence 814, it will more likely hybridize to and prime reverse transcription at the sequence end of the poly-A tail of the mRNA. Within any given partition, all of the cDNA transcripts of the individual mRNA molecules may include a common barcode sequence segment 810. However, the transcripts made from the different mRNA molecules within a given partition may vary at the unique molecular identifying sequence 812 segment (e.g., UMI segment). Beneficially, even following any subsequent amplification of the contents of a given partition, the number of different UMIs can be indicative of the quantity of mRNA originating from a given partition, and thus from the analyte carrier (e.g., cell). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell contents. In such cases, further processing may be performed, in the partitions or outside the partitions (e.g., in bulk). For instance, the RNA molecules on the beads may be subjected to reverse transcription or other nucleic acid processing, additional adapter sequences may be added to the barcoded nucleic acid molecules, or other nucleic acid reactions (e.g., amplification, nucleic acid extension) may be performed. The beads or products thereof (e.g., barcoded nucleic acid molecules) may be collected from the partitions, and/or pooled together and subsequently subjected to clean up and further characterization (e.g., sequencing).

The operations described herein may be performed at any useful or convenient step. For instance, the beads comprising nucleic acid barcode molecules may be introduced into a partition (e.g., well or droplet) prior to, during, or following introduction of a sample into the partition. The nucleic acid molecules of a sample may be subjected to barcoding, which may occur on the bead (in cases where the nucleic acid molecules remain coupled to the bead) or following release of the nucleic acid barcode molecules into the partition. In cases where the nucleic acid molecules from the sample remain attached to the bead, the beads from various partitions may be collected, pooled, and subjected to further processing (e.g., reverse transcription, adapter attachment, amplification, clean up, sequencing). In other instances, the processing may occur in the partition. For example, conditions sufficient for barcoding, adapter attachment, reverse transcription, or other nucleic acid processing operations may be provided in the partition and performed prior to clean up and sequencing.

In some instances, a bead may comprise a capture sequence or binding sequence configured to bind to a corresponding capture sequence or binding sequence. In some instances, a bead may comprise a plurality of different capture sequences or binding sequences configured to bind to different respective corresponding capture sequences or binding sequences. For example, a bead may comprise a first subset of one or more capture sequences each configured to bind to a first corresponding capture sequence, a second subset of one or more capture sequences each configured to bind to a second corresponding capture sequence, a third subset of one or more capture sequences each configured to bind to a third corresponding capture sequence, and etc. A bead may comprise any number of different capture sequences. In some instances, a bead may comprise at least 2, 3, 4, 5, 6, 7, 8, 9, 10 or more different capture sequences or binding sequences configured to bind to different respective capture sequences or binding sequences, respectively. Alternatively or in addition, a bead may comprise at most about 10, 9, 8, 7, 6, 5, 4, 3, or 2 different capture sequences or binding sequences configured to bind to different respective capture sequences or binding sequences. In some instances, the different capture sequences or binding sequences may be configured to facilitate analysis of a same type of analyte. In some instances, the different capture sequences or binding sequences may be configured to facilitate analysis of different types of analytes (with the same bead). The capture sequence may be designed to attach to a corresponding capture sequence. Beneficially, such corresponding capture sequence may be introduced to, or otherwise induced in, a biological particle (e.g., cell, cell bead, etc.) for performing different assays in various formats (e.g., barcoded antibodies comprising the corresponding capture sequence, barcoded MHC dextramers comprising the corresponding capture sequence, barcoded guide RNA molecules comprising the corresponding capture sequence, etc.), such that the corresponding capture sequence may later interact with the capture sequence associated with the bead. In some instances, a capture sequence coupled to a bead (or other support) may be configured to attach to a linker molecule, such as a splint molecule, wherein the linker molecule is configured to couple the bead (or other support) to other molecules through the linker molecule, such as to one or more analytes or one or more other linker molecules.

Figure 9:
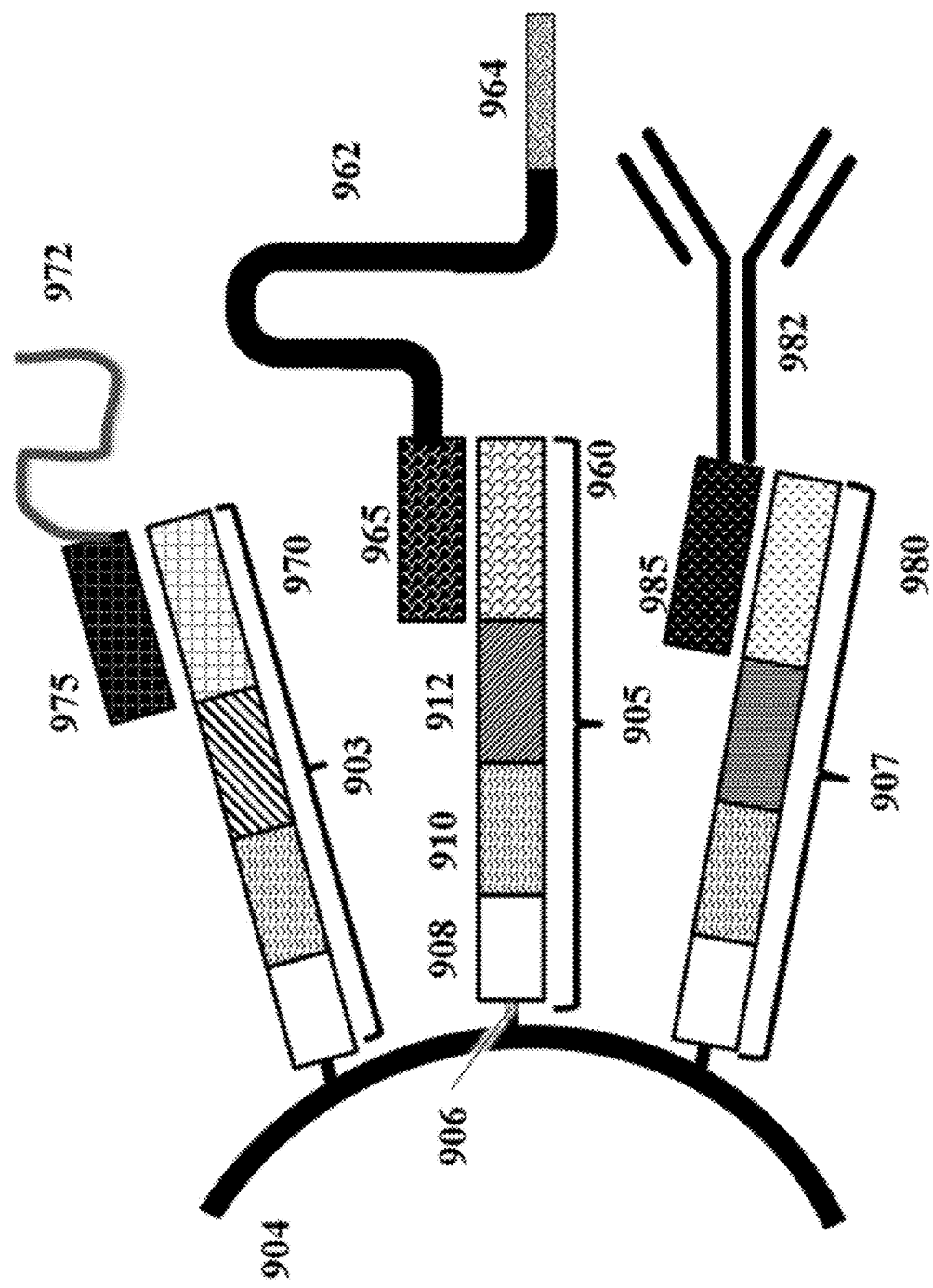
FIG. 9 illustrates another example of a barcode carrying bead.

FIG. 9 illustrates another example of a barcode carrying bead. A nucleic acid molecule 905, such as an oligonucleotide, can be coupled to a bead 904 by a releasable linkage 906, such as, for example, a disulfide linker. The nucleic acid molecule 905 may comprise a first capture sequence 960. The same bead 904 may be coupled (e.g., via releasable linkage) to one or more other nucleic acid molecules 903, 907 comprising other capture sequences. The nucleic acid molecule 905 may be or comprise a barcode. As noted elsewhere herein, the structure of the barcode may comprise a number of sequence elements, such as a functional sequence 908 (e.g., flow cell attachment sequence, sequencing primer sequence, etc.), a barcode sequence 910 (e.g., bead-specific sequence common to bead, partition-specific sequence common to partition, etc.), and a unique molecular identifier 912 (e.g., unique sequence within different molecules attached to the bead), or partial sequences thereof. The capture sequence 960 may be configured to attach to a corresponding capture sequence 965. In some instances, the corresponding capture sequence 965 may be coupled to another molecule that may be an analyte or an intermediary carrier. For example, as illustrated in FIG. 9, the corresponding capture sequence 965 is coupled to a guide RNA molecule 962 comprising a target sequence 964, wherein the target sequence 964 is configured to attach to the analyte. Another oligonucleotide molecule 907 attached to the bead 904 comprises a second capture sequence 980 which is configured to attach to a second corresponding capture sequence 985. As illustrated in FIG. 9, the second corresponding capture sequence 985 is coupled to an antibody 982. In some cases, the antibody 982 may have binding specificity to an analyte (e.g., surface protein). Alternatively, the antibody 982 may not have binding specificity. Another oligonucleotide molecule 903 attached to the bead 904 comprises a third capture sequence 970 which is configured to attach to a second corresponding capture sequence 975. As illustrated in FIG. 9, the third corresponding capture sequence 975 is coupled to a molecule 972. The molecule 972 may or may not be configured to target an analyte. The other oligonucleotide molecules 903, 907 may comprise the other sequences (e.g., functional sequence, barcode sequence, UMI, etc.) described with respect to oligonucleotide molecule 905. While a single oligonucleotide molecule comprising each capture sequence is illustrated in FIG. 9, it will be appreciated that, for each capture sequence, the bead may comprise a set of one or more oligonucleotide molecules each comprising the capture sequence. For example, the bead may comprise any number of sets of one or more different capture sequences. Alternatively or in addition, the bead 904 may comprise other capture sequences. Alternatively or in addition, the bead 904 may comprise fewer types of capture sequences (e.g., two capture sequences). Alternatively or in addition, the bead 904 may comprise oligonucleotide molecule(s) comprising a priming sequence, such as a specific priming sequence such as an mRNA specific priming sequence (e.g., poly-T sequence), a targeted priming sequence, and/or a random priming sequence, for example, to facilitate an assay for gene expression.

In operation, the barcoded oligonucleotides may be released (e.g., in a partition), as described elsewhere herein. Alternatively, the nucleic acid molecules bound to the bead (e.g., gel bead) may be used to hybridize and capture analytes (e.g., one or more types of analytes) on the solid phase of the bead.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmalieamide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent:gel bead ratios of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, less than or equal to about 1:10,000) of reducing agent may be used for reduction. Controlling the number of disulfide linkages that are reduced to free thiols may be useful in ensuring bead structural integrity during functionalization. In some cases, optically-active agents, such as fluorescent dyes may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

A bead injected or otherwise introduced into a partition may comprise releasably, cleavably, or reversibly attached barcodes. A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degradation of the underlying bead itself, allowing the barcodes to be accessed or be accessible by other reagents, or both. In non-limiting examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, such as described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to, or as an alternative to the cleavable linkages between the beads and the associated molecules, such as barcode containing nucleic acid molecules (e.g., barcoded oligonucleotides), the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead can be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a nucleic acid molecule, e.g., barcoded oligonucleotide) may result in release of the species from the bead.

As will be appreciated from the above disclosure, the degradation of a bead may refer to the disassociation of a bound or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by various de-swelling methods. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to a precursor, another species linked to a precursor, or a precursor itself can comprise a labile bond, such as chemically, thermally, or photo-sensitive bond e.g., disulfide bond, UV sensitive bond, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, enzymatic, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

In some cases, a species (e.g., oligonucleotide molecules comprising barcodes) that are attached to a solid support (e.g., a bead) may comprise a U-excising element that allows the species to release from the bead. In some cases, the U-excising element may comprise a single-stranded DNA (ssDNA) sequence that contains at least one uracil. The species may be attached to a solid support via the ssDNA sequence containing the at least one uracil. The species may be released by a combination of uracil-DNA glycosylase (e.g., to remove the uracil) and an endonuclease (e.g., to induce an ssDNA break). If the endonuclease generates a 5' phosphate group from the cleavage, then additional enzyme treatment may be included in downstream processing to eliminate the phosphate group, e.g., prior to ligation of additional sequencing handle elements, e.g., Illumina full P5 sequence, partial P5 sequence, full R1 sequence, and/or partial R1 sequence.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)). A bond may be cleavable via other nucleic acid molecule targeting enzymes, such as restriction enzymes (e.g., restriction endonucleases), as described further below.

Species may be encapsulated in beads during bead generation (e.g., during polymerization of precursors). Such species may or may not participate in polymerization. Such species may be entered into polymerization reaction mixtures such that generated beads comprise the species upon bead formation. In some cases, such species may be added to the gel beads after formation. Such species may include, for example, nucleic acid molecules (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such species may include one or more enzymes described herein, including without limitation, polymerase, reverse transcriptase, restriction enzymes (e.g., endonuclease), transposase, ligase, proteinase K, DNAse, etc. Such species may include one or more reagents described elsewhere herein (e.g., lysis agents, inhibitors, inactivating agents, chelating agents, stimulus). Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead. Alternatively or in addition, species may be partitioned in a partition (e.g., droplet) during or subsequent to partition formation. Such species may include, without limitation, the abovementioned species that may also be encapsulated in a bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., a nucleic acid molecule, a barcode sequence, a primer, etc) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it may be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads comprise reducible cross-linking groups, such as disulfide groups, it will be desirable to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than about 1/10th, less than about 1/50th, or even less than about 1/100th of the lower ranges for such materials used in degrading the beads. For example, for DTT, the reducing agent free preparation can have less than about 0.01 millimolar (mM), 0.005 mM, 0.001 mM DTT, 0.0005 mM DTT, or even less than about 0.0001 mM DTT. In many cases, the amount of DTT can be undetectable.

Numerous chemical triggers may be used to trigger the degradation of beads. Examples of these chemical changes may include, but are not limited to pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead. In some cases, any combination of stimuli may trigger degradation of a bead. For example, a change in pH may enable a chemical agent (e.g., DTT) to become an effective reducing agent.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

Any suitable agent may degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, 10 mM. The reducing agent may be present at a concentration of at least about 0.1 mM, 0.5 mM, 1 mM, 5 mM, 10 mM, or greater than 10 mM. The reducing agent may be present at concentration of at most about 10 mM, 5 mM, 1 mM, 0.5 mM, 0.1 mM, or less.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing oligonucleotide bearing beads.

Although FIG. 1 and FIG. 2 have been described in terms of providing substantially singly occupied partitions, above, in certain cases, it may be desirable to provide multiply occupied partitions, e.g., containing two, three, four or more cells and/or microcapsules (e.g., beads) comprising barcoded nucleic acid molecules (e.g., oligonucleotides) within a single partition. Accordingly, as noted above, the flow characteristics of the analyte carrier and/or bead containing fluids and partitioning fluids may be controlled to provide for such multiply occupied partitions. In particular, the flow parameters may be controlled to provide a given occupancy rate at greater than about 50% of the partitions, greater than about 75%, and in some cases greater than about 80%, 90%, 95%, or higher.

In some cases, additional microcapsules can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction (e.g., junction 210). In such cases, the flow and frequency of the different beads into the channel or junction may be controlled to provide for a certain ratio of microcapsules from each source, while ensuring a given pairing or combination of such beads into a partition with a given number of analyte carriers (e.g., one analyte carrier and one bead per partition).

The partitions described herein may comprise small volumes, for example, less than about 10 microliters (μL), 5 μL, 1 μL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

For example, in the case of droplet based partitions, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where co-partitioned with microcapsules, it will be appreciated that the sample fluid volume, e.g., including co-partitioned analyte carriers and/or beads, within the partitions may be less than about 90% of the above described volumes, less than about 80%, less than about 70%, less than about 60%, less than about 50%, less than about 40%, less than about 30%, less than about 20%, or less than about 10% of the above described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions.

Reagents

In accordance with certain aspects, analyte carriers may be partitioned along with lysis reagents in order to release the contents of the analyte carriers within the partition. In such cases, the lysis agents can be contacted with the analyte carrier suspension concurrently with, or immediately prior to, the introduction of the analyte carriers into the partitioning junction/droplet generation zone (e.g., junction 210), such as through an additional channel or channels upstream of the channel junction. In accordance with other aspects, additionally or alternatively, analyte carriers may be partitioned along with other reagents, as will be described further below.

Figure 3:
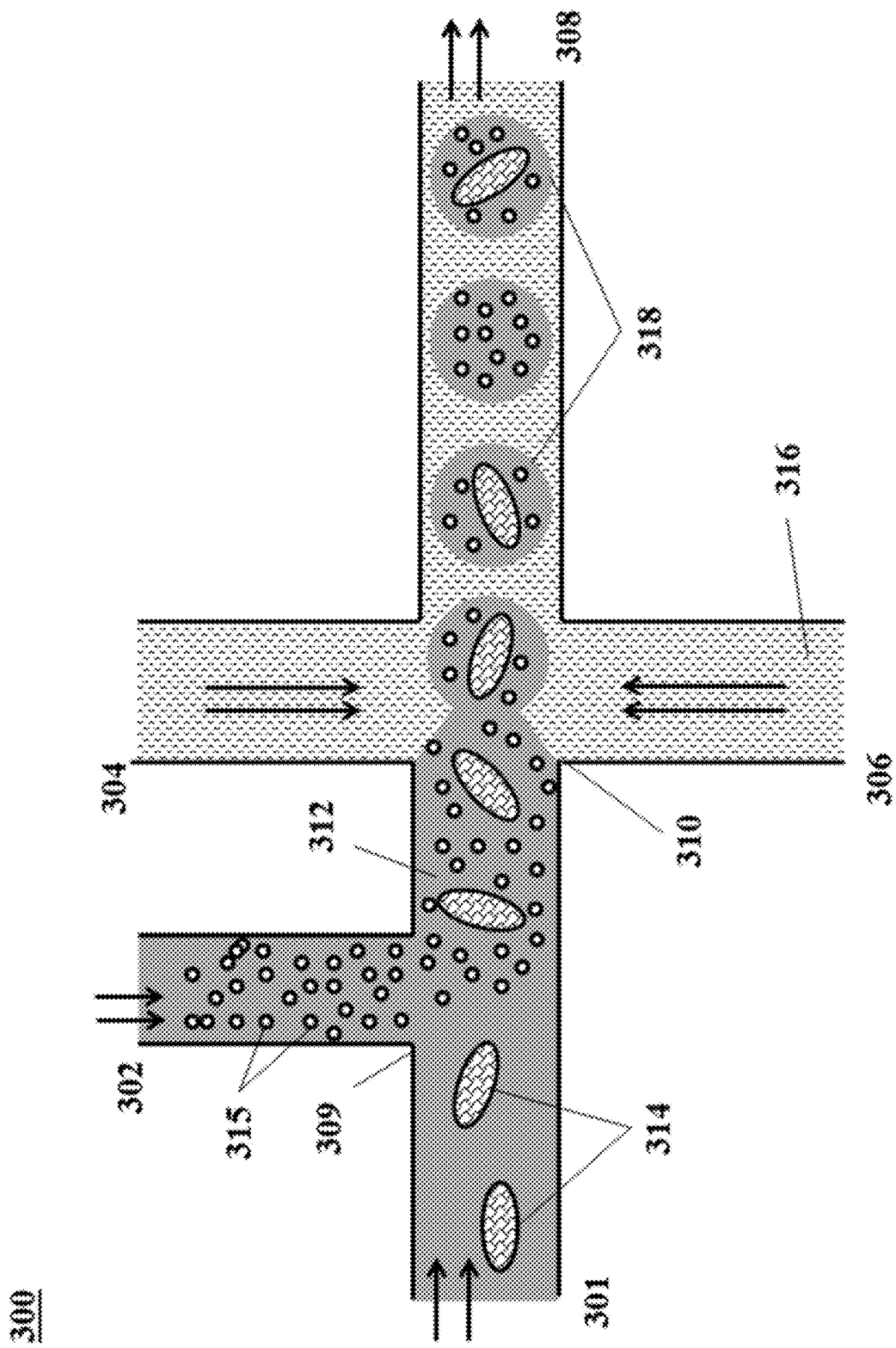
FIG. 3 shows an example of a microfluidic channel structure for co-partitioning analyte carriers and reagents.

FIG. 3 shows an example of a microfluidic channel structure 300 for co-partitioning analyte carriers and reagents. The channel structure 300 can include channel segments 301, 302, 304, 306 and 308. Channel segments 301 and 302 communicate at a first channel junction 309. Channel segments 302, 304, 306, and 308 communicate at a second channel junction 310.

In an example operation, the channel segment 301 may transport an aqueous fluid 312 that includes a plurality of analyte carriers 314 along the channel segment 301 into the second junction 310. As an alternative or in addition to, channel segment 301 may transport beads (e.g., gel beads). The beads may comprise barcode molecules.

For example, the channel segment 301 may be connected to a reservoir comprising an aqueous suspension of analyte carriers 314. Upstream of, and immediately prior to reaching, the second junction 310, the channel segment 301 may meet the channel segment 302 at the first junction 309. The channel segment 302 may transport a plurality of reagents 315 (e.g., lysis agents) suspended in the aqueous fluid 312 along the channel segment 302 into the first junction 309. For example, the channel segment 302 may be connected to a reservoir comprising the reagents 315. After the first junction 309, the aqueous fluid 312 in the channel segment 301 can carry both the analyte carriers 314 and the reagents 315 towards the second junction 310. In some instances, the aqueous fluid 312 in the channel segment 301 can include one or more reagents, which can be the same or different reagents as the reagents 315. A second fluid 316 that is immiscible with the aqueous fluid 312 (e.g., oil) can be delivered to the second junction 310 from each of channel segments 304 and 306. Upon meeting of the aqueous fluid 312 from the channel segment 301 and the second fluid 316 from each of channel segments 304 and 306 at the second channel junction 310, the aqueous fluid 312 can be partitioned as discrete droplets 318 in the second fluid 316 and flow away from the second junction 310 along channel segment 308. The channel segment 308 may deliver the discrete droplets 318 to an outlet reservoir fluidly coupled to the channel segment 308, where they may be harvested.

The second fluid 316 can comprise an oil, such as a fluorinated oil, that includes a fluorosurfactant for stabilizing the resulting droplets, for example, inhibiting subsequent coalescence of the resulting droplets 318.

A discrete droplet generated may include an individual analyte carrier 314 and/or one or more reagents 315. In some instances, a discrete droplet generated may include a barcode carrying bead (not shown), such as via other microfluidics structures described elsewhere herein. In some instances, a discrete droplet may be unoccupied (e.g., no reagents, no analyte carriers).

Beneficially, when lysis reagents and analyte carriers are co-partitioned, the lysis reagents can facilitate the release of the contents of the analyte carriers within the partition. The contents released in a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 300 may have other geometries. For example, a microfluidic channel structure can have more than two channel junctions. For example, a microfluidic channel structure can have 2, 3, 4, 5 channel segments or more each carrying the same or different types of beads, reagents, and/or analyte carriers that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Other lysis agents may additionally or alternatively be co-partitioned with the analyte carriers to cause the release of the analyte carriers's contents into the partitions. For example, in some cases, surfactant-based lysis solutions may be used to lyse cells, although these may be less desirable for emulsion based systems where the surfactants can interfere with stable emulsions. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion based partitioning such as encapsulation of analyte carriers that may be in addition to or in place of droplet partitioning, where any pore size of the encapsulate is sufficiently small to retain nucleic acid fragments of a given size, following cellular disruption.

Alternatively or in addition to the lysis agents co-partitioned with the analyte carriers described above, other reagents can also be co-partitioned with the analyte carriers, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated analyte carriers (e.g., a cell or a nucleus in a polymer matrix), the analyte carriers may be exposed to an appropriate stimulus to release the analyte carriers or their contents from a co-partitioned microcapsule. For example, in some cases, a chemical stimulus may be co-partitioned along with an encapsulated analyte carrier to allow for the degradation of the microcapsule and release of the cell or its contents into the larger partition. In some cases, this stimulus may be the same as the stimulus described elsewhere herein for release of nucleic acid molecules (e.g., oligonucleotides) from their respective microcapsule (e.g., bead). In alternative examples, this may be a different and non-overlapping stimulus, in order to allow an encapsulated analyte carrier to be released into a partition at a different time from the release of nucleic acid molecules into the same partition. For a description of methods, compositions, and systems for encapsulating cells (also referred to as a "cell bead"), see, e.g., U.S. Pat. No. 10,428,326 and U.S. Pat. Pub. 20190100632, which are each incorporated by reference in their entirety.

Additional reagents may also be co-partitioned with the analyte carrier, such as endonucleases to fragment an analyte carrier's DNA, DNA polymerase enzymes and dNTPs used to amplify the analyte carrier's nucleic acid fragments and to attach the barcode molecular tags to the amplified fragments. Other enzymes may be co-partitioned, including without limitation, polymerase, transposase, ligase, proteinase K, DNAse, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective partitions, the macromolecular components (e.g., macromolecular constituents of analyte carriers, such as RNA, DNA, or proteins) contained therein may be further processed within the partitions. In accordance with the methods and systems described herein, the macromolecular component contents of individual analyte carriers can be provided with unique identifiers such that, upon characterization of those macromolecular components they may be attributed as having been derived from the same analyte carrier or particles. The ability to attribute characteristics to individual analyte carriers or groups of analyte carriers is provided by the assignment of unique identifiers specifically to an individual analyte carrier or groups of analyte carriers. Unique identifiers, e.g., in the form of nucleic acid barcodes can be assigned or associated with individual analyte carriers or populations of analyte carriers, in order to tag or label the analyte carrier's macromolecular components (and as a result, its characteristics) with the unique identifiers. These unique identifiers can then be used to attribute the analyte carrier's components and characteristics to an individual analyte carrier or group of analyte carriers.

In some aspects, this is performed by co-partitioning the individual analyte carrier or groups of analyte carriers with the unique identifiers, such as described above (with reference to FIG. 2). In some aspects, the unique identifiers are provided in the form of nucleic acid molecules (e.g., oligonucleotides) that comprise nucleic acid barcode sequences that may be attached to or otherwise associated with the nucleic acid contents of individual analyte carrier, or to other components of the analyte carrier, and particularly to fragments of those nucleic acids. The nucleic acid molecules are partitioned such that as between nucleic acid molecules in a given partition, the nucleic acid barcode sequences contained therein are the same, but as between different partitions, the nucleic acid molecule can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from about 6 to about 20 or more nucleotides within the sequence of the nucleic acid molecules (e.g., oligonucleotides). The nucleic acid barcode sequences can include from about 6 to about 20, 30, 40, 50, 60, 70, 80, 90, 100 or more nucleotides. In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

The co-partitioned nucleic acid molecules can also comprise other functional sequences useful in the processing of the nucleic acids from the co-partitioned analyte carriers. These sequences include, e.g., targeted or random/universal amplification primer sequences for amplifying nucleic acids (e.g., mRNA, genomic DNA) from the individual analyte carriers within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides (e.g., attached to a bead) into partitions, e.g., droplets within microfluidic systems.

In an example, microcapsules, such as beads, are provided that each include large numbers of the above described barcoded nucleic acid molecules (e.g., barcoded oligonucleotides) releasably attached to the beads, where all of the nucleic acid molecules attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of nucleic acid (e.g., oligonucleotide) molecules attached. In particular, the number of molecules of nucleic acid molecules including the barcode sequence on an individual bead can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules, or more. Nucleic acid molecules of a given bead can include identical (or common) barcode sequences, different barcode sequences, or a combination of both. Nucleic acid molecules of a given bead can include multiple sets of nucleic acid molecules. Nucleic acid molecules of a given set can include identical barcode sequences. The identical barcode sequences can be different from barcode sequences of nucleic acid molecules of another set.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules.

In some cases, it may be desirable to incorporate multiple different barcodes within a given partition, either attached to a single or multiple beads within the partition. For example, in some cases, a mixed, but known set of barcode sequences may provide greater assurance of identification in the subsequent processing, e.g., by providing a stronger address or attribution of the barcodes to a given partition, as a duplicate or independent confirmation of the output from a given partition.

The nucleic acid molecules (e.g., oligonucleotides) are releasable from the beads upon the application of a particular stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules form the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of analyte carriers and may be degraded for release of the attached nucleic acid molecules through exposure to a reducing agent, such as DTT.

In some aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

Figure 4:
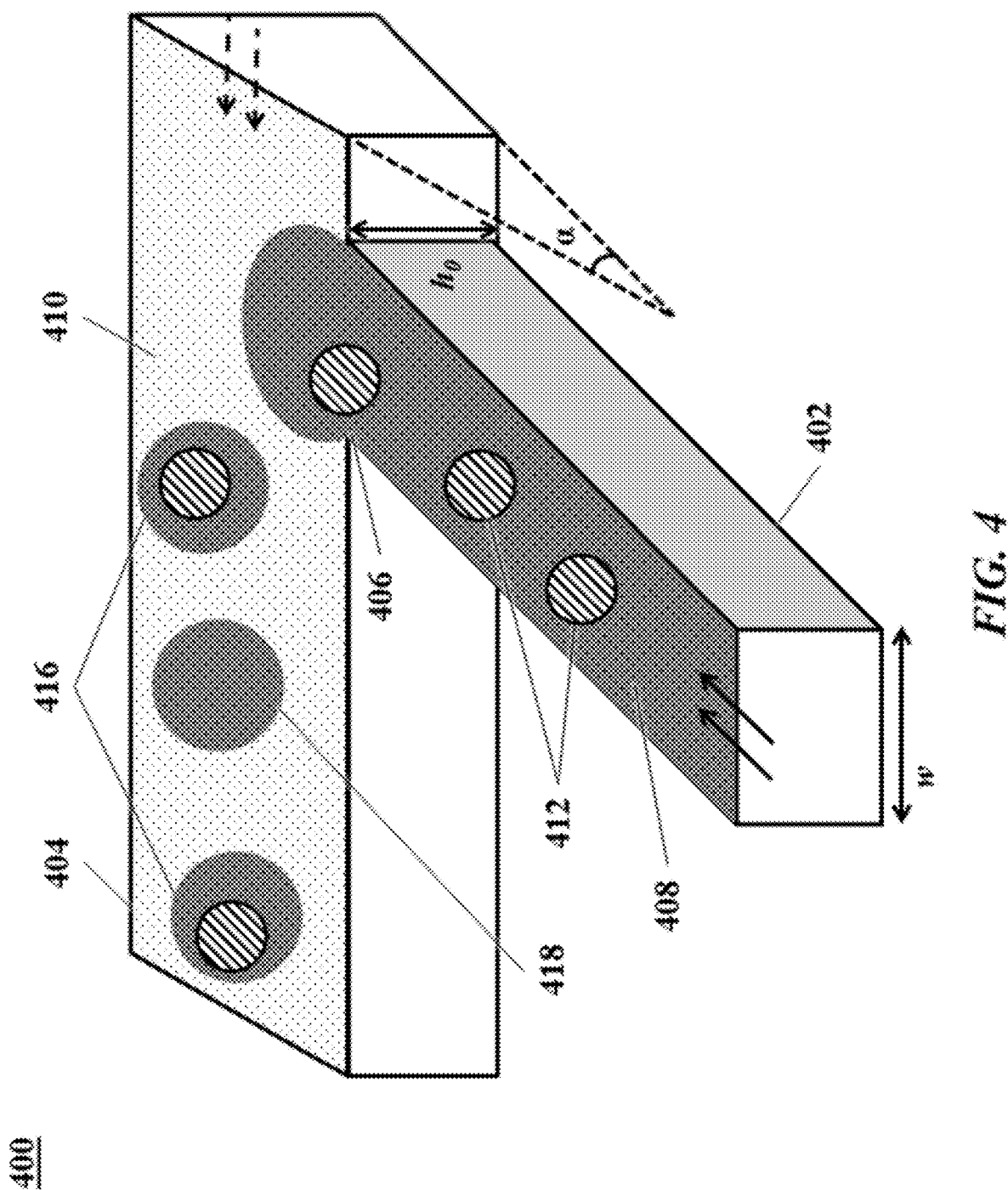
FIG. 4 shows an example of a microfluidic channel structure for the controlled partitioning of beads into discrete droplets.

FIG. 4 shows an example of a microfluidic channel structure for the controlled partitioning of beads into discrete droplets. A channel structure 400 can include a channel segment 402 communicating at a channel junction 406 (or intersection) with a reservoir 404. The reservoir 404 can be a chamber. Any reference to "reservoir," as used herein, can also refer to a "chamber." In operation, an aqueous fluid 408 that includes suspended beads 412 may be transported along the channel segment 402 into the junction 406 to meet a second fluid 410 that is immiscible with the aqueous fluid 408 in the reservoir 404 to create droplets 416, 418 of the aqueous fluid 408 flowing into the reservoir 404. At the junction 406 where the aqueous fluid 408 and the second fluid 410 meet, droplets can form based on factors such as the hydrodynamic forces at the junction 406, flow rates of the two fluids 408, 410, fluid properties, and certain geometric parameters (e.g., w, $h_0$, α, etc.) of the channel structure 400. A plurality of droplets can be collected in the reservoir 404 by continuously injecting the aqueous fluid 408 from the channel segment 402 through the junction 406.

A discrete droplet generated may include a bead (e.g., as in occupied droplets 416). Alternatively, a discrete droplet generated may include more than one bead. Alternatively, a discrete droplet generated may not include any beads (e.g., as in unoccupied droplet 418). In some instances, a discrete droplet generated may contain one or more analyte carriers, as described elsewhere herein. In some instances, a discrete droplet generated may comprise one or more reagents, as described elsewhere herein.

In some instances, the aqueous fluid 408 can have a substantially uniform concentration or frequency of beads 412. The beads 412 can be introduced into the channel segment 402 from a separate channel (not shown in FIG. 4). The frequency of beads 412 in the channel segment 402 may be controlled by controlling the frequency in which the beads 412 are introduced into the channel segment 402 and/or the relative flow rates of the fluids in the channel segment 402 and the separate channel. In some instances, the beads can be introduced into the channel segment 402 from a plurality of different channels, and the frequency controlled accordingly.

In some instances, the aqueous fluid 408 in the channel segment 402 can comprise analyte carriers (e.g., described with reference to FIGS. 1 and 2). In some instances, the aqueous fluid 408 can have a substantially uniform concentration or frequency of analyte carriers. As with the beads, the analyte carriers can be introduced into the channel segment 402 from a separate channel. The frequency or concentration of the analyte carriers in the aqueous fluid 408 in the channel segment 402 may be controlled by controlling the frequency in which the analyte carriers are introduced into the channel segment 402 and/or the relative flow rates of the fluids in the channel segment 402 and the separate channel. In some instances, the analyte carriers can be introduced into the channel segment 402 from a plurality of different channels, and the frequency controlled accordingly. In some instances, a first separate channel can introduce beads and a second separate channel can introduce analyte carriers into the channel segment 402. The first separate channel introducing the beads may be upstream or downstream of the second separate channel introducing the analyte carriers.

The second fluid 410 can comprise an oil, such as a fluorinated oil, that includes a fluorosurfactant for stabilizing the resulting droplets, for example, inhibiting subsequent coalescence of the resulting droplets.

In some instances, the second fluid 410 may not be subjected to and/or directed to any flow in or out of the reservoir 404. For example, the second fluid 410 may be substantially stationary in the reservoir 404. In some instances, the second fluid 410 may be subjected to flow within the reservoir 404, but not in or out of the reservoir 404, such as via application of pressure to the reservoir 404 and/or as affected by the incoming flow of the aqueous fluid 408 at the junction 406. Alternatively, the second fluid 410 may be subjected and/or directed to flow in or out of the reservoir 404. For example, the reservoir 404 can be a channel directing the second fluid 410 from upstream to downstream, transporting the generated droplets.

The channel structure 400 at or near the junction 406 may have certain geometric features that at least partly determine the sizes of the droplets formed by the channel structure 400. The channel segment 402 can have a height, $h_0$ and width, w, at or near the junction 406. By way of example, the channel segment 402 can comprise a rectangular cross-section that leads to a reservoir 404 having a wider cross-section (such as in width or diameter). Alternatively, the cross-section of the channel segment 402 can be other shapes, such as a circular shape, trapezoidal shape, polygonal shape, or any other shapes. The top and bottom walls of the reservoir 404 at or near the junction 406 can be inclined at an expansion angle, α. The expansion angle, α, allows the tongue (portion of the aqueous fluid 408 leaving channel segment 402 at junction 406 and entering the reservoir 404 before droplet formation) to increase in depth and facilitate decrease in curvature of the intermediately formed droplet. Droplet size may decrease with increasing expansion angle. The resulting droplet radius, $R_d$, may be predicted by the following equation for the aforementioned geometric parameters of $h_0$, w, and α:

$$R_d \approx 0.44\left(1 + 2.2\sqrt{\tan \alpha}\, \frac{w}{h_0}\right)\frac{h_0}{\sqrt{\tan \alpha}}$$

By way of example, for a channel structure with w=21 μm, h=21 μm, and α=3°, the predicted droplet size is 121 μm. In another example, for a channel structure with w=25 μm, h=25 μm, and α=5°, the predicted droplet size is 123 μm. In another example, for a channel structure with w=28 μm, h=28 μm, and α=7°, the predicted droplet size is 124 μm.

In some instances, the expansion angle, α, may be between a range of from about 0.5° to about 4°, from about 0.10 to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less. In some instances, the width, w, can be between a range of from about 100 micrometers (μm) to about 500 μm. In some instances, the width, w, can be between a range of from about 10 μm to about 200 μm. Alternatively, the width can be less than about 10 μm. Alternatively, the width can be greater than about 500 μm. In some instances, the flow rate of the aqueous fluid 408 entering the junction 406 can be between about 0.04 microliters (μL)/minute (min) and about 40 μL/min. In some instances, the flow rate of the aqueous fluid 408 entering the junction 406 can be between about 0.01 microliters (μL)/minute (min) and about 100 μL/min. Alternatively, the flow rate of the aqueous fluid 408 entering the junction 406 can be less than about 0.01 μL/min. Alternatively, the flow rate of the aqueous fluid 408 entering the junction 406 can be greater than about 40 μL/min, such as 45 μL/min, 50 μl/min, 55 μl/min, 60 μl/min, 65 μl/min, 70 μL/min, 75 μl/min, 80 μl/min, 85 μl/min, 90 μl/min, 95 μl/min, 100 μl/min, 110 μl/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 408 entering the junction 406.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

The throughput of droplet generation can be increased by increasing the points of generation, such as increasing the number of junctions (e.g., junction 406) between aqueous fluid 408 channel segments (e.g., channel segment 402) and the reservoir 404. Alternatively or in addition, the throughput of droplet generation can be increased by increasing the flow rate of the aqueous fluid 408 in the channel segment 402.

Figure 5:
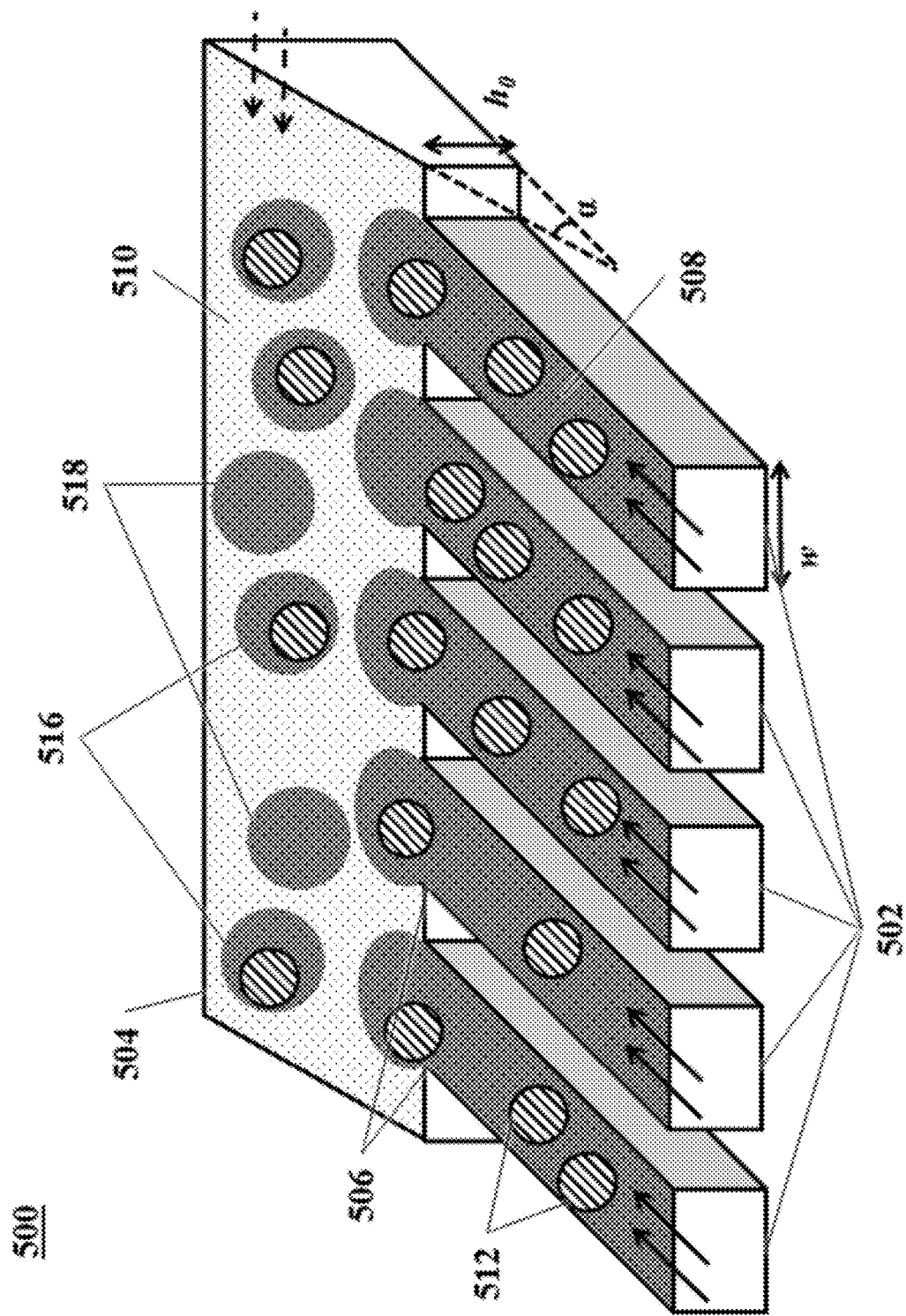
FIG. 5 shows an example of a microfluidic channel structure for increased droplet generation throughput.

FIG. 5 shows an example of a microfluidic channel structure for increased droplet generation throughput. A microfluidic channel structure 500 can comprise a plurality of channel segments 502 and a reservoir 504. Each of the plurality of channel segments 502 may be in fluid communication with the reservoir 504. The channel structure 500 can comprise a plurality of channel junctions 506 between the plurality of channel segments 502 and the reservoir 504. Each channel junction can be a point of droplet generation. The channel segment 402 from the channel structure 400 in FIG. 4 and any description to the components thereof may correspond to a given channel segment of the plurality of channel segments 502 in channel structure 500 and any description to the corresponding components thereof. The reservoir 404 from the channel structure 400 and any description to the components thereof may correspond to the reservoir 504 from the channel structure 500 and any description to the corresponding components thereof.

Each channel segment of the plurality of channel segments 502 may comprise an aqueous fluid 508 that includes suspended beads 512. The reservoir 504 may comprise a second fluid 510 that is immiscible with the aqueous fluid 508. In some instances, the second fluid 510 may not be subjected to and/or directed to any flow in or out of the reservoir 504. For example, the second fluid 510 may be substantially stationary in the reservoir 504. In some instances, the second fluid 510 may be subjected to flow within the reservoir 504, but not in or out of the reservoir 504, such as via application of pressure to the reservoir 504 and/or as affected by the incoming flow of the aqueous fluid 508 at the junctions. Alternatively, the second fluid 510 may be subjected and/or directed to flow in or out of the reservoir 504. For example, the reservoir 504 can be a channel directing the second fluid 510 from upstream to downstream, transporting the generated droplets.

In operation, the aqueous fluid 508 that includes suspended beads 512 may be transported along the plurality of channel segments 502 into the plurality of junctions 506 to meet the second fluid 510 in the reservoir 504 to create droplets 516, 518. A droplet may form from each channel segment at each corresponding junction with the reservoir 504. At the junction where the aqueous fluid 508 and the second fluid 510 meet, droplets can form based on factors such as the hydrodynamic forces at the junction, flow rates of the two fluids 508, 510, fluid properties, and certain geometric parameters (e.g., w, $h_0$, a, etc.) of the channel structure 500, as described elsewhere herein. A plurality of droplets can be collected in the reservoir 504 by continuously injecting the aqueous fluid 508 from the plurality of channel segments 502 through the plurality of junctions 506. Throughput may significantly increase with the parallel channel configuration of channel structure 500. For example, a channel structure having five inlet channel segments comprising the aqueous fluid 508 may generate droplets five times as frequently than a channel structure having one inlet channel segment, provided that the fluid flow rate in the channel segments are substantially the same. The fluid flow rate in the different inlet channel segments may or may not be substantially the same. A channel structure may have as many parallel channel segments as is practical and allowed for the size of the reservoir. For example, the channel structure may have at least about 2, 3, 4, 5, 6, 7, 8, 9, 10, 20, 30, 40, 50, 60, 70, 80, 90, 100, 150, 500, 250, 300, 350, 400, 450, 500, 600, 700, 800, 900, 1000, 1500, 5000 or more parallel or substantially parallel channel segments.

The geometric parameters, w, $h_0$, and a, may or may not be uniform for each of the channel segments in the plurality of channel segments 502. For example, each channel segment may have the same or different widths at or near its respective channel junction with the reservoir 504. For example, each channel segment may have the same or different height at or near its respective channel junction with the reservoir 504. In another example, the reservoir 504 may have the same or different expansion angle at the different channel junctions with the plurality of channel segments 502. When the geometric parameters are uniform, beneficially, droplet size may also be controlled to be uniform even with the increased throughput. In some instances, when it is desirable to have a different distribution of droplet sizes, the geometric parameters for the plurality of channel segments 502 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

Figure 6:
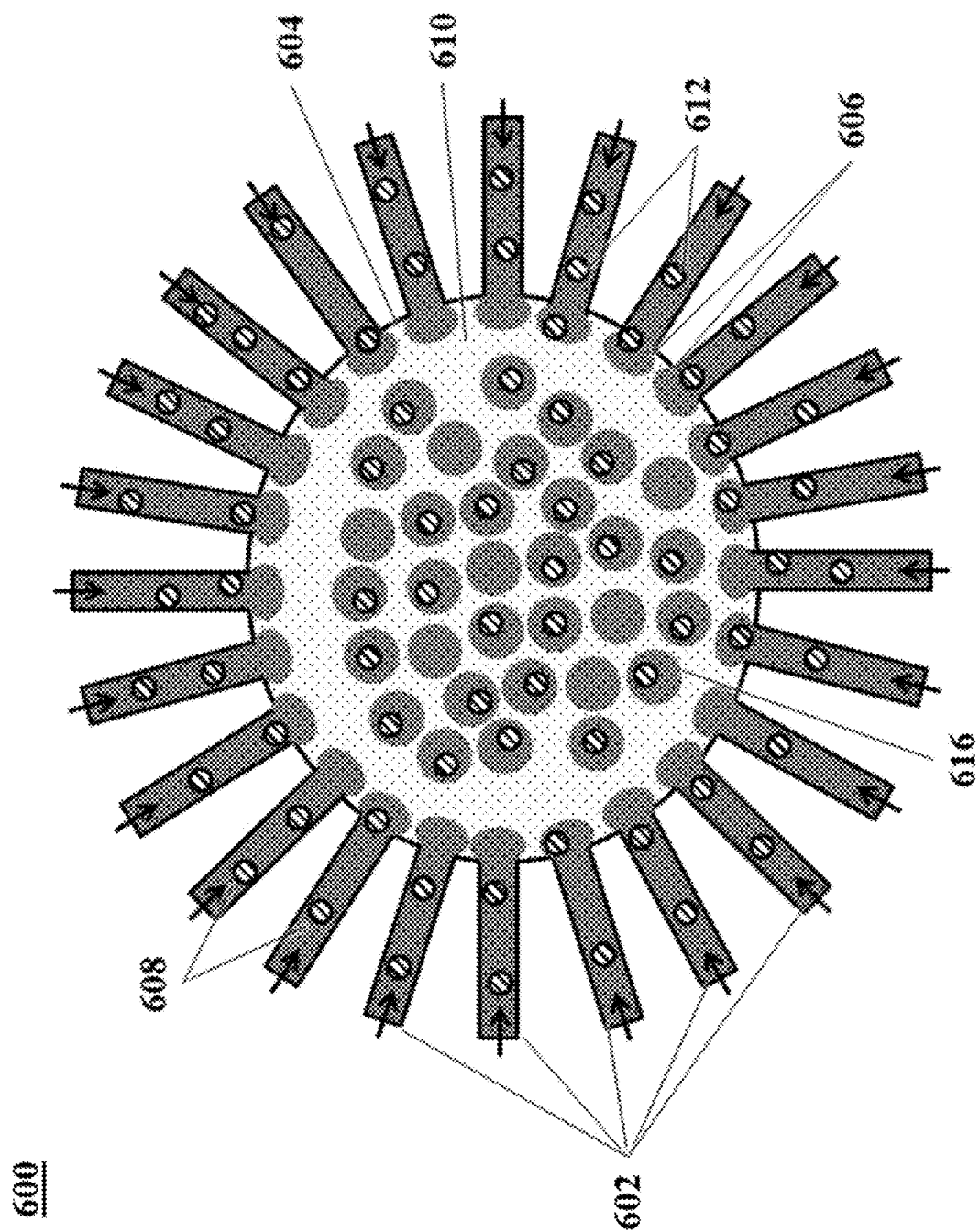
FIG. 6 shows another example of a microfluidic channel structure for increased droplet generation throughput.

FIG. 6 shows another example of a microfluidic channel structure for increased droplet generation throughput. A microfluidic channel structure 600 can comprise a plurality of channel segments 602 arranged generally circularly around the perimeter of a reservoir 604. Each of the plurality of channel segments 602 may be in fluid communication with the reservoir 604. The channel structure 600 can comprise a plurality of channel junctions 606 between the plurality of channel segments 602 and the reservoir 604. Each channel junction can be a point of droplet generation. The channel segment 402 from the channel structure 400 in FIG. 2 and any description to the components thereof may correspond to a given channel segment of the plurality of channel segments 602 in channel structure 600 and any description to the corresponding components thereof. The reservoir 404 from the channel structure 400 and any description to the components thereof may correspond to the reservoir 604 from the channel structure 600 and any description to the corresponding components thereof.

Each channel segment of the plurality of channel segments 602 may comprise an aqueous fluid 608 that includes suspended beads 612. The reservoir 604 may comprise a second fluid 610 that is immiscible with the aqueous fluid 608. In some instances, the second fluid 610 may not be subjected to and/or directed to any flow in or out of the reservoir 604. For example, the second fluid 610 may be substantially stationary in the reservoir 604. In some instances, the second fluid 610 may be subjected to flow within the reservoir 604, but not in or out of the reservoir 604, such as via application of pressure to the reservoir 604 and/or as affected by the incoming flow of the aqueous fluid 608 at the junctions. Alternatively, the second fluid 610 may be subjected and/or directed to flow in or out of the reservoir 604. For example, the reservoir 604 can be a channel directing the second fluid 610 from upstream to downstream, transporting the generated droplets.

In operation, the aqueous fluid 608 that includes suspended beads 612 may be transported along the plurality of channel segments 602 into the plurality of junctions 606 to meet the second fluid 610 in the reservoir 604 to create a plurality of droplets 616. A droplet may form from each channel segment at each corresponding junction with the reservoir 604. At the junction where the aqueous fluid 608 and the second fluid 610 meet, droplets can form based on factors such as the hydrodynamic forces at the junction, flow rates of the two fluids 608, 610, fluid properties, and certain geometric parameters (e.g., widths and heights of the channel segments 602, expansion angle of the reservoir 604, etc.) of the channel structure 600, as described elsewhere herein. A plurality of droplets can be collected in the reservoir 604 by continuously injecting the aqueous fluid 608 from the plurality of channel segments 602 through the plurality of junctions 606. Throughput may significantly increase with the substantially parallel channel configuration of the channel structure 600. A channel structure may have as many substantially parallel channel segments as is practical and allowed for by the size of the reservoir. For example, the channel structure may have at least about 2, 3, 4, 5, 6, 7, 8, 9, 10, 20, 30, 40, 50, 60, 70, 80, 90, 100, 150, 200, 250, 300, 350, 400, 450, 500, 600, 700, 800, 900, 1000, 1500, 5000 or more parallel or substantially parallel channel segments. The plurality of channel segments may be substantially evenly spaced apart, for example, around an edge or perimeter of the reservoir. Alternatively, the spacing of the plurality of channel segments may be uneven.

The reservoir 604 may have an expansion angle, α (not shown in FIG. 6) at or near each channel junction. Each channel segment of the plurality of channel segments 602 may have a width, w, and a height, $h_0$, at or near the channel junction. The geometric parameters, w, $h_0$, and α, may or may not be uniform for each of the channel segments in the plurality of channel segments 602. For example, each channel segment may have the same or different widths at or near its respective channel junction with the reservoir 604. For example, each channel segment may have the same or different height at or near its respective channel junction with the reservoir 604.

The reservoir 604 may have the same or different expansion angle at the different channel junctions with the plurality of channel segments 602. For example, a circular reservoir (as shown in FIG. 6) may have a conical, dome-like, or hemispherical ceiling (e.g., top wall) to provide the same or substantially same expansion angle for each channel segments 602 at or near the plurality of channel junctions 606. When the geometric parameters are uniform, beneficially, resulting droplet size may be controlled to be uniform even with the increased throughput. In some instances, when it is desirable to have a different distribution of droplet sizes, the geometric parameters for the plurality of channel segments 602 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size. The beads and/or analyte carrier injected into the droplets may or may not have uniform size.

FIG. 7A shows a cross-section view of another example of a microfluidic channel structure with a geometric feature for controlled partitioning. A channel structure 700 can include a channel segment 702 communicating at a channel junction 706 (or intersection) with a reservoir 704. In some instances, the channel structure 700 and one or more of its components can correspond to the channel structure 100 and one or more of its components. FIG. 7B shows a perspective view of the channel structure 700 of FIG. 7A.

An aqueous fluid 712 comprising a plurality of particles 716 may be transported along the channel segment 702 into the junction 706 to meet a second fluid 714 (e.g., oil, etc.) that is immiscible with the aqueous fluid 712 in the reservoir 704 to create droplets 720 of the aqueous fluid 712 flowing into the reservoir 704. At the junction 706 where the aqueous fluid 712 and the second fluid 714 meet, droplets can form based on factors such as the hydrodynamic forces at the junction 706, relative flow rates of the two fluids 712, 714, fluid properties, and certain geometric parameters (e.g., Δh, etc.) of the channel structure 700. A plurality of droplets can be collected in the reservoir 704 by continuously injecting the aqueous fluid 712 from the channel segment 702 at the junction 706.

A discrete droplet generated may comprise one or more particles of the plurality of particles 716. As described elsewhere herein, a particle may be any particle, such as a bead, cell bead, gel bead, analyte carrier, macromolecular constituents of analyte carrier, or other particles. Alternatively, a discrete droplet generated may not include any particles.

In some instances, the aqueous fluid 712 can have a substantially uniform concentration or frequency of particles 716. As described elsewhere herein (e.g., with reference to FIG. 4), the particles 716 (e.g., beads) can be introduced into the channel segment 702 from a separate channel (not shown in FIG. 7). The frequency of particles 716 in the channel segment 702 may be controlled by controlling the frequency in which the particles 716 are introduced into the channel segment 702 and/or the relative flow rates of the fluids in the channel segment 702 and the separate channel. In some instances, the particles 716 can be introduced into the channel segment 702 from a plurality of different channels, and the frequency controlled accordingly. In some instances, different particles may be introduced via separate channels. For example, a first separate channel can introduce beads and a second separate channel can introduce analyte carriers into the channel segment 702. The first separate channel introducing the beads may be upstream or downstream of the second separate channel introducing the analyte carriers.

In some instances, the second fluid 714 may not be subjected to and/or directed to any flow in or out of the reservoir 704. For example, the second fluid 714 may be substantially stationary in the reservoir 704. In some instances, the second fluid 714 may be subjected to flow within the reservoir 704, but not in or out of the reservoir 704, such as via application of pressure to the reservoir 704 and/or as affected by the incoming flow of the aqueous fluid 712 at the junction 706. Alternatively, the second fluid 714 may be subjected and/or directed to flow in or out of the reservoir 704. For example, the reservoir 704 can be a channel directing the second fluid 714 from upstream to downstream, transporting the generated droplets.

The channel structure 700 at or near the junction 706 may have certain geometric features that at least partly determine the sizes and/or shapes of the droplets formed by the channel structure 700. The channel segment 702 can have a first cross-section height, $h_1$, and the reservoir 704 can have a second cross-section height, $h_2$. The first cross-section height, $h_1$, and the second cross-section height, $h_2$, may be different, such that at the junction 706, there is a height difference of Δh. The second cross-section height, $h_2$, may be greater than the first cross-section height, $h_1$. In some instances, the reservoir may thereafter gradually increase in cross-section height, for example, the more distant it is from the junction 706. In some instances, the cross-section height of the reservoir may increase in accordance with expansion angle, β, at or near the junction 706. The height difference, Δh, and/or expansion angle, β, can allow the tongue (portion of the aqueous fluid 712 leaving channel segment 702 at junction 706 and entering the reservoir 704 before droplet formation) to increase in depth and facilitate decrease in curvature of the intermediately formed droplet. For example, droplet size may decrease with increasing height difference and/or increasing expansion angle.

The height difference, Δh, can be at least about 1 μm. Alternatively, the height difference can be at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500 μm or more. Alternatively, the height difference can be at most about 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1 μm or less. In some instances, the expansion angle, β, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less.

In some instances, the flow rate of the aqueous fluid 712 entering the junction 706 can be between about 0.04 microliters (μL)/minute (min) and about 40 μL/min. In some instances, the flow rate of the aqueous fluid 712 entering the junction 706 can be between about 0.01 microliters (μL)/minute (min) and about 100 μL/min. Alternatively, the flow rate of the aqueous fluid 712 entering the junction 706 can be less than about 0.01 μL/min. Alternatively, the flow rate of the aqueous fluid 712 entering the junction 706 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 712 entering the junction 706. The second fluid 714 may be stationary, or substantially stationary, in the reservoir 704. Alternatively, the second fluid 714 may be flowing, such as at the above flow rates described for the aqueous fluid 712.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

While FIGS. 7A and 7B illustrate the height difference, Δh, being abrupt at the junction 706 (e.g., a step increase), the height difference may increase gradually (e.g., from about 0 μm to a maximum height difference). Alternatively, the height difference may decrease gradually (e.g., taper) from a maximum height difference. A gradual increase or decrease in height difference, as used herein, may refer to a continuous incremental increase or decrease in height difference, wherein an angle between any one differential segment of a height profile and an immediately adjacent differential segment of the height profile is greater than 90°. For example, at the junction 706, a bottom wall of the channel and a bottom wall of the reservoir can meet at an angle greater than 90°. Alternatively or in addition, a top wall (e.g., ceiling) of the channel and a top wall (e.g., ceiling) of the reservoir can meet an angle greater than 90°. A gradual increase or decrease may be linear or non-linear (e.g., exponential, sinusoidal, etc.). Alternatively or in addition, the height difference may variably increase and/or decrease linearly or non-linearly. While FIGS. 7A and 7B illustrate the expanding reservoir cross-section height as linear (e.g., constant expansion angle, β), the cross-section height may expand non-linearly. For example, the reservoir may be defined at least partially by a dome-like (e.g., hemispherical) shape having variable expansion angles. The cross-section height may expand in any shape.

The channel networks, e.g., as described above or elsewhere herein, can be fluidly coupled to appropriate fluidic components. For example, the inlet channel segments are fluidly coupled to appropriate sources of the materials they are to deliver to a channel junction. These sources may include any of a variety of different fluidic components, from simple reservoirs defined in or connected to a body structure of a microfluidic device, to fluid conduits that deliver fluids from off-device sources, manifolds, fluid flow units (e.g., actuators, pumps, compressors) or the like. Likewise, the outlet channel segment (e.g., channel segment 208, reservoir 604, etc.) may be fluidly coupled to a receiving vessel or conduit for the partitioned cells for subsequent processing. Again, this may be a reservoir defined in the body of a microfluidic device, or it may be a fluidic conduit for delivering the partitioned cells to a subsequent process operation, instrument or component.

The methods and systems described herein may be used to greatly increase the efficiency of single cell applications and/or other applications receiving droplet-based input. For example, following the sorting of occupied cells and/or appropriately-sized cells, subsequent operations that can be performed can include generation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-T sequence during sequencing and/or sequence the 5' end of a polynucleotide sequence. The amplification products, for example, first amplification products and/or second amplification products, may be subject to sequencing for sequence analysis. In some cases, amplification may be performed using the Partial Hairpin Amplification for Sequencing (PHASE) method.

A variety of applications require the evaluation of the presence and quantification of different analyte carrier or organism types within a population of analyte carriers, including, for example, microbiome analysis and characterization, environmental testing, food safety testing, epidemiological analysis, e.g., in tracing contamination or the like.

Computer Systems

Figure 10:
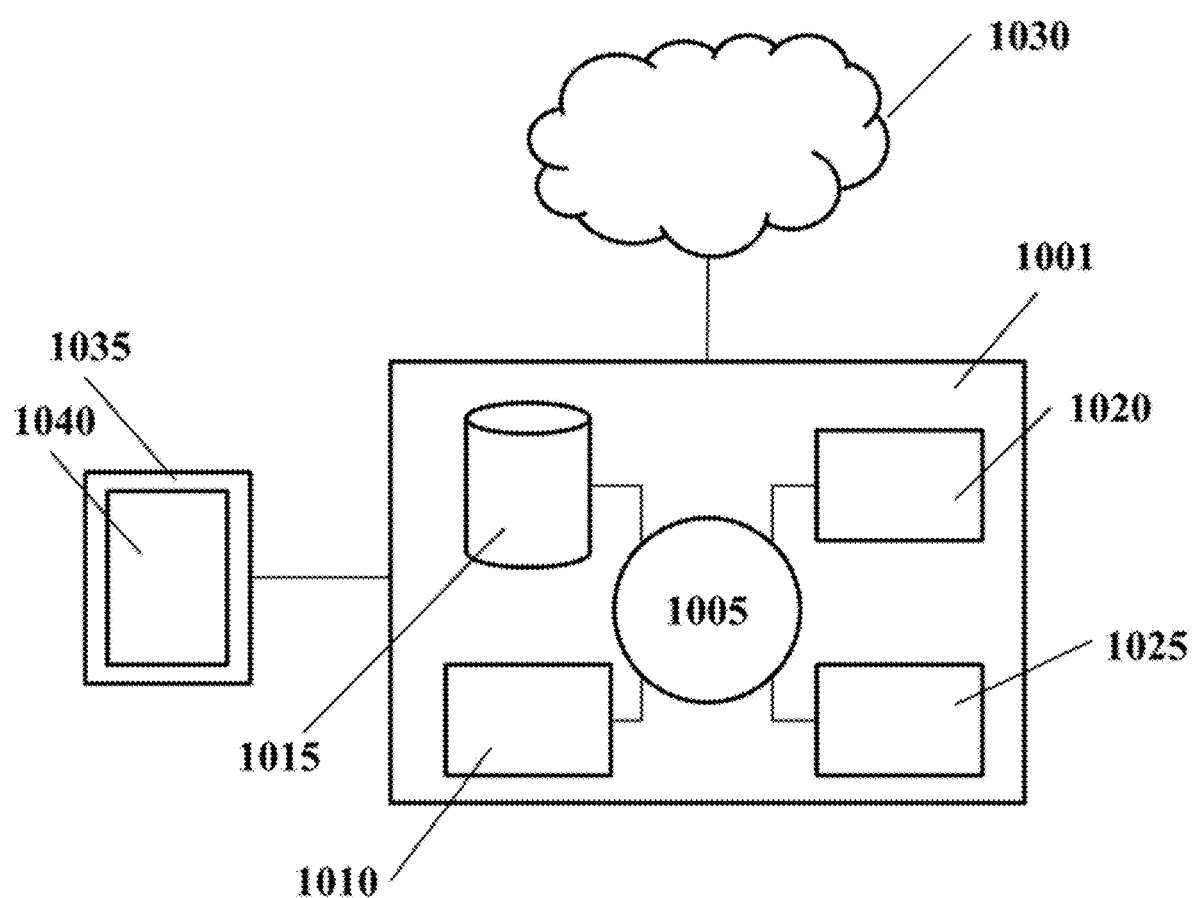
FIG. 10 shows a computer system that is programmed or otherwise configured to implement methods provided herein.

The present disclosure provides computer systems that are programmed to implement methods of the disclosure. FIG. 10 shows a computer system 1001 that is programmed or otherwise configured to control a microfluidics system (e.g., fluid flow), sort occupied droplets from unoccupied droplets, polymerize droplets, (iv) perform sequencing applications, and the like. The computer system 1001 can regulate various aspects of the present disclosure, such as, for example, e.g., regulating fluid flow rate in one or more channels in a microfluidic structure. The computer system 1001 can be an electronic device of a user or a computer system that is remotely located with respect to the electronic device. The electronic device can be a mobile electronic device.

The computer system 1001 includes a central processing unit (CPU, also "processor" and "computer processor" herein) 1005, which can be a single core or multi core processor, or a plurality of processors for parallel processing. The computer system 1001 also includes memory or memory location 1010 (e.g., random-access memory, read-only memory, flash memory), electronic storage unit 1015 (e.g., hard disk), communication interface 1020 (e.g., network adapter) for communicating with one or more other systems, and peripheral devices 1025, such as cache, other memory, data storage and/or electronic display adapters. The memory 1010, storage unit 1015, interface 1020 and peripheral devices 1025 are in communication with the CPU 1005 through a communication bus (solid lines), such as a motherboard. The storage unit 1015 can be a data storage unit (or data repository) for storing data. The computer system 1001 can be operatively coupled to a computer network ("network") 1030 with the aid of the communication interface 1020. The network 1030 can be the Internet, an internet and/or extranet, or an intranet and/or extranet that is in communication with the Internet. The network 1030 in some cases is a telecommunication and/or data network. The network 1030 can include one or more computer servers, which can enable distributed computing, such as cloud computing. The network 1030, in some cases with the aid of the computer system 1001, can implement a peer-to-peer network, which may enable devices coupled to the computer system 1001 to behave as a client or a server.

The CPU 1005 can execute a sequence of machine-readable instructions, which can be embodied in a program or software. The instructions may be stored in a memory location, such as the memory 1010. The instructions can be directed to the CPU 1005, which can subsequently program or otherwise configure the CPU 1005 to implement methods of the present disclosure. Examples of operations performed by the CPU 1005 can include fetch, decode, execute, and writeback.

The CPU 1005 can be part of a circuit, such as an integrated circuit. One or more other components of the system 1001 can be included in the circuit. In some cases, the circuit is an application specific integrated circuit (ASIC).

The storage unit 1015 can store files, such as drivers, libraries and saved programs. The storage unit 1015 can store user data, e.g., user preferences and user programs. The computer system 1001 in some cases can include one or more additional data storage units that are external to the computer system 1001, such as located on a remote server that is in communication with the computer system 1001 through an intranet or the Internet.

The computer system 1001 can communicate with one or more remote computer systems through the network 1030. For instance, the computer system 1001 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1001 via the network 1030.

Methods as described herein can be implemented by way of machine (e.g., computer processor) executable code stored on an electronic storage location of the computer system 1001, such as, for example, on the memory 1010 or electronic storage unit 1015. The machine executable or machine readable code can be provided in the form of software. During use, the code can be executed by the processor 1005. In some cases, the code can be retrieved from the storage unit 1015 and stored on the memory 1010 for ready access by the processor 1005. In some situations, the electronic storage unit 1015 can be precluded, and machine-executable instructions are stored on memory 1010.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1001 can include or be in communication with an electronic display 1035 that comprises a user interface (UI) 1040 for providing, for example, results of sequencing analysis, etc. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 1005. The algorithm can, for example, e.g., perform sequencing, etc.

Devices, systems, compositions and methods of the present disclosure may be used for various applications, such as, for example, processing a single analyte (e.g., RNA, DNA, or protein) or multiple analytes (e.g., DNA and RNA, DNA and protein, RNA and protein, or RNA, DNA and protein) from a single cell. For example, an analyte carrier (e.g., a cell or cell bead) is partitioned in a partition (e.g., droplet), and multiple analytes from the analyte carrier are processed for subsequent processing. The multiple analytes may be from the single cell. This may enable, for example, simultaneous proteomic, transcriptomic and genomic analysis of the cell.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for processing a labelled cell, comprising:
   (a) partitioning a plurality of labelled cells into a plurality of partitions, wherein a partition of the plurality of partitions comprises a cell barcode molecule and a labelled cell of the plurality of labelled cells, wherein the labelled cell comprises (i) a first labelling agent coupled to a first protein of the labelled cell, and (ii) a second labelling agent coupled to a second protein of the labelled cell, wherein the first labelling agent comprises a first proximity probe comprising a first barcode sequence and a first unique molecular identifier (UMI), wherein the second labelling agent comprises a second proximity probe comprising a second barcode sequence and a second UMI, and wherein the cell barcode molecule comprises a third UMI and a cell barcode sequence that is complementary to the first and second barcode sequences; and
   (b) generating a barcoded molecule in the partition, wherein the barcoded molecule comprises the first barcode sequence, the first UMI, the second barcode sequence, the second UMI, the third UMI, and the cell barcode sequence, or derivatives thereof.

2. The method of claim 1, wherein the first protein is a surface protein.

3. The method of claim 1, wherein the second protein is a surface protein.

4. The method of claim 1, wherein (a) further comprises partitioning in the partition a support comprising the cell barcode molecule.

5. The method of claim 4, wherein the support comprises a plurality of cell barcode molecules comprising the cell barcode molecule attached thereto.

6. The method of claim 5, wherein cell barcode molecules of the plurality of cell barcode molecules comprise the cell barcode sequence.

7. The method of claim 1, wherein the labelled cell is a single labelled cell and the cell barcode sequence is specific to the single labelled cell.

8. The method of claim 4, wherein the cell barcode molecule is releasably attached to the support.

9. The method of claim 1, wherein the partition is a droplet.

10. The method of claim 1, wherein the partition is a well.

11. The method of claim 1, wherein the first protein is an internal protein.

12. The method of claim 1, wherein the second protein is an internal protein.

13. The method of claim 1, wherein the first barcode sequence comprises a barcode sequence corresponding to a type of the first labelling agent or a type of the first protein.

14. The method of claim 1, wherein the first labelling agent comprises at least one additional proximity probe, wherein the at least one additional proximity probe comprises a donor probe comprising a donor sequence or an acceptor probe comprising an acceptor sequence.

15. The method of claim 1, wherein the first proximity probe is:
   (a) single stranded; or
   (b) single stranded and comprises a donor sequence or an acceptor sequence at an end of the first proximity probe, wherein the cell barcode molecule comprises a first attachment sequence complementary to the donor sequence and a second attachment sequence complementary to the acceptor sequence.

16. The method of claim 1, wherein the cell barcode molecule comprises a first single stranded portion, a double stranded portion, and a second single stranded portion, wherein the first single stranded portion and the second single stranded portion flank the double stranded portion, wherein the first single stranded portion comprises a first attachment sequence complementary to a donor sequence of the first proximity probe, and wherein the second single stranded portion comprises a second attachment sequence complementary to an acceptor sequence of the second proximity probe.

* * * * *